US011971337B2

(12) United States Patent
Grille et al.

(10) Patent No.: US 11,971,337 B2
(45) Date of Patent: Apr. 30, 2024

(54) COMPOSITIONS AND METHODS FOR SIMULTANEOUS INACTIVATION OF ALKALINE PHOSPHATASE AND PEROXIDASE ENZYMES DURING AUTOMATED MULTIPLEX TISSUE STAINING ASSAYS

(71) Applicant: Ventana Medical Systems, Inc., Tucson, AZ (US)

(72) Inventors: James Grille, Tucson, AZ (US); Brian D. Kelly, Tucson, AZ (US); Jerome Kosmeder, II, Tucson, AZ (US); Eric May, Oro Valley, AZ (US); Noemi Sebastiao, Tucson, AZ (US); Pamela Wirth, Tucson, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 117 days.

(21) Appl. No.: 17/493,477

(22) Filed: Oct. 4, 2021

(65) Prior Publication Data
US 2022/0026319 A1     Jan. 27, 2022

Related U.S. Application Data

(60) Division of application No. 15/807,612, filed on Nov. 9, 2017, now Pat. No. 11,162,877, which is a continuation of application No. PCT/EP2016/060263, filed on May 9, 2016.

(60) Provisional application No. 62/159,297, filed on May 10, 2015.

(51) Int. Cl.
| | |
|---|---|
| G01N 1/30 | (2006.01) |
| A61K 49/00 | (2006.01) |
| C01B 15/01 | (2006.01) |
| C01B 21/08 | (2006.01) |
| C07C 55/02 | (2006.01) |
| C07C 55/22 | (2006.01) |
| C07C 55/24 | (2006.01) |
| C12N 9/99 | (2006.01) |
| G01N 33/52 | (2006.01) |

(52) U.S. Cl.
CPC ............. *G01N 1/30* (2013.01); *C01B 15/01* (2013.01); *C01B 21/08* (2013.01); *C07C 55/02* (2013.01); *C07C 55/22* (2013.01); *C07C 55/24* (2013.01); *C12N 9/99* (2013.01); *G01N 33/52* (2013.01); *A61K 49/001* (2013.01); *G01N 2001/302* (2013.01); *G01N 2333/902* (2013.01); *G01N 2333/908* (2013.01); *G01N 2333/916* (2013.01)

(58) Field of Classification Search
None
See application file for complete search history.

(56) References Cited

U.S. PATENT DOCUMENTS

| | | |
|---|---|---|
| 2004/0248223 A1 | 12/2004 | Magnotti |
| 2005/0176072 A1 | 8/2005 | Martin et al. |
| 2006/0160069 A1 | 7/2006 | Chau et al. |
| 2010/0209924 A1 | 8/2010 | Yamaguchi |

FOREIGN PATENT DOCUMENTS

| | | | | |
|---|---|---|---|---|
| CN | 1333691 A | | 1/2002 | |
| CN | 103562390 A | * | 2/2014 | ................ A61P 1/02 |
| CN | 102458464 B | | 8/2016 | |
| JP | H05505239 A | | 8/1993 | |
| JP | 2010193883 A | | 9/2010 | |
| JP | 2014518062 A | | 7/2014 | |
| WO | WO-9921014 A1 | * | 4/1999 | ......... G01N 33/5005 |
| WO | 00/30675 A2 | | 6/2000 | |
| WO | 2010117325 A1 | | 10/2010 | |
| WO | 2012164083 A1 | | 12/2012 | |

OTHER PUBLICATIONS

By Koldovsky ("Postnatal changes in ß-Galactosidase activity in the jejunum and ileum of Mice, Rabbits and Guinea Pigs" Canadian Journal of Biochemistry, 1966, 423-527, Abstract provided). (Year: 1966).*

* cited by examiner

*Primary Examiner* — Robert J Yamasaki
*Assistant Examiner* — Charles Zoltan Constantine
(74) *Attorney, Agent, or Firm* — Charney IP Law LLC; Thomas M. Finetti

(57) ABSTRACT

Disclosed are compositions and methods for inactivating one or more enzymes in a biological sample.

12 Claims, 39 Drawing Sheets
(39 of 39 Drawing Sheet(s) Filed in Color)

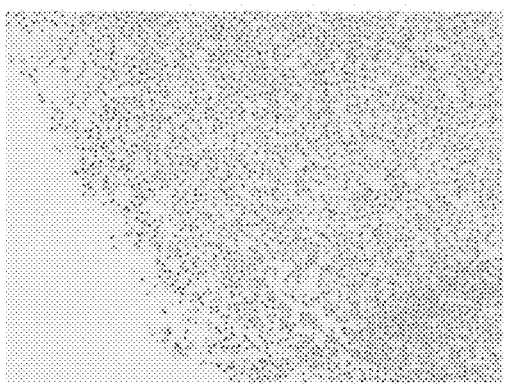
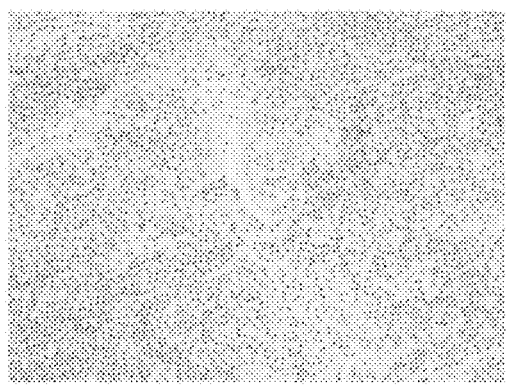
FIG. 1GG　　　　　　　　FIG. 1HH

 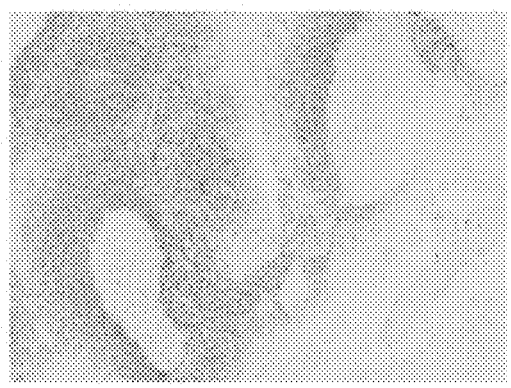
FIG. 4GG     FIG. 4HH

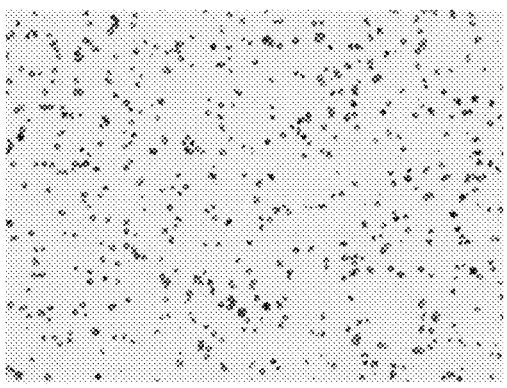
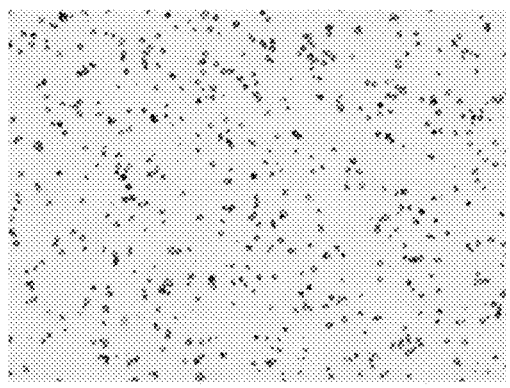
FIG. 7GG  FIG. 7HH

COMPOSITIONS AND METHODS FOR SIMULTANEOUS INACTIVATION OF ALKALINE PHOSPHATASE AND PEROXIDASE ENZYMES DURING AUTOMATED MULTIPLEX TISSUE STAINING ASSAYS

CROSS REFERENCE TO RELATED APPLICATIONS

This patent application is a divisional of U.S. patent application Ser. No. 15/807,612 filed on Nov. 9, 2017, which application is a continuation of International Patent Application No. PCT/EP2016/060263 filed May 9, 2016, which claims priority to and the benefit of U.S. Provisional Patent Application No. 62/159,297 filed May 10, 2015. Each of the above-identified patent applications are incorporated herein by reference as if set forth in their entireties.

STATEMENT OF INDUSTRIAL APPLICABILITY

The present disclosure has industrial applicability in the field of diagnostics.

BACKGROUND OF THE INVENTION

Immunohistochemistry (IHC) is the detection of localized antigens or proteins in tissue sections by the use of labeled antibodies as specific reagents through antigen-antibody interactions that are visualized by a marker such as fluorescent dye, enzyme, or colloidal gold. This detection technique has the advantage of being able to show exactly where a given protein is located within the tissue sample. It is also an effective method to examine the tissues themselves. In situ hybridization, or ISH, refers to the process of detecting, localizing, and quantifying nucleic acids. Both IHC and ISH can be performed on various biological samples, such as tissue (e.g., fresh frozen, formalin fixed paraffin embedded) and cytological samples. Upon recognition of the targets, whether the targets are nucleic acids or antigens, the recognition event can be detected through the use of various labels (e.g., chromogenic, fluorescent, luminescent, radiometric). In situ hybridization (ISH) on tissue includes detecting a nucleic acid by applying a complementary strand of nucleic acid to which a reporter molecule is coupled. Visualization of the reporter molecule allows an observer to localize specific DNA or RNA sequences in a heterogeneous cell population, such as a histological, cytological, or environmental sample. Presently available ISH techniques include silver in situ hybridization (SISH), chromogenic in situ hybridization (CISH) and fluorescence in situ hybridization (FISH).

Chromogenic substrates are used in both IHC and ISH where chromogenic detection offers a simple and cost-effective method of detection. Traditionally, chromogenic substrates precipitate when activated by the appropriate enzyme. That is, the traditional chromogenic substance is converted from a soluble reagent into an insoluble, colored precipitate upon contacting the enzyme. Two such enzymes include horseradish peroxidase (HRP) and alkaline phosphatase (AP).

Multiplex IHC and ISH assays are being developed to detect, for example, multiple tissue antigens, using several alkaline phosphatase or horseradish peroxidase detections steps on a single tissue slide. Enzyme inactivation is important to mitigate improper signal generation in subsequent enzyme detection steps. While there exist methods of at least partially inactivating enzymes, these methods fail to completely inhibit both endogenous and reagent enzyme activity and are susceptible to enzyme reactivation (e.g. hydrogen peroxide is a reversible HRP enzyme inhibitor, but removal of the hydrogen peroxide restores enzyme activity).

Inactivation of enzymes often requires a significant amount of time, which can be multiplied when applied to multiplexed assays. For example, a peroxidase inactivation step may require about one hour per detection cycle. In higher order multiplex assays (e.g. those using four or more chromogen detections steps), such an enzyme kill step would add a significant amount of time to the assay duration. While shorter enzyme inactivation steps may be available, they often require harsh conditions (e.g. heat above 50° C.), which could affect tissue antigen detection signal intensity, tissue morphology, chromogen stability, and counterstain appearance.

BRIEF SUMMARY OF THE INVENTION

In one aspect of the present invention is an enzyme inactivation composition comprising polycarboxylic acid having a pH ranging from about 1 to about 3; a peroxide; and at least one of a preservative or additive. In some embodiments, the polycarboxylic acid is a citrate. In some embodiments, a preservative is selected that also functions as a reversible enzyme inhibitor (e.g. $NaN_3$). In some embodiments, the peroxide is hydrogen peroxide ($H_2O_2$) and the preservative is sodium azide ($NaN_3$). In some embodiments, the peroxide is present in an amount ranging from between about 0.25% to about 5% by total weight of the composition; and the preservative is present in an amount ranging from between about 0.05% to about 1.0% by total weight of the composition. In some embodiments, the enzyme inactivation composition further comprises an elution mitigation agent. In some embodiments, the elution mitigation agent is sodium chloride. In some embodiments, the elution mitigation agent is sodium chloride. In some embodiments, the composition is applied to a biological sample already containing a volume of fluid in contact with the biological sample, wherein a pH of the total volume of fluid in contact with the sample (e.g. a "puddle"), after addition of the enzyme inactivation composition ranges from about 1 to about 3.

In some embodiments, the enzyme inactivation composition comprises citrate having a pH of about 1.5, $H_2O_2$ (about 1% by total weight of the composition), and $NaN_3$ (about 0.08% by total weight of the composition). In some embodiments, the enzyme inactivation composition comprises citrate having a pH of about 1.5, $H_2O_2$ (about 0.5% by total weight of the composition), and $NaN_3$ (about 0.08% by total weight of the composition). In some embodiments, the enzyme inactivation composition comprises citrate having a pH of about 2.0, $H_2O_2$ (about 1% by total weight of the composition), and $NaN_3$ (about 0.08% by total weight of the composition). In some embodiments, the enzyme inactivation composition comprises citrate having a pH of about 1.5, $H_2O_2$ (about 1% by total weight of the composition), $NaN_3$ (about 0.08% by total weight of the composition), and sodium chloride (about 0.5M). In some embodiments, the enzyme inactivation composition comprises citrate having a pH of about 1.5, $H_2O_2$ (about 1% by total weight of the composition), $NaN_3$ (about 0.08% by total weight of the composition), and sodium chloride (about 0.75M). In some embodiments, the enzyme inactivation composition comprises citrate having a pH of about 1.5, $H_2O_2$ (about 1% by total weight of the composition), NaN$_3$ (about 0.08% by total weight of the composition), and sodium chloride (about 1M).

In another aspect of the present invention is a method of inactivating one or more enzymes in a biological sample comprising the steps of applying an enzyme inactivation composition to a biological sample, the biological sample comprising one or more reagent or endogenous enzymes, and wherein at least one of the enzyme inactivation composition or the biological sample is maintained at a temperature ranging from between about 25° C. to about 50° C. for a time period ranging from between about 4 minutes to about 16 minutes. In some embodiments, the enzyme inactivation composition comprises an acid, a peroxide, and a preservative. In some embodiments, the pH of the composition and/or the temperature and/or time in which the composition remains in contact with the sample is varied to effect enzyme inactivation. In some embodiments, the enzyme inactivation composition comprises a polycarboxylic acid having a pH ranging from about 1 to about 3; a peroxide; and a preservative; wherein the peroxide is present in an amount ranging from between about 0.25% to about 5% by total weight of the composition, and wherein the preservative is present in an amount ranging from between about 0.05% to about 1.0% by total weight of the composition. In some embodiments, the enzyme inactivation composition comprises a polycarboxylic acid having a pH ranging from about 1 to about 3; a peroxide; and a preservative; wherein the peroxide is present in an amount ranging from between about 0.25% to about 1.5% by total weight of the composition, and wherein the preservative is present in an amount ranging from between about 0.05% to about 1.0% by total weight of the composition. In some embodiments, the components of the enzyme inactivation composition are applied simultaneously to the sample. In other embodiments the components are applied sequentially to the sample and in any order. In some embodiments, the enzyme inactivation composition further comprises an elution mitigation agent (e.g. NaCl). In some embodiments, the final pH of a total fluid volume in contact with the biological sample (the "puddle") ranges from about 1.5 to about 3.0.

In other embodiments, the final pH of a total fluid volume in contact with the biological sample ranges from about 1.5 to about 2. In some embodiments, the biological sample is stained with a chromogenic substrate and wherein a detectable intensity and hue of the chromogenic substrate (e.g. from one or more detection kits applied during an upstream process) was determined to not be substantially reduced following application of an enzyme inactivation composition by pathological or qualified reader review. In some embodiments, the one or more enzymes are substantially inactivated or completely inactivated, as those terms are defined herein.

In some embodiments, the enzyme inactivation composition comprises a citrate having a pH of about 1.5, H$_2$O$_2$ (about 1% by total weight of the composition), and NaN$_3$ (about 0.08% by total weight of the composition) is applied to the biological sample, the biological sample comprising at least one of an endogenous peroxidase, a reagent peroxidase, or an alkaline phosphatase, and wherein the enzyme inactivation composition is maintained in communication with the biological sample for at least about 4 minutes, and wherein at least one of the composition, the biological sample, or other introduced components are heated to a temperature ranging from about 37° C. and about 41° C.

In some embodiments, the enzyme inactivation composition comprises a citrate having a pH of about 1.5, H$_2$O$_2$ (about 0.5% by total weight of the composition), and NaN$_3$ (about 0.08% by total weight of the composition) is applied to the biological sample, the biological sample comprising at least one of an endogenous peroxidase, a reagent peroxidase, or an alkaline phosphatase, and wherein the enzyme inactivation composition is maintained in communication with the biological sample for at least about 4 minutes, and wherein at least one of the composition, the biological sample, or other introduced components is heated to a temperature between about 37° C. and about 41° C.

In some embodiments, the enzyme inactivation composition comprises a citrate having a pH of about 2, H$_2$O$_2$ (about 1% by total weight of the composition), and NaN$_3$ (about 0.08% by total weight of the composition) is applied to the biological sample, the biological sample comprising at least one of an endogenous peroxidase, a reagent peroxidase, or an alkaline phosphatase, and wherein the enzyme inactivation composition is maintained in communication with the biological sample for at least about 4 minutes, and wherein at least one of the composition, the biological sample, or other introduced components is heated to a temperature between about 37° C. and about 41° C.

In some embodiments, the enzyme inactivation composition comprises a citrate having a pH of about 1.5, H$_2$O$_2$ (about 1% by total weight of the composition), NaN$_3$ (about 0.08% by total weight of the composition), and 0.5M sodium chloride is applied to the biological sample, the biological sample comprising at least one of an endogenous peroxidase, a reagent peroxidase, or an alkaline phosphatase, and wherein the enzyme inactivation composition is maintained in communication with the biological sample for at least about 4 minutes, and wherein at least one of the composition, the biological sample, or other introduced components is heated to a temperature of at least about 37° C.

In some embodiments, the enzyme inactivation composition comprises a citrate having a pH of about 1.5, H$_2$O$_2$ (about 1% by total weight of the composition), NaN$_3$ (about 0.08% by total weight of the composition), and 0.75M sodium chloride is applied to the biological sample, the biological sample comprising at least one of an endogenous peroxidase, a reagent peroxidase, or an alkaline phosphatase, and wherein the enzyme inactivation composition is maintained in communication with the biological sample for at least about 4 minutes, and wherein at least one of the composition, the biological sample, or other introduced components is heated to a temperature of at least about 37° C.

In some embodiments, the enzyme inactivation composition comprises a citrate having a pH of about 1.5, H$_2$O$_2$ (about 1% by total weight of the composition), NaN$_3$ (about 0.08% by total weight of the composition), and 1M sodium chloride is applied to the biological sample, the biological sample comprising at least one of an endogenous peroxidase, a reagent peroxidase, or an alkaline phosphatase, and wherein the enzyme inactivation composition is maintained in communication with the biological sample for at least about 4 minutes, and wherein at least one of the composition, the biological sample, or other introduced components is heated to a temperature of at least about 37° C.

In another aspect of the present invention is a method of detecting multiple targets in a biological sample, comprising: (a) contacting the biological sample with a first chromogenic detection reagent having a first enzyme; (b) detecting a first signal from the first chromogenic detection reagent; and (c) inactivating the first enzyme by applying a first enzyme inactivation composition, the composition comprising a polycarboxylic acid having a pH ranging from about 1 to about 5; a peroxide; and a preservative; wherein the peroxide is present in an amount ranging from between about 0.25% to about 1.5% by total weight of the composition, and wherein the preservative is present in an amount ranging from between about 0.05% to about 1.0% by total weight of the composition, wherein at least one of the first enzyme inactivation composition or the biological sample is maintained at a temperature ranging from between about 25° C. to about 50° C. for a time period ranging from between about 4 minutes to about 16 minutes. In some embodiments, the method further comprises the steps of (d) contacting the biological sample with a second chromogenic detection reagent having a second enzyme; (e) detecting a second signal from the second chromogenic detection reagent; and (f) inactivating the second enzyme by applying a second enzyme inactivation composition, the composition comprising a polycarboxylic acid having a pH ranging from about 1 to about 5; a peroxide; and a preservative; wherein the peroxide is present in an amount ranging from between about 0.25% to about 1.5% by total weight of the composition, and wherein the preservative is present in an amount ranging from between about 0.05% to about 1.0% by total weight of the composition; wherein at least one of the second enzyme inactivation composition or the biological sample is maintained at a temperature ranging from between about 25° C. to about 50° C. for a time period ranging from between about 4 minutes to about 16 minutes. In some embodiments, the steps are repeated for detecting additional chromogenic detection regents, such as third, fourth, and fifth (and nth) chromogenic detection reagents. In some embodiments, the one or more enzymes are substantially inactivated or completely inactivated. In some embodiments, the biological sample is stained with one or more chromogenic substrates such that a detectable intensity or hue of the chromogenic substrate was determined to not be substantially reduced following application of an enzyme inactivation composition by pathological or qualified reader review. In some embodiments, the biological samples are pre-treated with an enzyme inactivation composition to substantially or completely inactivate endogenous peroxidase activity.

In another aspect of the present invention is a method of preparing a biological sample for the detection of at least a second target comprising contacting a biological sample having at least one of an endogenous peroxidase, a reagent peroxidase, or a alkaline phosphatase with a first enzyme inactivation composition, the first enzyme inactivation composition comprising a polycarboxylic acid having a pH ranging from about 1 to about 5; a peroxide; and a preservative; wherein the peroxide is present in an amount ranging from between about 0.25% to about 1.5% by total weight of the composition, and wherein the preservative is present in an amount ranging from between about 0.05% to about 1.0% by total weight of the composition; and sequentially introducing components to detect at least the second target. In some embodiments, at least one of the sample and/or the enzyme inactivation composition are maintained at a temperature ranging from about 25° C. to about 50° C. for a time period ranging from between about 4 minutes to about 16 minutes. In other embodiments, at least one of the sample and/or the enzyme inactivation composition are maintained at a temperature ranging from about 37° C. to about 50° C. for a time period ranging from between about 4 minutes to about 16 minutes.

In another aspect of the present invention is a biological sample comprising one or more enzymes that are either substantially inactivated or completely inactivated, the biological sample prepared by applying an enzyme inactivation composition for between about 4 minutes and about 8 minutes at a temperature ranging from between about 25° C. and about 41° C., wherein the enzyme inactivation composition is selected from the group consisting of a composition comprising (i) citrate having a pH of about 1.5, $H_2O_2$ (about 1% by total weight of the composition), and $NaN_3$ (about 0.08% by total weight of the composition); (ii) citrate having a pH of about 1.5, $H_2O_2$ (about 0.5% by total weight of the composition), and $NaN_3$ (about 0.08% by total weight of the composition); (iii) citrate having a pH of about 2.0, $H_2O_2$ (about 1% by total weight of the composition), and $NaN_3$ (about 0.08% by total weight of the composition); (iv) citrate having a pH of about 1.5, $H_2O_2$ (about 1% by total weight of the composition), $NaN_3$ (about 0.08% by total weight of the composition), and sodium chloride (about 0.5M); (v) citrate having a pH of about 1.5, $H_2O_2$ (about 1% by total weight of the composition), $NaN_3$ (about 0.08% by total weight of the composition), and sodium chloride (about 0.75M); (vi) citrate having a pH of about 1.5, $H_2O_2$ (about 1% by total weight of the composition), $NaN_3$ (about 0.08% by total weight of the composition), and sodium chloride (about 1M). In some embodiments, the biological sample is treated with a chromogenic detection reagent in an upstream process, where the chromogenic detection reagent comprises an enzyme (e.g. a peroxidase and/or an alkaline phosphatase).

In another aspect of the present invention is a kit comprising a first component comprising a polycarboxylic acid having a pH ranging from about 1 to about 5; a peroxide; and a preservative; wherein the peroxide is present in an amount ranging from between about 0.25% to about 1.5% by total weight of the composition, and wherein the preservative is present in an amount ranging from between about 0.05% to about 1.0% by total weight of the composition; and a second component comprising an elution mitigation agent. In some embodiments, the elution mitigation agent is a salt (e.g. NaCl).

There remains a need for enzyme inactivation compositions and methods of applying those compositions to biological samples that allow for reagent and/or endogenous enzymes within the sample to be at least substantially inactivated, and to do so in a suitable amount of time and without substantially affecting tissue antigen detection signal intensity, tissue morphology, chromogen stability, and counterstain appearance.

Applicants have developed the disclosed enzyme inactivation compositions and methods of applying those compositions to biological samples where the compositions and methods allow for any reagent and/or endogenous enzymes present therein to be substantially inactivated or completely inactivated, as those terms are defined herein. In fact, Applicants have shown that the compositions and methods allow for enzyme inactivation to occur under conditions that, as compared with prior art methods, are not harsh, i.e. the methods of applying the compositions herein do not require the application of temperatures in excess of 50° C. for extended periods of time. Again, in contrast to the prior art methods of enzyme inactivation, the compositions and methods disclosed herein are comparatively superior and allow for irreversible enzyme inactivation in a short amount of time (e.g. 4 to 8 minutes) and without complete elution of the detection kit(s), and this is especially important in the context of multiplexed assays. Moreover, Applicants have shown that the compositions and methods allow for enzyme inactivation without substantially negatively affecting tissue antigen detection signal intensity, tissue morphology, chromogen stability, and counterstain appearance, as demonstrated in the examples provided herein. Indeed, it has been shown that the compositions and methods provided herein do not negatively impact any downstream processing steps.

BRIEF DESCRIPTION OF THE FIGURES

The patent or application file contains at least one drawing executed in color. Copies of this patent or patent application publication with color drawings will be provided to the Office upon request and the payment of the necessary fee.

FIG. 1A depicts a standard tissue sample with no treatment—CD20, tonsil (8 min CC1, 16 min CD20), where the images were captured at 20× magnification.

FIG. 1B depicts a standard tissue sample with no treatment—CD20, tonsil (8 min CC1, 16 min CD20), where the images were captured at 20× magnification.

FIG. 1C depicts an IHC DAB Standard with no treatment—CD20, tonsil (8 min CC1, 16 min CD20).

FIG. 1D depicts a tissue sample treated with Composition A (see Table 1).

FIG. 1E depicts a tissue sample treated with Composition A (see Table 1).

FIG. 1F depicts a tissue sample treated with composition B (see Table 1).

FIG. 1G depicts a tissue sample treated with composition B (see Table 1).

FIG. 1H depicts a tissue sample treated with Composition C (see Table 1).

FIG. 1AA depicts a tissue sample treated with Composition N (see Table 1).

FIG. 1BB depicts a tissue sample treated with Composition N (see Table 1).

FIG. 1CC depicts a tissue sample treated with Composition O (see Table 1).

FIG. 1DD depicts a tissue sample treated with Composition O (see Table 1).

FIG. 1EE depicts a tissue sample treated with Composition P (see Table 1).

FIG. 1FF depicts a tissue sample treated with Composition P (see Table 1).

FIG. 1GG depicts a tissue samples treated with Composition Q (see Table 1).

FIG. 1HH depicts a tissue samples treated with Composition Q (see Table 1).

FIG. 2A depicts an IHC AP Red Standard with no treatment—CD20, tonsil (8 min CC1, 16 min CD20) (Representative images at 10×).

FIG. 2S depicts a tissue sample treated with Composition Q (see Table 2).

FIG. 3A depicts tissue stained with IHC DAB Standard with no treatment; CD20, tonsil (8 min CC1, 16 min CD20).

FIG. 2H depicts a tissue sample treated with Composition C (see Table 3).

FIG. 3V depicts a tissue sample treated with Composition Q (see Table 3).

FIG. 4A depicts tissue stained with IHC DAB Standard with no treatment—bcl2, tonsil (64 min CC1, 32 min bcl2).

FIG. 4B depicts tissue stained with IHC DAB Standard with no treatment—bcl2, tonsil (64 min CC1, 32 min bcl2).

FIG. 4C depicts a tissue sample treated with Composition A.

FIG. 4D depicts a tissue sample treated with Composition A.

FIG. 4E depicts a tissue sample treated with Composition B.

FIG. 4F depicts a tissue sample treated with Composition B.

FIG. 4G depicts a tissue sample treated with Composition C.

FIG. 4H depicts a tissue sample treated with Composition C.

FIG. 4AA depicts a tissue sample treated with Composition N.

FIG. 4BB depicts a tissue sample treated with Composition N.

FIG. 4CC depicts a tissue sample treated with Composition O.

FIG. 4DD depicts a tissue sample treated with Composition O.

FIG. 4EE depicts a tissue sample treated with Composition P.

FIG. 4FF depicts a tissue sample treated with Composition P.

FIG. 4GG depicts a tissue sample treated with Composition Q.

FIG. 4HH depicts a tissue sample treated with Composition Q.

FIG. 5E depicts a tissue sample treated with Composition B.

FIG. 5F depicts a tissue sample treated with Composition B.

FIG. 5G depicts a tissue sample treated with Composition C.

FIG. 5H depicts a tissue sample treated with Composition C.

FIG. 5I depicts a tissue sample treated with Composition D.

FIG. 5J depicts a tissue sample treated with Composition D.

FIG. 5K depicts a tissue sample treated with Composition E.

FIG. 5L depicts a tissue sample treated with Composition E.

FIG. 5M depicts a tissue sample treated with Composition F.

FIG. 5N depicts a tissue sample treated with Composition F.

FIG. 5O depicts a tissue sample treated with Composition G.

FIG. 5P depicts a tissue sample treated with Composition G.

Figure 5A:
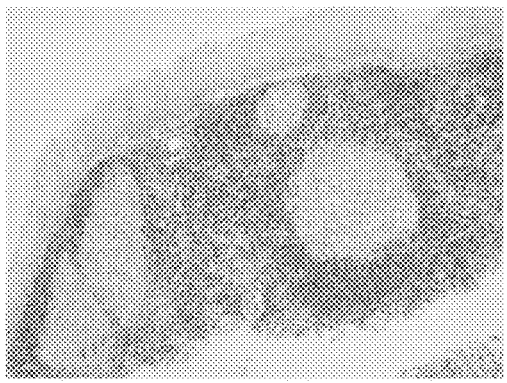
FIG. 5A depicts tissue stained with IHC DAB Standard with no treatment—bcl2, tonsil (64 min CC1, 32 min bcl2).
Figure 5B:
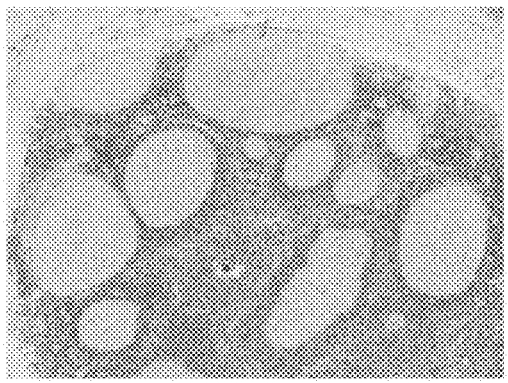
FIG. 5B depicts tissue stained with IHC DAB Standard with no treatment—bcl2, tonsil (64 min CC1, 32 min bcl2).
Figure 5C:
FIG. 5C depicts a tissue sample treated with Compositions A.
Figure 5D:
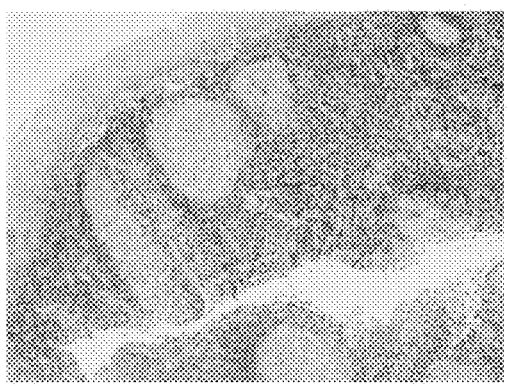
FIG. 5D depicts a tissue sample treated with Compositions A.
Figure 5E:
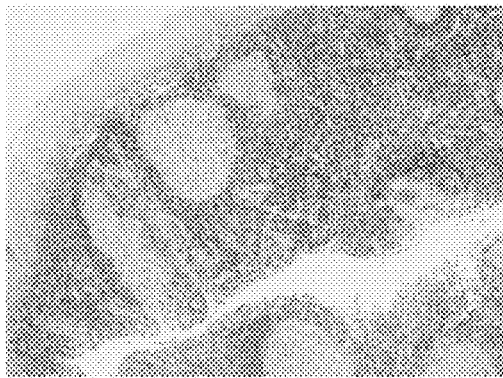
FIGS. 5 through 5HH set forth a sequence of images that show the impact of different enzyme inactivation compositions and methods on tissue antigen detection signal intensity (BLC2) after application to a biological sample.
Figure 5F:
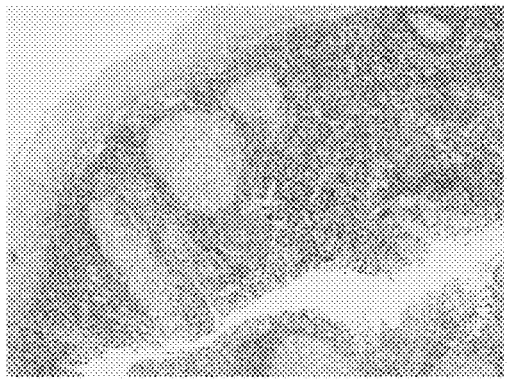
Figure 5G:
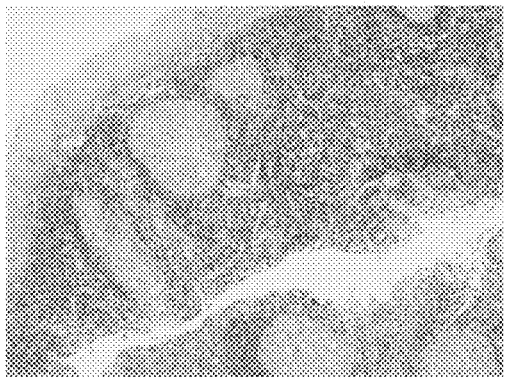
Figure 5H:
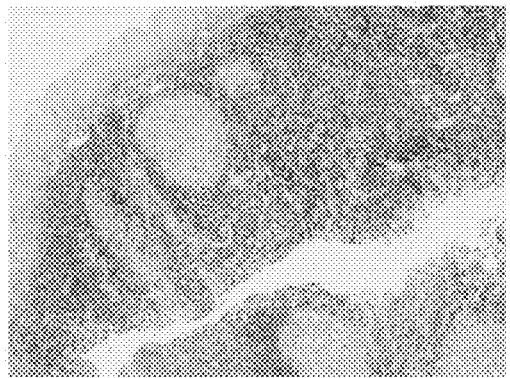
Figure 5I:
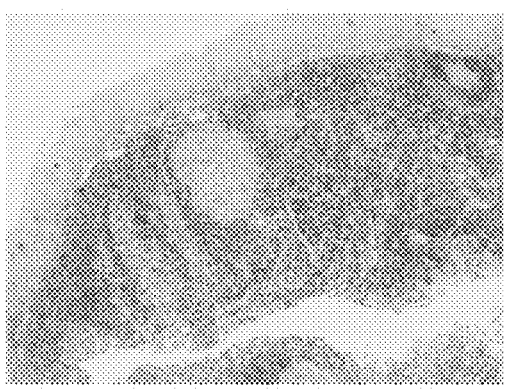
Figure 5J:
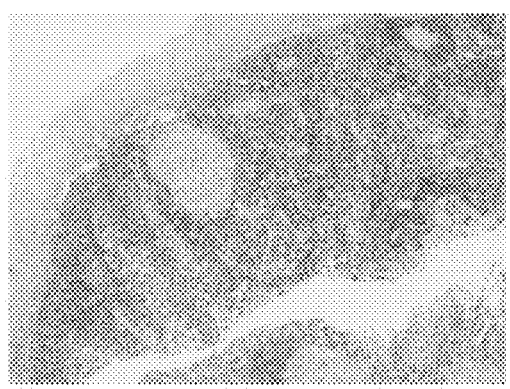
Figure 5K:
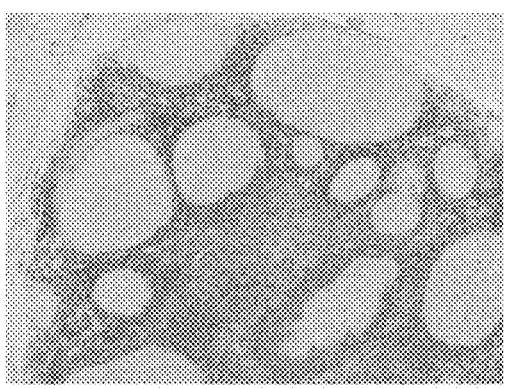
Figure 5L:
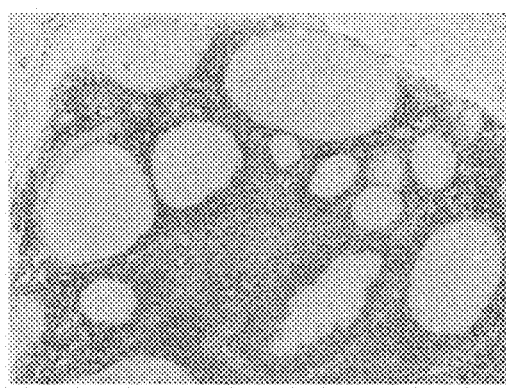
Figure 5M:
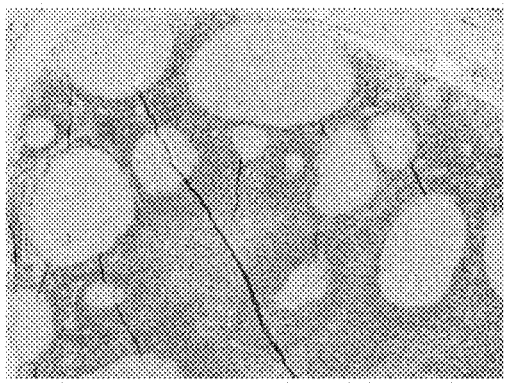
Figure 5N:
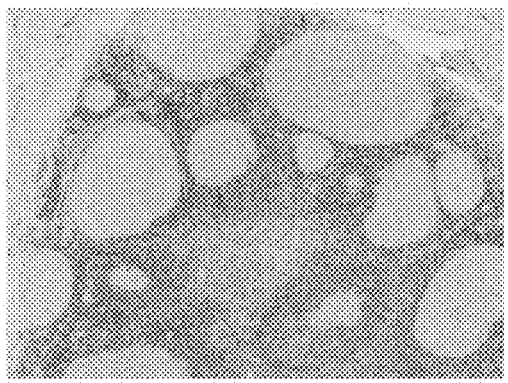
Figure 5O:
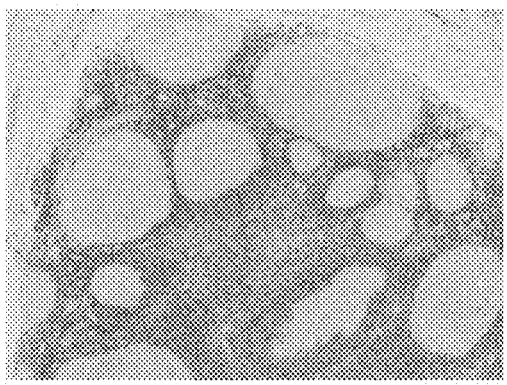
Figure 5P:
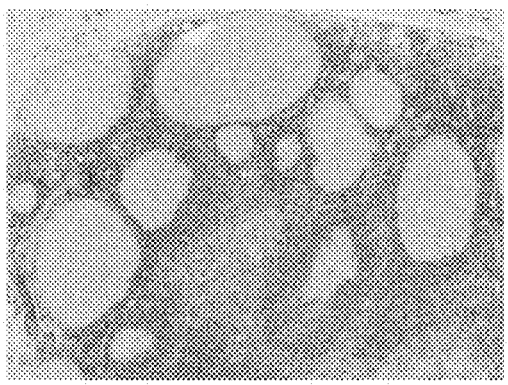
Figure 5Q:
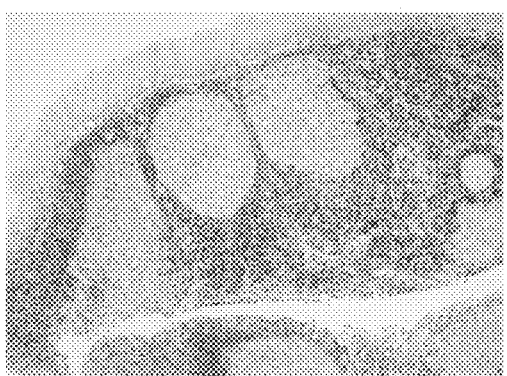

FIG. 5Q depicts a tissue sample treated with Composition H.

Figure 5R:
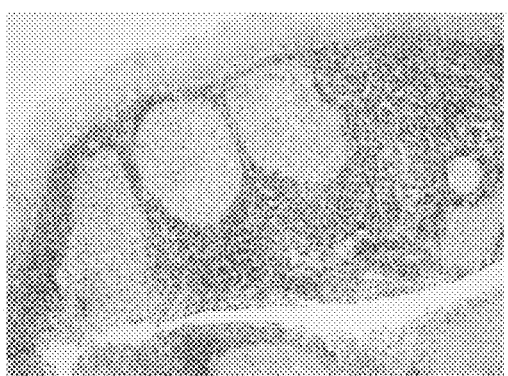

FIG. 5R depicts a tissue sample treated with Composition H.

Figure 5S:
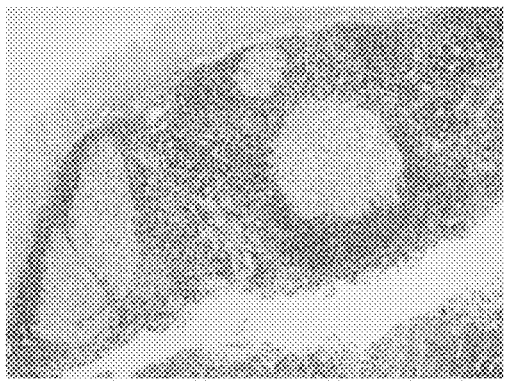

FIG. 5S depicts a tissue sample treated with Composition J.

Figure 5T:
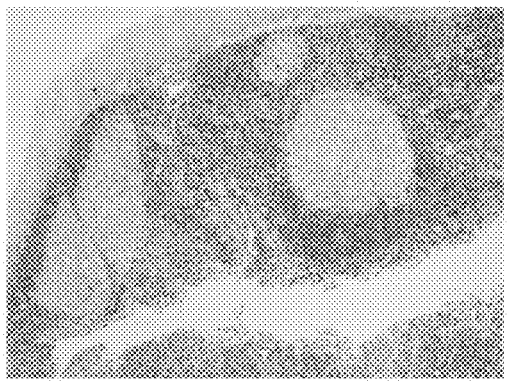

FIG. 5T depicts a tissue sample treated with Composition J.

Figure 5U:
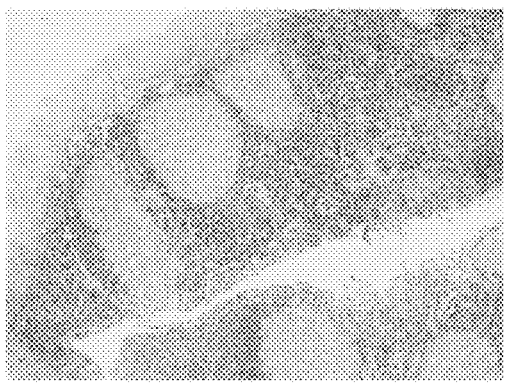

FIG. 5U depicts a tissue sample treated with Composition K.

Figure 5V:
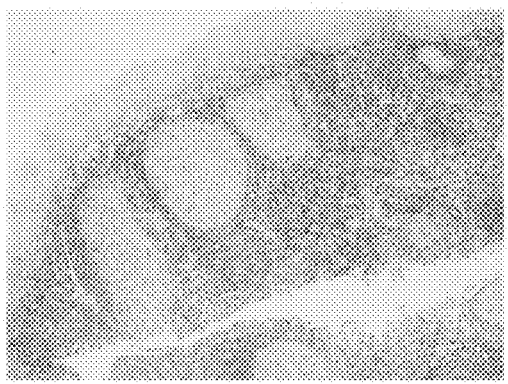

FIG. 5V depicts a tissue sample treated with Composition K.

Figure 5W:
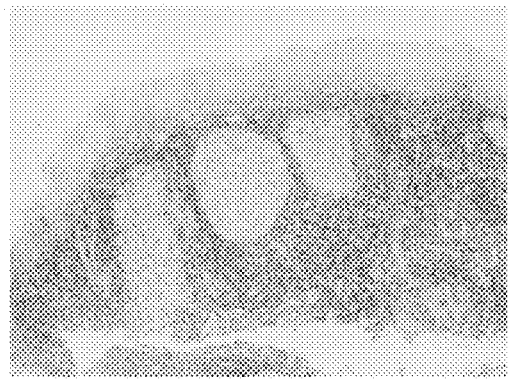

FIG. 5W depicts a tissue sample treated with Composition L.

Figure 5X:
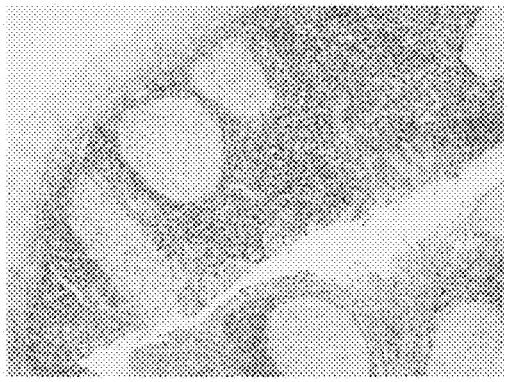

FIG. 5X depicts a tissue sample treated with Composition L.

Figure 5Y:
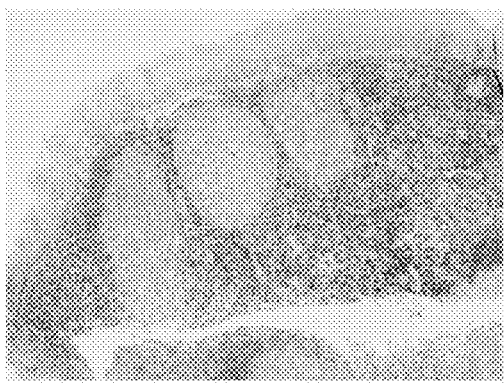

FIG. 5Y depicts a tissue sample treated with Composition M.

Figure 5Z:
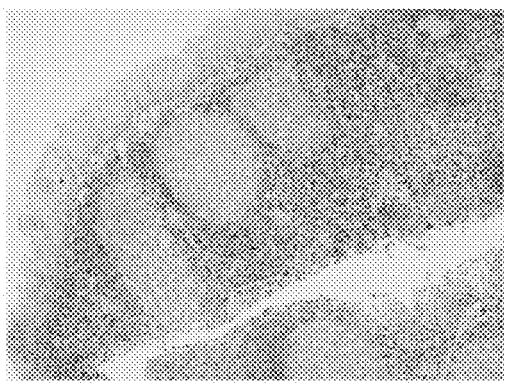
Figure 5A:
Figure 5B:
Figure 5C:
Figure 5D:
Figure 5E:
Figure 5F:
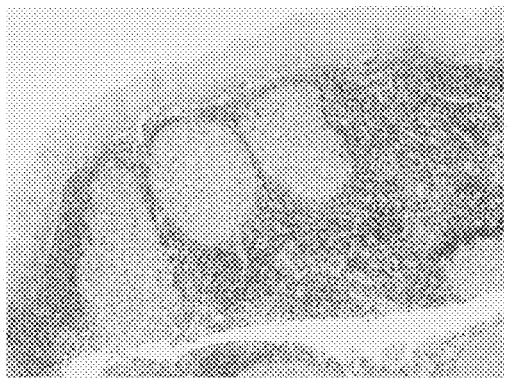
Figure 5G:
Figure 5H:
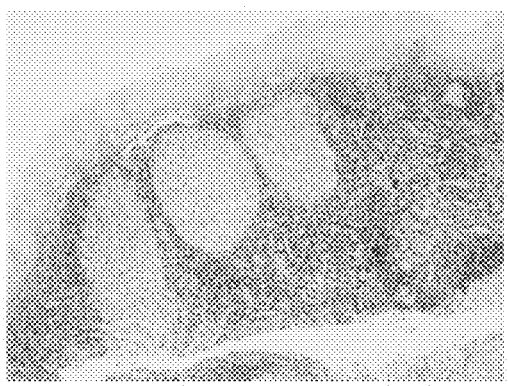

FIG. 5Z depicts a tissue sample treated with Composition M.

FIG. 5AA depicts a tissue sample treated with Composition N.

FIG. 5BB depicts a tissue sample treated with Composition N.

FIG. 5CC depicts a tissue sample treated with Composition O.

FIG. 5DD depicts a tissue sample treated with Composition O.

FIG. 5EE depicts a tissue sample treated with Composition P.

FIG. 5FF depicts a tissue sample treated with Composition P.

FIG. 5GG depicts a tissue sample treated with Composition Q.

FIG. 5HH depicts a tissue sample treated with Composition Q.

Figure 6A:
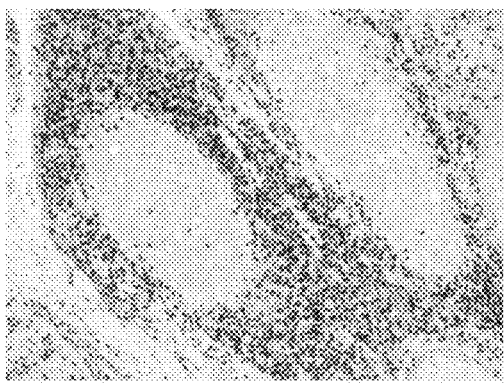
Figure 6B:
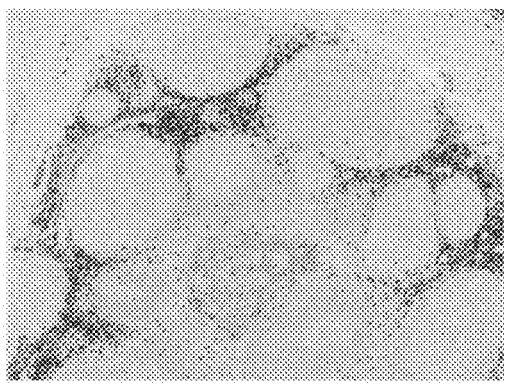
Figure 6C:
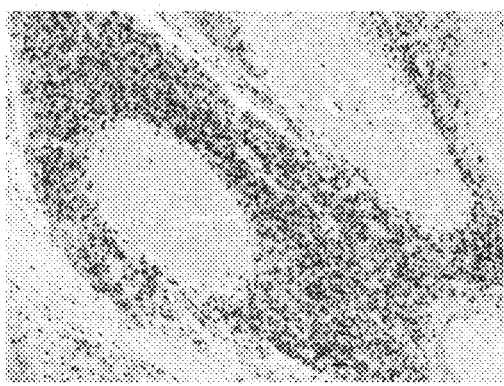
Figure 6D:
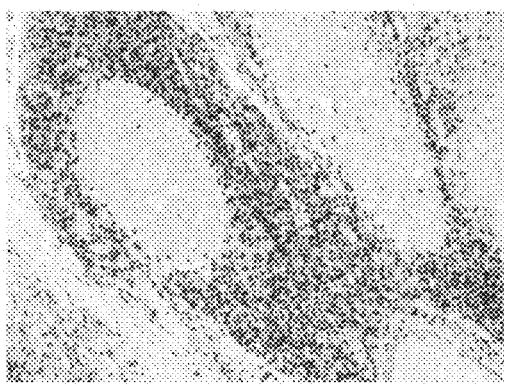
Figure 6E:
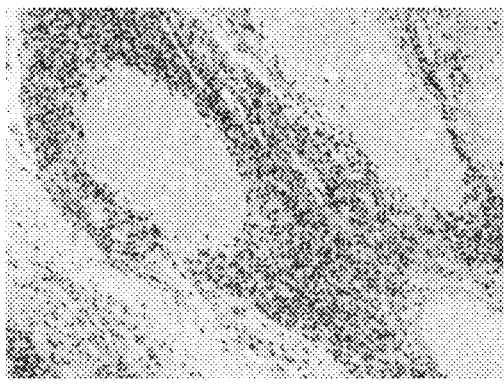
Figure 6F:
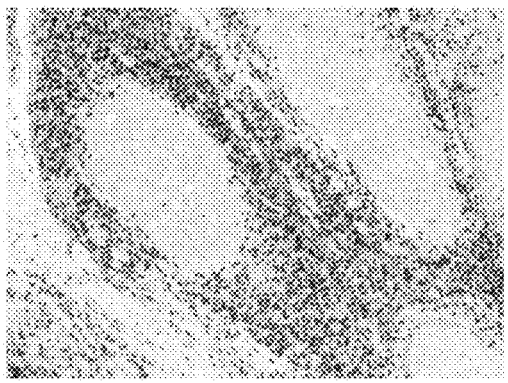
Figure 6G:
Figure 6H:
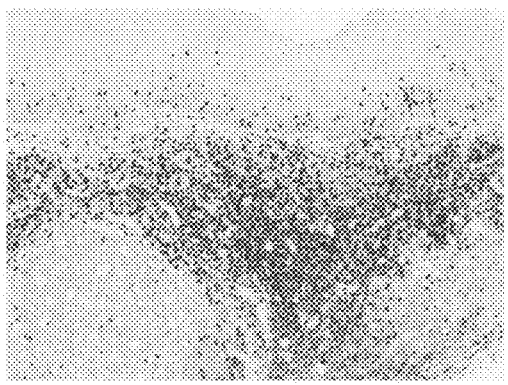

FIGS. 6 through 6HH set forth a sequence of images that show the impact of different enzyme inactivation compositions and methods on tissue antigen detection signal intensity (CD8) after application to a biological sample.

FIG. 6A depicts a tissue stained with IHC DAB Standard No. 1 with no treatment—CD8, tonsil (64 min CC1, 16 min CD8).

FIG. 6B depicts a tissue stained with IHC DAB Standard No. 1 with no treatment—CD8, tonsil (64 min CC1, 16 min CD8).

FIG. 6C depicts tissue samples treated with Compositions A.

FIG. 6D depicts tissue samples treated with Compositions A.

FIG. 6E depicts a tissue sample treated with Composition B.

FIG. 6F depicts a tissue sample treated with Composition B.

FIG. 6G depicts a tissue sample treated with Composition C.

FIG. 6H depicts a tissue sample treated with Composition C.

Figure 6I:

FIG. 6I depicts a tissue sample treated with Composition D.

Figure 6J:
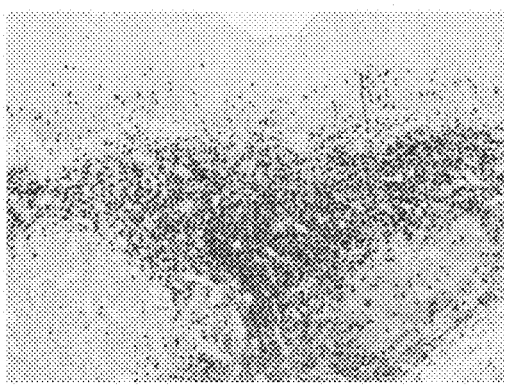

FIG. 6J depicts a tissue sample treated with Composition D.

Figure 6K:
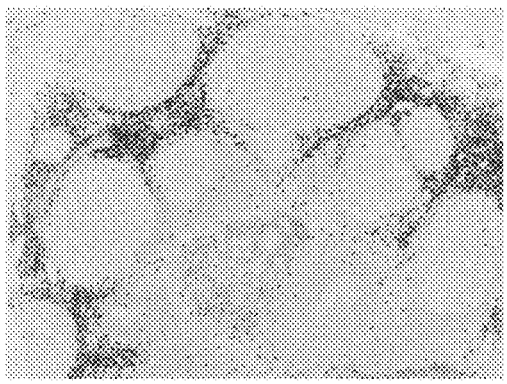

FIG. 6K depicts a tissue sample treated with Composition E.

Figure 6L:
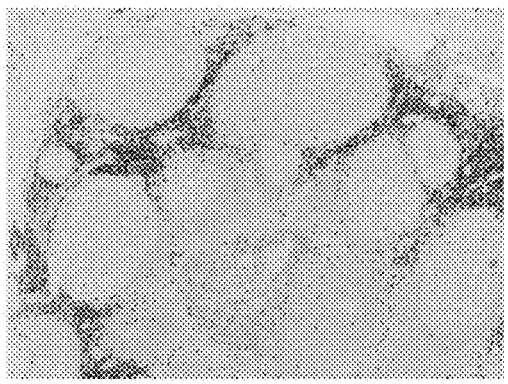

FIG. 6L depicts a tissue sample treated with Composition E.

Figure 6M:
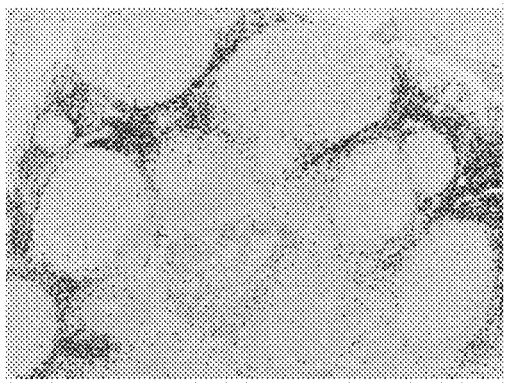

FIG. 6M depicts a tissue sample treated with Composition F.

Figure 6N:
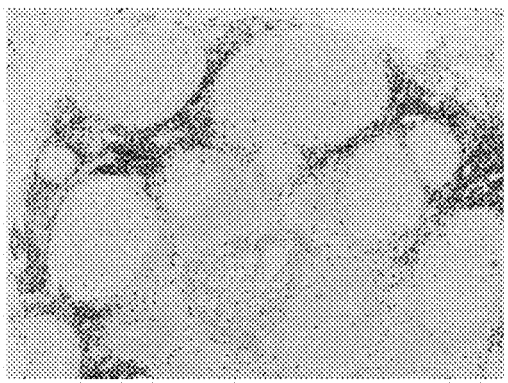

FIG. 6N depicts a tissue sample treated with Composition F.

Figure 6O:
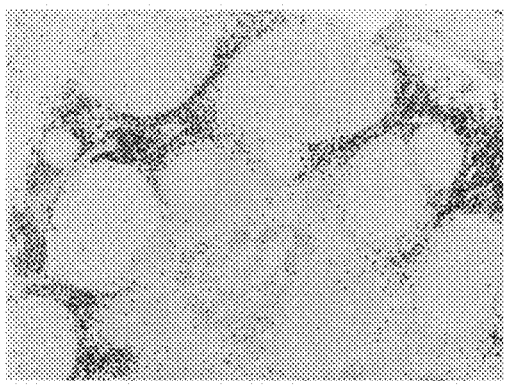

FIG. 6O depicts a tissue sample treated with Composition G.

Figure 6P:
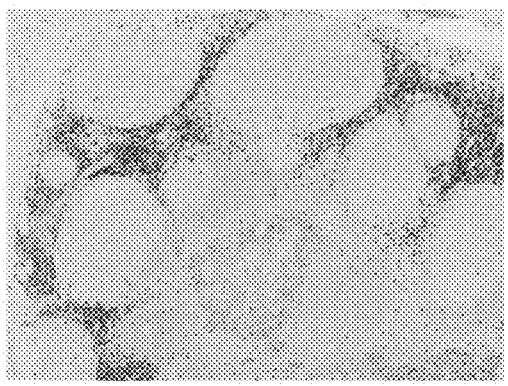

FIG. 6P depicts a tissue sample treated with Composition G.

Figure 6Q:
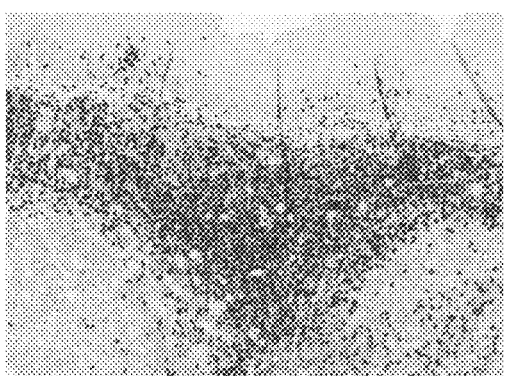

FIG. 6Q depicts a tissue sample treated with Composition H.

Figure 6R:
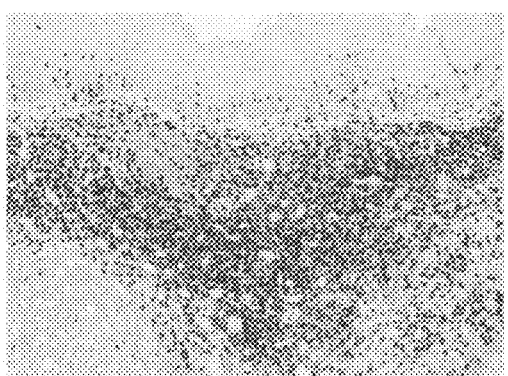

FIG. 6R depicts a tissue sample treated with Composition H.

Figure 6S:
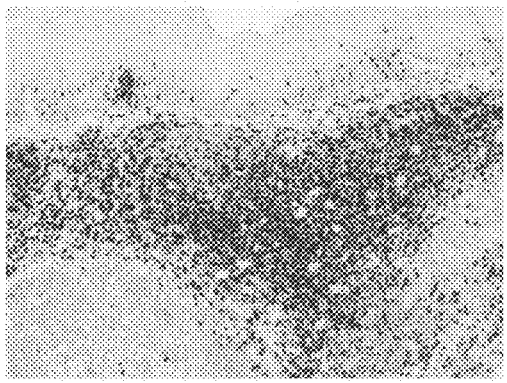

FIG. 6S depicts a tissue sample treated with Composition J.

Figure 6T:
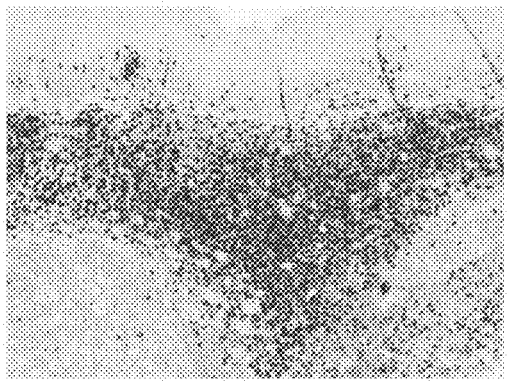

FIG. 6T depicts a tissue sample treated with Composition J.

Figure 6U:
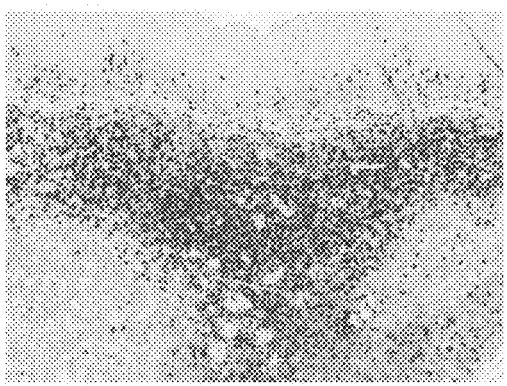

FIG. 6U depicts a tissue sample treated with Composition K.

Figure 6V:
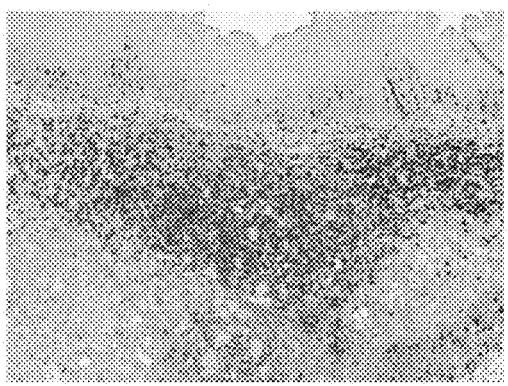

FIG. 6V depicts a tissue sample treated with Composition K.

Figure 6W:
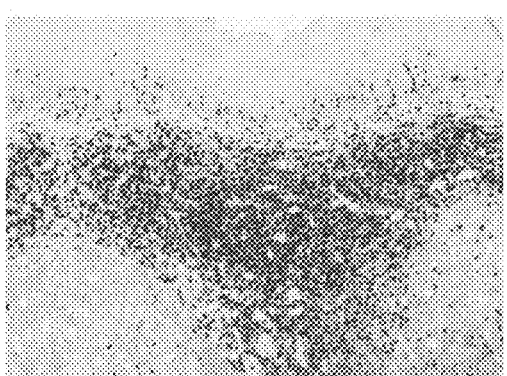

FIG. 6W depicts a tissue sample treated with Composition L.

Figure 6X:
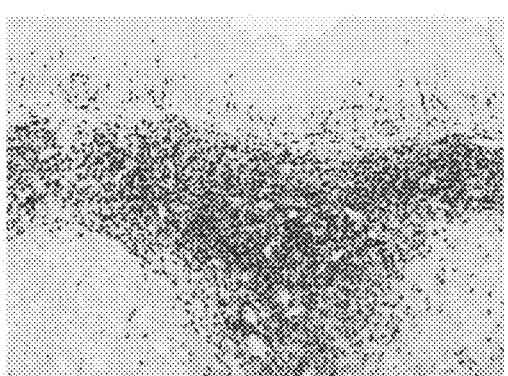

FIG. 6X depicts a tissue sample treated with Composition L.

Figure 6Y:
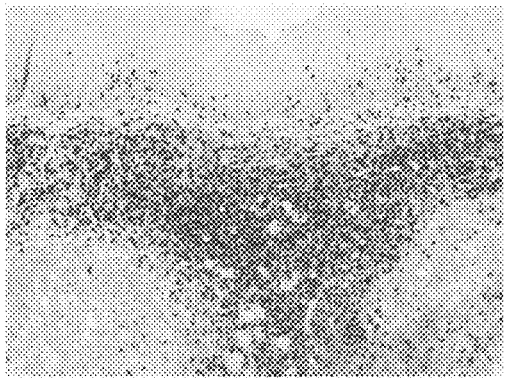

FIG. 6Y depicts a tissue sample treated with Composition M.

Figure 6Z:
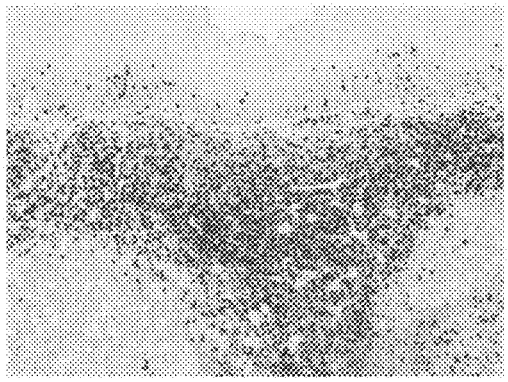
Figure 6A:
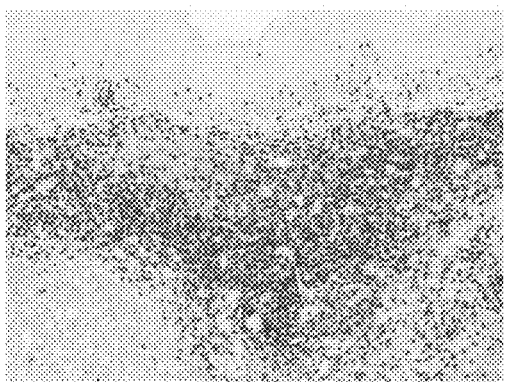
Figure 6B:
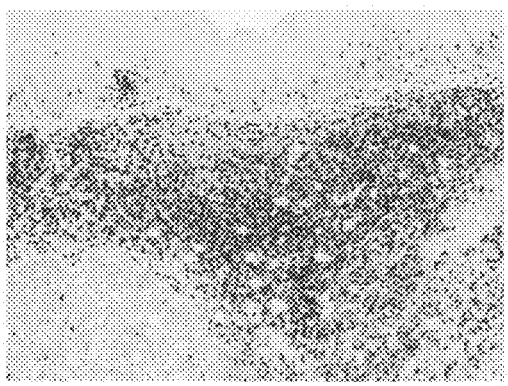
Figure 6C:
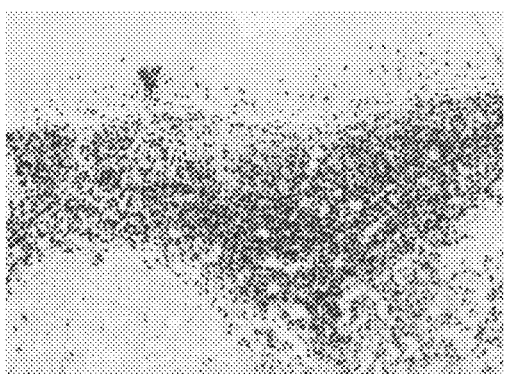
Figure 6D:
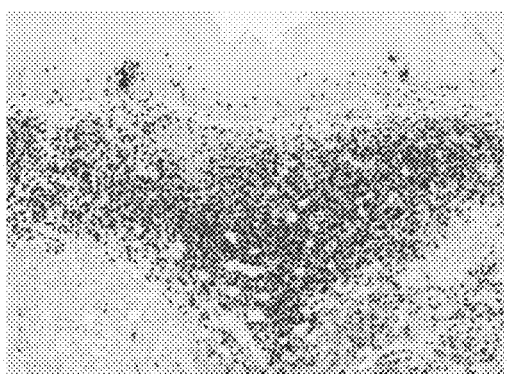
Figure 6E:
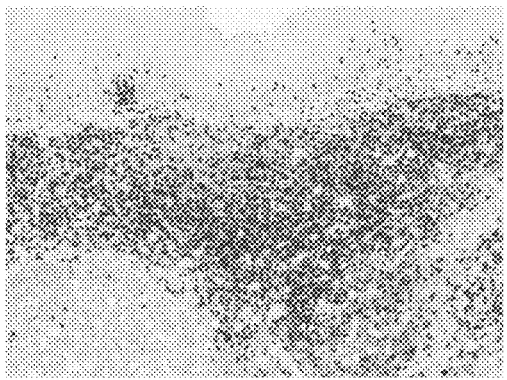
Figure 6F:
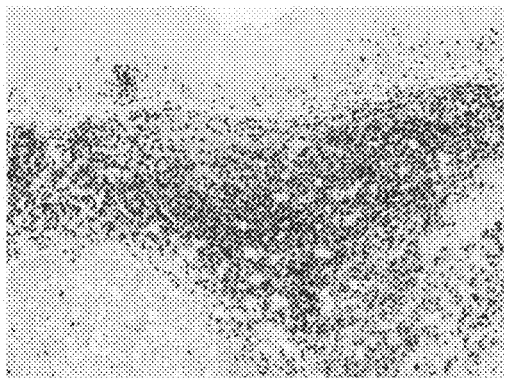
Figure 6G:
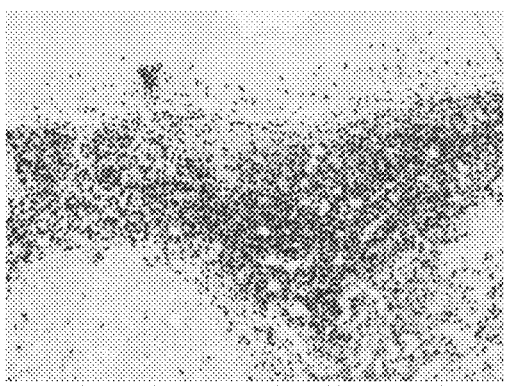
Figure 6H:
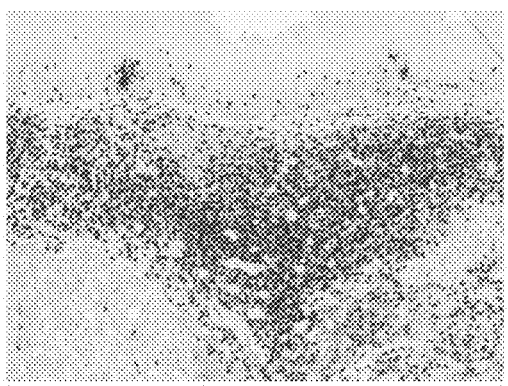

FIG. 6Z depicts a tissue sample treated with Composition M.

FIG. 6AA depicts a tissue sample treated with Composition N.

FIG. 6BB depicts a tissue sample treated with Composition N.

FIG. 6CC depicts a tissue sample treated with Composition O.

FIG. 6DD depicts a tissue sample treated with Composition O.

FIG. 6EE depicts a tissue sample treated with Composition P.

FIG. 6FF depicts a tissue sample treated with Composition P.

FIG. 6GG depicts a tissue sample treated with Composition Q.

FIG. 6HH depicts a tissue sample treated with Composition Q.

Figure 7A:
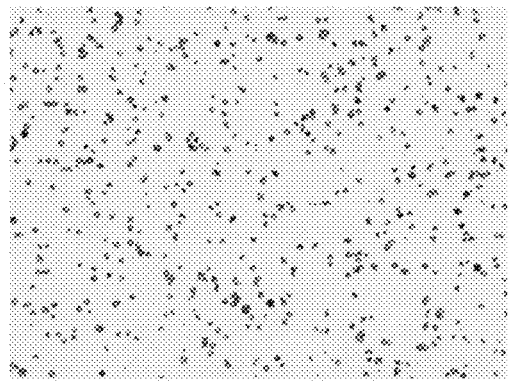
Figure 7B:
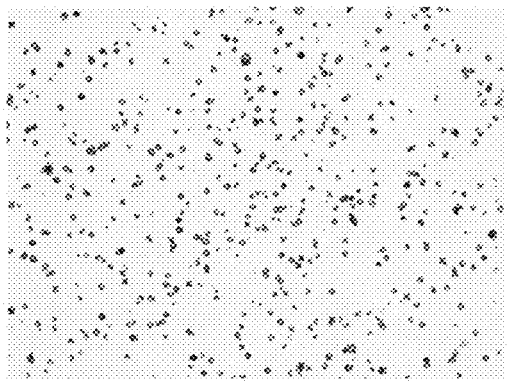
Figure 7C:
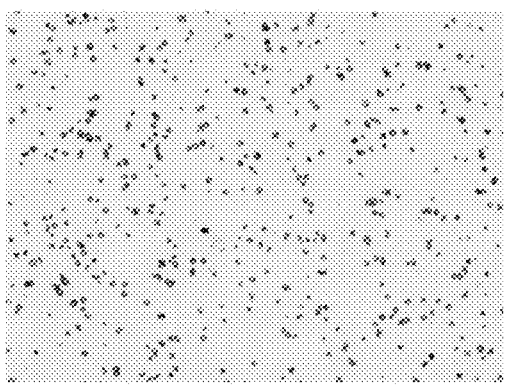
Figure 7D:
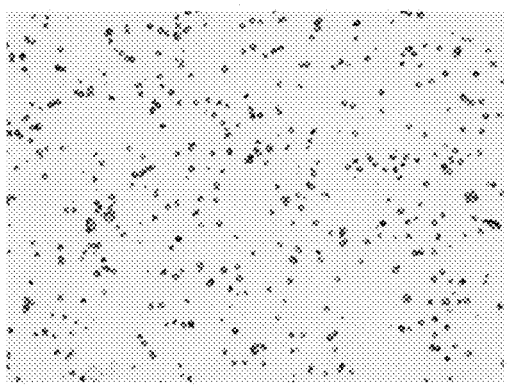
Figure 7E:
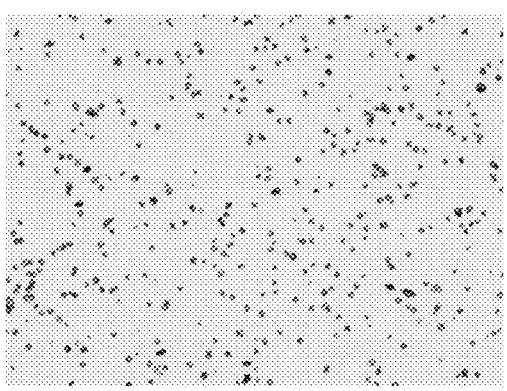
Figure 7F:
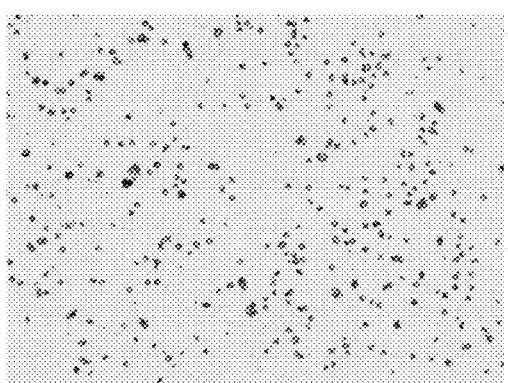
Figure 7G:
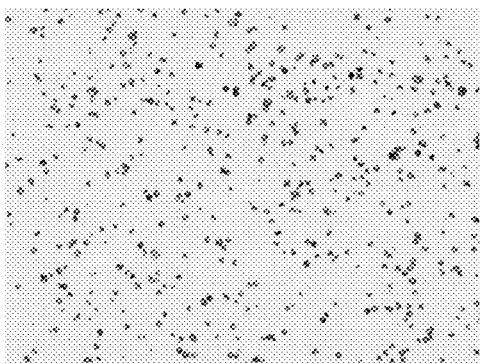
Figure 7H:
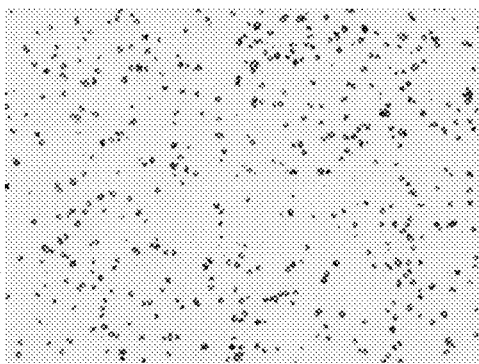

FIGS. 7 through 7HH set forth a sequence of images that show the impact of different enzyme inactivation compositions and methods on tissue antigen detection signal intensity (HER2) after application to a biological sample.

FIG. 7A depicts tissue stained with IHC DAB Standard with no treatment—HER2, VMSI Pathway™ HER2 4-in-1 test slides (32 min CC1, 32 min HER2).

FIG. 7B depicts tissue stained with IHC DAB Standard with no treatment—HER2, VMSI Pathway™ HER2 4-in-1 test slides (32 min CC1, 32 min HER2).

FIG. 7C depicts tissue samples treated with Compositions A.

FIG. 7D depicts tissue samples treated with Compositions A.

FIG. 7E depicts a tissue sample treated with Composition B.

FIG. 7F depicts a tissue sample treated with Composition B.

FIG. 7G depicts a tissue sample treated with Composition C.

FIG. 7H depicts a tissue sample treated with Composition C.

Figure 7I:
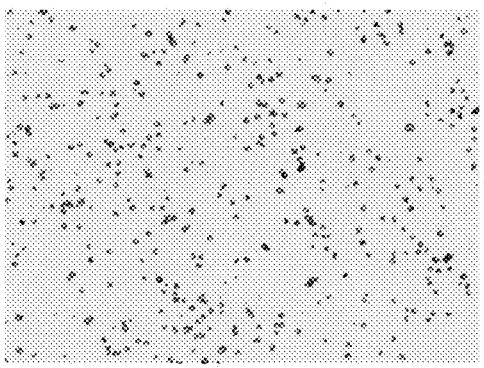

FIG. 7I depicts a tissue sample treated with Composition D.

Figure 7J:
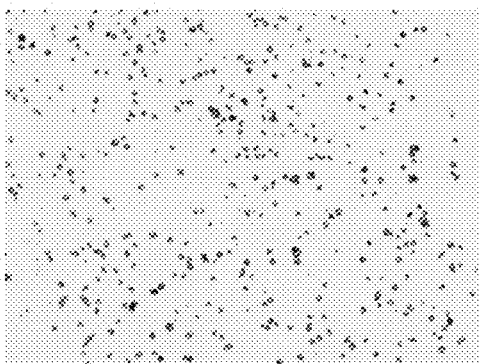

FIG. 7J depicts a tissue sample treated with Composition D.

Figure 7K:
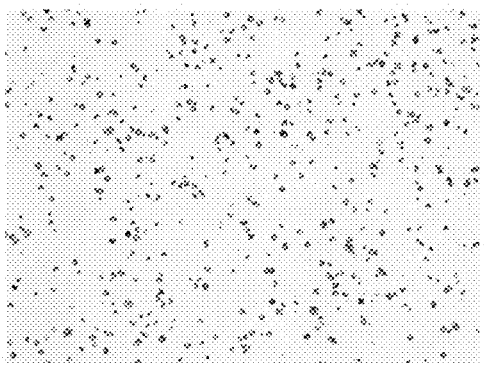

FIG. 7K depicts a tissue sample treated with Composition E.

Figure 7L:
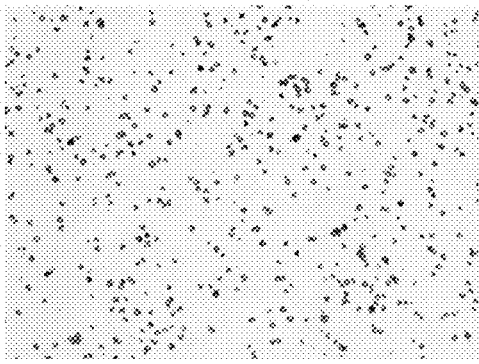

FIG. 7L depicts a tissue sample treated with Composition E.

Figure 7M:
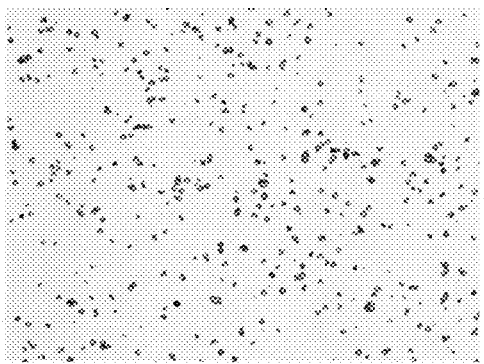

FIG. 7M depicts a tissue sample treated with Composition F.

Figure 7N:
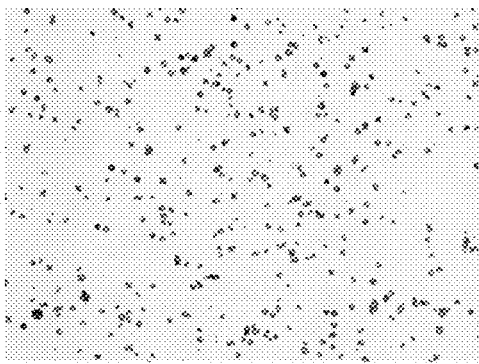

FIG. 7N depicts a tissue sample treated with Composition F.

Figure 7O:
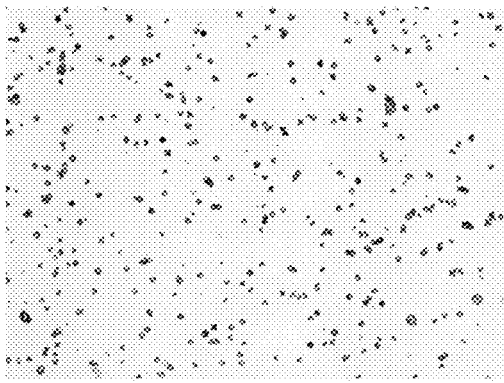

FIG. 7O depicts a tissue sample treated with Composition G.

Figure 7P:
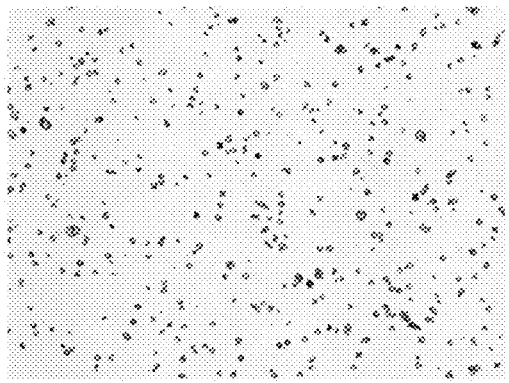

FIG. 7P depicts a tissue sample treated with Composition G.

Figure 7Q:
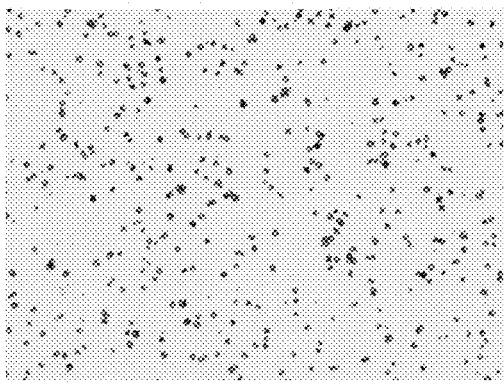

FIG. 7Q depicts a tissue sample treated with Composition H.

Figure 7R:
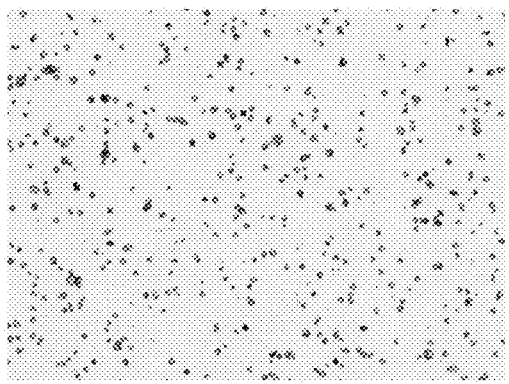

FIG. 7R depicts a tissue sample treated with Composition H.

Figure 7S:
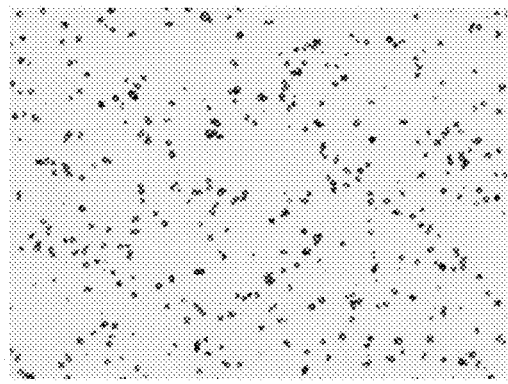

FIG. 7S depicts a tissue sample treated with Composition J.

Figure 7T:
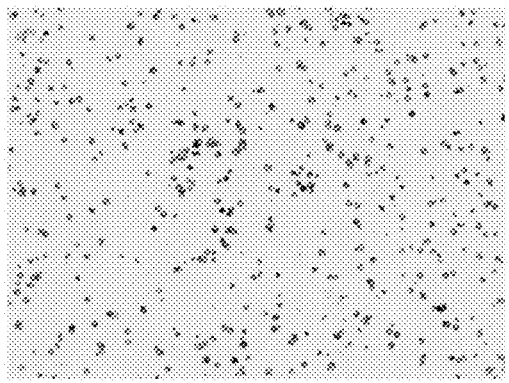

FIG. 7T depicts a tissue sample treated with Composition J.

Figure 7U:
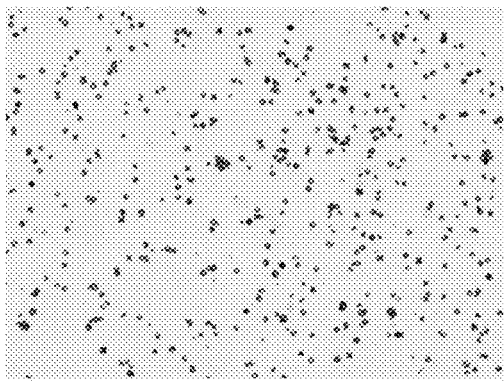

FIG. 7U depicts a tissue sample treated with Composition K.

Figure 7V:
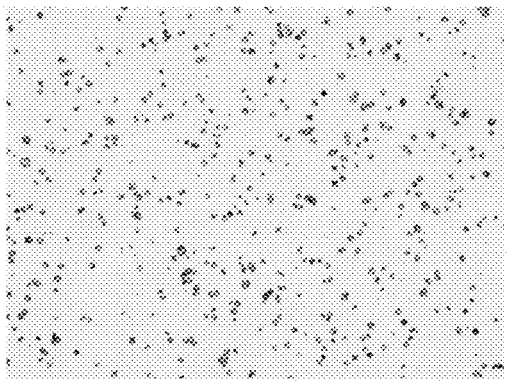

FIG. 7V depicts a tissue sample treated with Composition K.

Figure 7W:
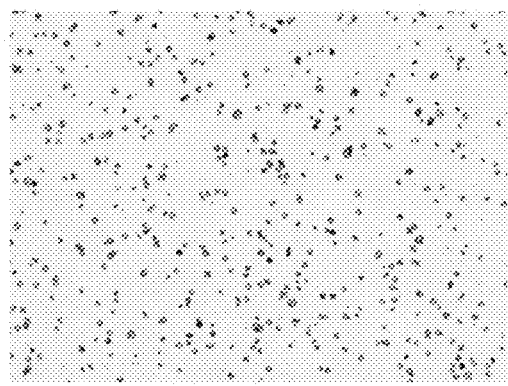

FIG. 7W depicts a tissue sample treated with Composition L.

Figure 7X:
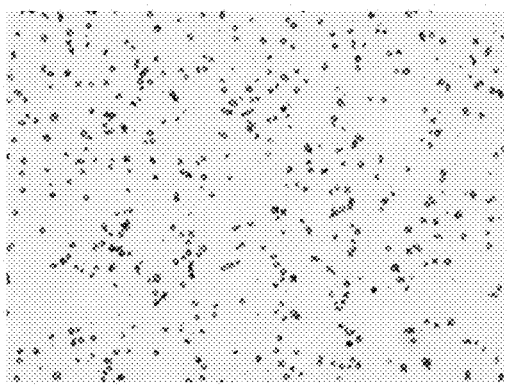

FIG. 7X depicts a tissue sample treated with Composition L.

Figure 7Y:
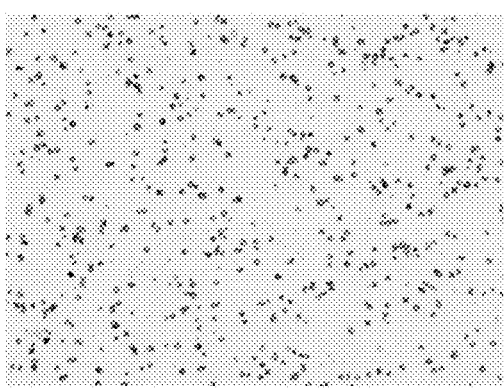

FIG. 7Y depicts a tissue sample treated with Composition M.

Figure 7Z:
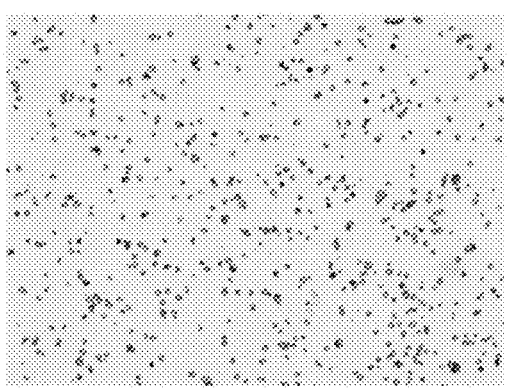
Figure 7A:
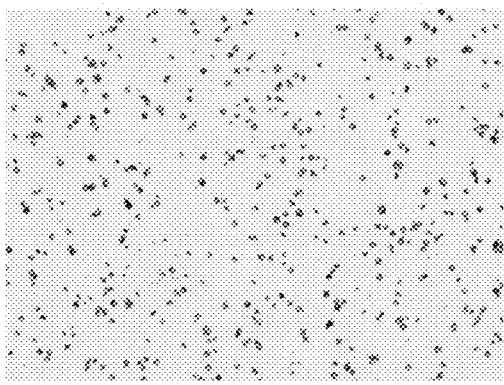
Figure 7B:
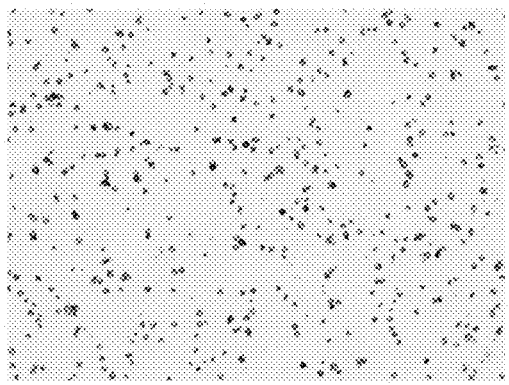
Figure 7C:
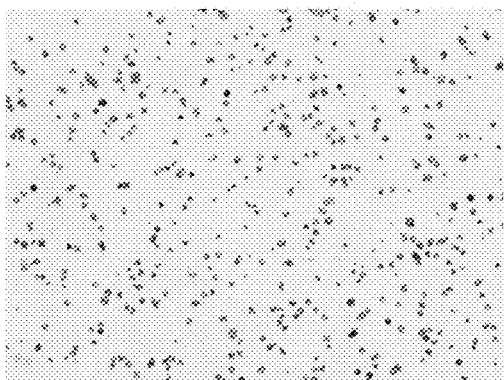
Figure 7D:
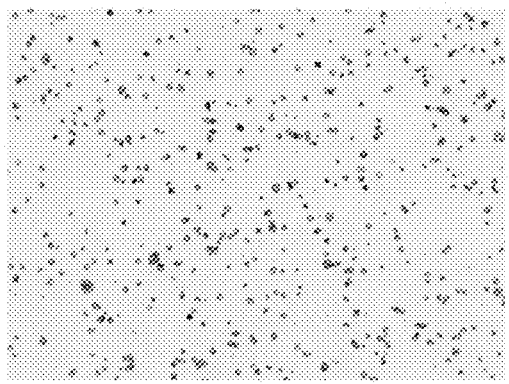
Figure 7E:
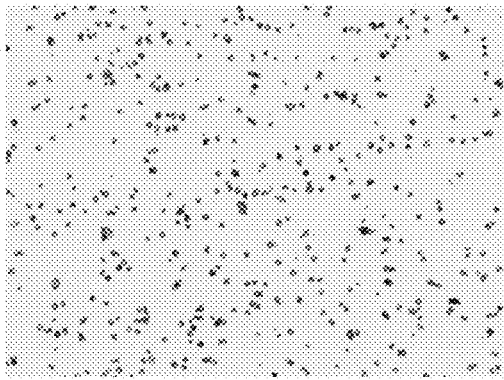
Figure 7F:
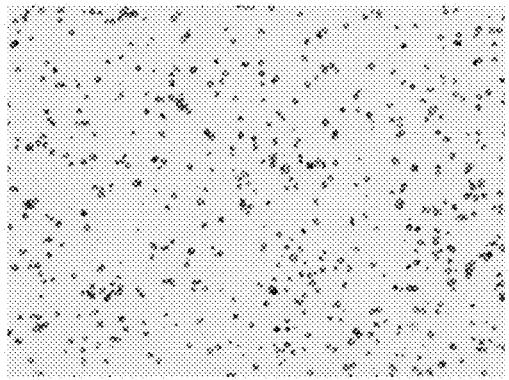

FIG. 7Z depicts a tissue sample treated with Composition M.

FIG. 7AA depicts a tissue sample treated with Composition N.

FIG. 7BB depicts a tissue sample treated with Composition N.

FIG. 7CC depicts a tissue sample treated with Composition O.

FIG. 7DD depicts a tissue sample treated with Composition O.

FIG. 7EE depicts a tissue sample treated with Composition P.

FIG. 7FF depicts a tissue sample treated with Composition P.

FIG. 7GG depicts a tissue sample treated with Composition Q.

FIG. 7HH depicts a tissue sample treated with Composition Q.

DETAILED DESCRIPTION

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

"Antibody," occasionally abbreviated "Ab," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

"Antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

A "biological sample" can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In certain examples, a sample is a quality control sample, such as one of the disclosed cell pellet section samples. In other examples, a sample is a test sample. For example, a test sample is a cell, a tissue or cell pellet section prepared from a biological sample obtained from a subject. In an example, the subject is one that is at risk or has acquired. Samples can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Samples can include multiple targets that can be specifically bound by one or more detection probes.

Calf intestine alkaline phosphatase (AP) is an enzyme that removes (by hydrolysis) and transfers phosphate group organic esters by breaking the phosphate-oxygen bond, and temporarily forming an intermediate enzyme-substrate bond. For example, AP hydrolyzes naphthol phosphate esters (a substrate) to phenolic compounds and phosphates. The phenols couple to colorless diazonium salts (chromogen) to produce insoluble, colored azo dyes.

"Chromophore" refers to a molecule or a part of a molecule responsible for its color. Color arises when a molecule absorbs certain wavelengths of visible light and transmits or reflects others. A molecule having an energy difference between two different molecular orbitals falling within the range of the visible spectrum may absorb visible light and thus be aptly characterized as a chromophore. Visible light incident on a chromophore may be absorbed thus exciting an electron from a ground state molecular orbital into an excited state molecular orbital.

Horseradish peroxidase (HRP) is an enzyme that can be conjugated to a labeled molecule. It produces a colored, fluorimetric, or luminescent derivative of the labeled molecule when incubated with a proper substrate, allowing it to be detected and quantified. HRP acts in the presence of an electron donor to first form an enzyme substrate complex and then subsequently acts to oxidize an electronic donor. For example, HRP may act on 3,3'-diaminobenzidinetrahydrochloride (DAB) to produce a detectable color. HRP may also act upon a labeled tyramide conjugate, or tyramide like reactive conjugates (i.e. ferulate, coumaric, caffeic, cinnamate, dopamine, etc.), to deposit a colored or fluorescent or colorless detectable moiety for tyramide signal amplification (TSA).

"Multiplex," "multiplexed," or "multiplexing" refers to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

Disclosed herein are enzyme inactivation compositions and methods for inactivating at least one enzyme in a biological sample prior to downstream processing. In the context of a multiplex assay where multiple chromogenic reagents are detected sequentially, it is desirable to inactivate any reagent or endogenous enzymes between successive chromogenic detection steps. As a result, it is believed that enzymes present in any one chromogenic detection step will not interfere with those in a later chromogenic detections step. This in turn is believed to improve upon the visualization and detection of the different chromogens used in the multiplex assay.

By way of example, a multiplex assay may comprise a series of chromogenic reagent detections steps. Each chromogenic reagent detection step involves supplying a chromogenic detection reagent, which comprises, for example, an enzyme and a chromogenic substrate for the enzyme. Without wishing to be bound by any particular theory, it is believed that the enzyme acts on the chromogenic substrate to produce a colored, detectable signal (i.e. enzyme substrate reactions convert colorless chromogens or chromogenic substrates into colored end products suitable for detection). In some embodiments, the chromogenic detection reagents are part of a detection kit, which could include, for example, one or more of a detection probe (e.g. an antibody), a labeling conjugate (where the labeling conjugate comprises an enzyme), a latent reactive moiety, and/or a chromogenic moiety.

Again, as an example, a multiplex assay may require a detection of a first chromogenic detection reagent (e.g. diaminobenzidine) followed by inactivation of a first enzyme present (e.g. HRP) in the first chromogenic detection reagent. The first chromogenic detection reagent is first applied to the sample and allowed time to react prior to detection of the first chromogenic substrate contained therein. A first enzyme inactivation composition may then be applied to act upon and inactivate the first enzyme in the first chromogenic detection kit, after detection of the chromogen. Subsequently, a second chromogenic detection reagent may be supplied to the sample (e.g. 4-Chloro-2-methylbenzenediazonium salt), followed by detection of a second chromogenic substrate in the second chromogenic detection reagent. A second enzyme (e.g. AP) in the second chromogenic detection reagent may then be inactivated by application of a second enzyme inactivation composition, which may be the same or different as the first enzyme inactivation composition. The steps of application of chromogenic detection regents, detection of chromogenic substrate signals, and enzyme inactivation may be repeated as needed depending on the assay involved and the targets being detected.

In some embodiments, the enzyme inactivation compositions of the present invention are applied to a biological sample comprising one or more reagent or endogenous enzymes. Examples of enzymes include, but are not limited to, horseradish peroxidase, alkaline phosphatase, acid phosphatase, glucose oxidase, β-galactosidase, β-glucuronidase or β-lactamase.

Particular examples of enzyme substrates and enzyme substrate systems useful in chromogenic detection assays include, but are not limited to, diaminobenzidine (DAB), 4-nitrophenylphospate (pNPP), naphthol phosphate, naphthol phosphate/Fast Red (e.g., 4-Chloro-2-methylbenzenediazonium salt and variations thereof such as Fast Red KL/Naphthol AS-TR, naphthol phosphate/fuschin, Fast Blue BB (4-(benzoylamino)-2,5-diethoxybenzenediazotetrachlorozincate)/naphthol phosphate (e.g. naphthol AS-TR phosphate (N-4-Chloro-2-methylphenyl)-3-(phosphonooxy) naphthalene-2-carboxamide), bromochloroindolyl phosphate (BCIP), BCIP/NBT (nitroblue tetrazolium), BCIP/INT (p-Iodonitrotetrazolium), tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), and 3-amino-9-ethyl carbazol (AEC). In some preferred embodiments where the enzyme is alkaline phosphatase, the chromogenic substrate system is selected from the group consisting of naphthol phosphate/Fast Red (and variations thereof such as Fast Red KL/Naphthol AS-TR), naphthol phosphate/fuschin, naphthol phosphate/Fast Blue BB (4-(benzoylamino)-2,5-diethoxybenzenediazotetrachlorozincate), 5-bromo,4-chloro,3-indolyl phosphate (BCIP)/naphthol phosphate, BCIP/nitroblue tetrazolium (NBT), and BCIP/p-Iodonitrotetrazolium (INT); quinone methides and their intermediates; HRP may act on 3,3'-diaminobenzidinetrahydrochloride (DAB) to produce a detectable color; HRP may also act upon a labeled tyramide conjugate, or tyramide like reactive conjugates (i.e. ferulate, coumaric, caffeic, cinnamate, dopamine, etc.), to deposit a colored or fluorescent or colorless detectable moiety for tyramide signal amplification (TSA).

In some embodiments, the enzyme inactivation composition is applied to a biological sample having at least one of a reagent peroxidase, one or more endogenous peroxidases, or an alkaline phosphatase. In other embodiments, the enzyme inactivation composition is applied to a biological sample having at least one of horseradish peroxidase (HRP), alkaline phosphatase (AP), or one or more endogenous peroxidases. In some embodiments, the sample comprises both HRP and AP.

In general, the enzyme inactivation compositions are placed in contact with the biological sample for a period of time and at a temperature sufficient to either substantially inactivate or completely inactivate (collected referred to as "inactivate" or "inactivated") the reagent or endogenous enzymes contained therein. By "substantially inactivate" or "substantially inactivated," it is meant that the activity of the one or more reagent or endogenous enzymes is reduced to about less than about 90% of its normal activity. In other embodiments, the activity of the one or more reagent or endogenous enzymes is substantially inactivated to about less than 95% of its normal activity. As used herein, the terms "completely inactivate" or "completely inactivated" mean that the activity of the one or more reagent or endogenous enzymes is less than 1% of its normal activity or reduced to levels that are not detectable by instrumentation. In some embodiments, at least one of a peroxidase (HRP or the one or more endogenous peroxidases) or an alkaline phosphatase is substantially inactivated. In other embodiments, at least one of a peroxidase (HRP or the one or more endogenous peroxidases) or an alkaline phosphatase is rendered completely inactive.

The skilled artisan will appreciate that several variables may be taken into consideration when designing an appropriate enzyme inactivation composition and/or method for applying the composition to the biological sample to render the reagent or endogenous enzymes therein inactivated. These variables include, for example, (i) the amount of time a composition is in contact with a biological sample (e.g. between about 4 minutes to about 8 minutes); (ii) the temperature at which the composition or the biological sample is held while it is in contact with the biological sample (e.g. between about 37° C. to about 50° C.); (iii) the pH of the composition (e.g. between about 1.5 and about 2.5); (iv) the amounts and/or concentrations of the individual components within the composition; and (v) the need for additional components (e.g. an elution mitigation agent or chelation agent). Of course, these variables may depend on the enzyme(s) being inactivated and/or other detection kit components.

For example, as the skilled artisan will appreciate, increasing the temperature of the enzyme inactivation composition or biological sample containing the enzyme inactivation composition may shorten the time needed for enzyme inactivation (e.g. from about 8 minutes to about 4 minutes). Conversely, increasing the time for inactivation may lessen the need for the use of higher temperatures (e.g. from about 37° C. to about 41° C.). Likewise, the skilled artisan will appreciate that the amounts of any of the components of the enzyme inactivation composition may influence the time and/or temperature variables, as well as the need for ancillary components (e.g. elution mitigation agents, chelation agents, etc.). By way of example, decreasing the pH (e.g. from about 2.0 to about 1.5) of the enzyme inactivation composition in contact with the biological sample may reduce at least one of the time or temperature variables (e.g. from about 8 minutes to about 4 minutes) needed to inactivate one or more of the enzymes.

Any enzyme inactivation composition may be applied to the biological sample provided that the composition, or the amount of time and/or temperature that the composition remains in contact with the biological sample, does not detrimentally affect tissue antigen detection signal intensity or tissue morphology and/or impact the intensity and/or hue of the chromogen and/or counterstain. For example, while a visually detectable DAB intensity or hue shift may occur after application of the enzyme inactivation composition, the enclosed compositions and methods should be selected to mitigate any intensity or hue changes such that a detectable intensity or hue of the chromogenic substrate may be determined to not be substantially reduced following application of an enzyme inactivation composition by pathological or qualified reader review.

In general, the present invention provides an enzyme inactivation composition comprising an acid having a pH between about 1 and about 3, a preservative, and a peroxide. In some embodiments, the enzyme inactivation composition further comprises at least one of a chelation agent, a buffer, and/or an elution mitigation agent.

In some embodiments, the pH of the composition ranges from about 0.5 to about 3.5. In other embodiments, the pH of the composition ranges from about 1 to about 3. In yet other embodiments, the pH of the composition is about 1.5. In yet further embodiments, the pH of the composition is about 2.0. In yet additional embodiments, the pH of the composition is about 2.5. Without wishing to be bound by any particular theory, it is believed that lower pHs may help to improve enzyme inactivation, i.e. there is a directly correlation between composition pH and enzyme activity.

Turning to the components of the composition, any acid may be used in conjunction with the present invention provided that the pH meets the pH criteria established herein. The acid may be an inorganic acid or an organic acid and may be selected from monoprotic acids or polyprotic acids. In some embodiments, the acid is selected from acetic acid, benzoic acid, citric acid, hydrochloric acid, lactic acid, nitric acid, succinic acid, sulfuric acid, sulfurous acid, tartaric acid, trichloroacic acid, low pH amino acids, e.g. alanine, or the salts therefore.

In some embodiments, the acid is a polycarboxylic acid or a salt thereof. In other embodiments, the polycarboxylic acid has a molecular weight of less than about 500 g/mol. Suitable polycarboxylic acids may have the formula $CO(OH)—R_1—R_2(C(O)(OH)—R_3—C(O)OH$, where $R_1$, $R_2$, and $R_3$ may be the same or different and may be with a substituted or unsubstituted aliphatic or aromatic group, and wherein any of $R_1$, $R_2$, or $R_3$ may contain any number of additional carboxylic acid groups. In some embodiments, the polycarboxylic acid is a citrate or isocitrate or a salt thereof. In other embodiments, the polycarboxylic is a sodium citrate, e.g. 1M citrate.

In some embodiments, the acid is capable of chelating metal ions, including calcium, iron, magnesium and zinc ions. For example, it is believed that citrate is able to sequester $Ca^{2+}$ co-factors. In other embodiments, a chelation agent is added to the composition when chelating polycarboxylic acids are absent. In some embodiments, the optional chelating agent is present in an amount of between about 0.05% to about 2.5% by total weight of the composition. In some embodiments where the acid cannot chelate the enzyme co-factor directly, a chelation agent is added to sequester the requisite enzyme cofactors. These chelators may include, but not be limited to, ethylenediaminetetraacetic acid (EDTA), ethylene glycol tetraacetic acid (EGTA), ethylenediaminedisuccinic acid (EDDS), methylglycinediacetic acid (MGDA), diethylene triamine pentaacetic acid (DTPA) or other chelation agents suitable for sequestering requisite enzyme cofactors. Without wishing to be bound by any particular theory, it is believed that the chelation of the metal ions traditionally found within a cell or in conjunction with an enzyme may assist in irreversibly inactivating or denaturing the enzyme, thus contributing to the inactivation of the enzyme.

Any peroxide may be used in the enzyme inactivation composition of the present invention, including inorganic peroxides and organic peroxides. In some embodiments, the peroxides have the formula $R_a—O—O—R_b$, where $R_a$ and $R_b$ may be the same or different and may independently be selected from hydrogen, an alkyl group, an aryl group, an acid group (R(C(O)), where R can be the same as $R_a$ or $R_b$, or an acyl group. In some embodiments, the peroxide is hydrogen peroxide ($H_2O_2$). In general, the peroxide is present in an amount ranging from between about 0.025% to about 5% by total weight of the enzyme inactivation composition.

The preservative may be selected from any preservative typically used in conjunction with biological samples. In some embodiments, the preservative is sodium azide ($NaN_3$). In general, the preservative is present in an amount ranging from between about 0.025% to about 1.5% by total weight of the enzyme inactivation composition. In some embodiments, $NaN_3$ is used as a preservative as it is believed that $NaN_3$ is also a reversible inhibitor of peroxidase, and may further contribute to enzyme inactivation (see Examples 3, 6, 7, and 8 herein).

In some embodiments, an elution mitigation agent is included within the enzyme inactivation composition. In some embodiments, the elution mitigation agent is an alkaline chloride salt. The elution mitigation agent may be selected from the group consisting of sodium chloride and potassium chloride. In some embodiments, the elution mitigation agent is a salt. In general, the elution mitigation agent is present in an amount ranging from between about 1% to about 5% by total weight of the enzyme inactivation composition. In some embodiments, 0.5M NaCl is used as an elution mitigation agent. In other embodiments, 0.75M NaCl is used as an elution mitigation agent. In yet other embodiments, 1M NaCl is used as an elution mitigation agent.

The compositions of the present invention may also comprise other components such as buffers, reversible enzyme inhibitors, irreversible enzyme inhibitors, etc.

In one embodiment of the present invention is an enzyme inactivation composition comprising a polycarboxylic acid having a pH ranging from between about 1 to about 3.0; and at least one of a peroxide and a preservative. In another embodiment of the present invention is an enzyme inactivation composition comprising a citrate having a pH ranging from between about 1 to about 3.0, hydrogen peroxide, and sodium azide. In some embodiments, the peroxide is present in an amount ranging from between about 0.25% to about 1.5% by total weight of the composition, and the preservative is present in an amount ranging from between about 0.05% to about 1.0% by total weight of the composition.

In yet another embodiment of the present invention is an enzyme inactivation composition comprising a citrate having a pH ranging from between about 1 to about 3.0; hydrogen peroxide, and sodium azide and sodium chloride. In some embodiments, the molarity of sodium chloride used ranges from about 0.25M to about 1M.

In one embodiment, the enzyme inactivation composition comprises citrate having a pH of about 1.5, $H_2O_2$ (about 1% by total weight of the composition), and $NaN_3$ (about 0.08% by total weight of the composition). In another embodiment, the enzyme inactivation composition comprises citrate having a pH of about 1.5, $H_2O_2$ (about 0.5% by total weight of the composition), and $NaN_3$ (about 0.08% by total weight of the composition). In another embodiment, the enzyme inactivation composition comprises citrate having a pH of about 2.0, $H_2O_2$ (about 1% by total weight of the composition), and $NaN_3$ (about 0.08% by total weight of the composition). In another embodiment, the enzyme inactivation composition comprises citrate having a pH of about 1.5, $H_2O_2$ (about 1% by total weight of the composition), $NaN_3$ (about 0.08% by total weight of the composition), and sodium chloride (about 0.5M). In another embodiment, the enzyme inactivation composition comprises citrate having a pH of about 1.5, $H_2O_2$ (about 1% by total weight of the composition), $NaN_3$ (about 0.08% by total weight of the composition), and sodium chloride (about 0.75M). In another embodiment, the enzyme inactivation composition comprises citrate having a pH of about 1.5, $H_2O_2$ (about 1% by total weight of the composition), $NaN_3$ (about 0.08% by total weight of the composition), and sodium chloride (about 1M).

The enzyme inactivation compositions, and likewise the detection kits and chromogenic detection reagents, may be applied to the biological sample using any means known in the art. For example, the detection kits and enzyme inactivation compositions may be applied to the biological sample with a specimen processing apparatus, including an automated specimen processing apparatus. In general, a specimen processing apparatus is configured to apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or nonaqueous-based antigen retrieval solutions, antigen recovering buffers, etc.), or the like. In some embodiments, detection kits and enzyme inactivation compositions are each applied sequentially by the specimen processing apparatus.

The specimen processing apparatus can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

Any amount of the enzyme inactivation compositions may be applied to the biological sample to properly inactivate the enzyme contained herein. In some embodiments, between about 0.25 drops and about 2 drops of the enzyme inactivation composition is added to a biological sample to effectuate enzyme inactivation. In other embodiments, about 1 drop (between about 50 µL to about 150 µL) of the composition of the present invention is added to a "puddle" in contact with the biological sample, where the puddle contains the chromogenic detection reagents or kit components (e.g. a preexisting volume of fluid on contact with the sample). In some embodiments, about 100 µL of an enzyme inactivation reagent as described herein is added to a puddle having a volume of about 300 µL to afford a puddle having a pH of about 2.5. In some embodiments, about 100 µL of an enzyme inactivation reagent as described herein is added to a puddle having a volume of about 300 µL to afford a puddle having a pH of about 2 to about 3. Of course, any amount needed to render the enzymes in a biological sample inactivated may be used as needed. The composition may also be applied as a thin film on the surface of the biological sample. The thin film solution may then be adapted at one-quarter buffer concentrations at a pH of about 2.5 to use neat on the tissue without modification. All reagent conditions effectively provided AP and HRP enzyme inactivation.

As will be appreciated by the skilled artisan, although the composition may have a certain pH, when the composition is added to the biological sample, the resulting "puddle" or thin film in contact with the biological sample may have about the same or a different pH than the pH of the composition. For example, if a drop of the disclosed composition is added to an existing "puddle" in contact with the biological sample, where the existing puddle has a pH higher (e.g. a pH of 2.5) than the composition being added (e.g. a pH of 1.5), the resulting new "puddle" may have a pH of 2.0. Thus, in some embodiments, if a certain pH of the cumulative puddle in contact with the biological sample is desired, the skilled artisan may add a composition for inactivation that has a pH lower than the existing puddle.

The enzyme inactivation composition is applied to the biological at a temperature and for a time such that any reagent or endogenous enzyme contained therein is either substantially or completely inactivated. In some embodiments, the enzyme inactivation composition is maintained in communication with the biological sample for at least about 3 minutes. In other embodiments, the composition is maintained in communication with the biological sample for at least about 4 minutes. In other embodiments, the composition is maintained in communication with the biological sample for at least about 8 minutes. In yet other embodiments, the composition is maintained in communication with the biological sample for a period of time ranging from between about 3 minutes to about 16 minutes. In yet further embodiments, the composition is maintained in communication with the biological sample for a period of time ranging from between about 4 minutes to about 12 minutes. In yet additional embodiments, the composition is maintained in communication with the biological sample for a period of time ranging from between about 4 minutes to about 8 minutes. In yet additional embodiments, the composition is maintained in communication with the biological sample for about 4 minutes.

In some embodiments, the enzyme inactivation composition, the biological sample, and/or the instrument for applying the composition to the biological sample (referred to collection as "the temperature of the composition") are maintained at a specific temperature to effectuate enzyme inactivation. In some embodiments, the temperature of the composition is a temperature above 30° C. In other embodiments, the temperature of the composition ranges from between about 30° C. to about 90° C. In yet other embodiments, the temperature of the composition ranges from between about 35° C. to about 50° C. In yet other embodiments, the temperature of the composition ranges from between about 35° C. to about 41° C. In yet further embodiments, the temperature of the composition ranges is about 37° C. In yet additional embodiments, the temperature of the composition ranges is about 41° C. In yet additional embodiments, the temperature of the composition ranges is about 50° C.

In some embodiments, the composition of the present is added to a biological sample comprising first chromogenic detection reagents or a first detection kit, where the biological sample and/or the detection reagents/kit comprise at least one enzyme, such as one or more peroxidases or phosphatases. In some embodiments, the composition is allowed to remain in contact with the biological sample, containing the detection reagents/kit, for a pre-determined amount of time and at a pre-determined temperature such that the one or more enzymes are substantially inactivated or completely inactivated.

Following enzyme inactivation, a second chromogenic detection reagent or a second detection kit is added to the sample, where the second chromogenic detection reagent or second detection kit comprises a second enzyme. Following addition of the second reagent/kit, a second enzyme inactivation composition is added to the sample to substantially or completely inactivate the second enzyme. The skilled artisan will appreciate that the above sequence of the addition of a detection reagent/kit followed by enzyme inactivation may be repeated any number of times for multiplexed assays. Depending on the level of multiplexing, the methods may be repeated one, two, three, four, five, six, seven, eight, or more times depending on the number of targets that are to be detected in the sample.

In another aspect of the present invention is a method of detecting multiple targets in a biological sample, comprising: (a) contacting the biological sample with a first chromogenic detection reagent having a first enzyme; (b) detecting a first signal from the first chromogenic detection reagent; and (c) inactivating the first enzyme by applying a first enzyme inactivation composition as disclosed herein, wherein at least one of the first enzyme inactivation composition or the biological sample are maintained at a temperature ranging from between about 37° C. to about 50° C. for a time period ranging from between about 4 minutes to about 16 minutes. In some embodiments, the method further comprises the steps of (d) contacting the biological sample with a second chromogenic detection reagent having a second enzyme; (e) detecting a second signal from the second chromogenic detection reagent; and (f) inactivating the second enzyme by applying a second enzyme inactivation composition as disclosed herein, wherein at least one of the second enzyme inactivation composition or the biological sample are maintained at a temperature ranging from between about 37° C. to about 50° C. for a time period ranging from between about 4 minutes to about 16 minutes. In some embodiments, the steps are repeated for detecting additional chromogenic detection regents, such as third, fourth, and fifth chromogenic detection reagents.

In some embodiments, the method comprises the steps of (i) contacting a biological sample with a first detection probe (e.g. an antibody); (ii) contacting the biological sample with a first labeling conjugate wherein the first labeling conjugate comprises a first enzyme (where the labeling conjugate specifically binds to the detection probe and is configured to label the target with an enzyme); (iii) contacting the biological sample with a first signaling conjugate comprising a first latent reactive moiety and a first chromogenic moiety; (iv) detecting the first target through absorbance of the light by the first chromogenic moiety of the first signaling conjugate; and (v) contacting the biological sample with a first enzyme inactivation composition disclosed herein to substantially inactivate or complete inactivate the first enzyme contained in the biological sample. The signaling conjugate provides the detectable signal that is used to detect the target. A chromophore moiety is generally described as the part of a molecule responsible for its color. The latent reactive moiety is configured to undergo catalytic activation to form a reactive species that can covalently bond with the sample or to other detection components. The catalytic activation is driven by one or more enzymes (e.g., horseradish peroxidase). These types of specific detection kits and their application to the biological sample is further described in US Patent Publication No. 2013/0260379, the disclosure of which is incorporated by reference in its entirety.

In some embodiments, after the first enzyme is inactivated, the method further comprises the steps of (vi) contacting a biological sample with a second detection probe; (vii) contacting the biological sample with a second labeling conjugate wherein the second labeling conjugate comprises a second enzyme; (viii) contacting the biological sample with a second signaling conjugate comprising a second latent reactive moiety and a second chromogenic moiety; (ix) detecting the second target through absorbance of the light by the second chromogenic moiety of the second signaling conjugate; and (x) contacting the biological sample with a second enzyme inactivation composition disclosed herein to substantially inactivate or complete inactivate the second reagent enzyme contained in the biological sample. In some embodiments, the first and second enzyme inactivation compositions are the same and where the first and second enzymes are the same or different.

The disclosed method steps (i) through (x) may be carried out in any suitable order, and are not limited to those described herein. In some embodiments, the method may comprise steps wherein the labeling conjugates are added to the biological sample, followed by the signaling conjugate. In other disclosed embodiments, the method may comprise steps wherein the labeling conjugates are added to the biological sample, followed by an amplifying conjugate, an additional enzyme conjugate, and the signaling conjugate. The conjugates disclosed herein may be added simultaneously, or sequentially. The conjugates may be added in separate solutions or as compositions comprising two or more conjugates. Also, each class of conjugates used in the disclosed method may comprise the same or different conjugate components. For example, when multiple signaling conjugates are added to the sample, the conjugates may comprise the same or different chromogenic moieties and/or latent reactive moieties. Solely by way of example, one signaling conjugate may comprise a coumarin chromophore coupled to a tyramine moiety and another signaling conjugate may comprise a rhodamine chromophore coupled to a tyramine derivative moiety. The number of signaling conjugates suitable for use in the disclosed multiplexing assay may range from one to at least six, or more typically from two to five. In some embodiments, the method is used to detect from three to five different targets using from three to five different signaling conjugates. Multiple targets may be detected in a single assay using the method disclosed herein. In another embodiment, any one or more of the steps disclosed herein for the method are performed by an automated slide staining instrument.

The methods of inactivating the enzymes of the present invention may also be combined with additional steps, such as steps designed to elute components of the detection kits and/or wash or purify the biological sample.

In some embodiments, the biological samples are pre-treated with an enzyme inactivation composition to substantially or completely inactivate endogenous peroxidase activity. For example, some cells or tissues contain endogenous peroxidase. Using an HRP conjugated antibody may result in high, non-specific background staining. This non-specific background can be reduced by pre-treatment of the sample with an enzyme inactivation composition as disclosed herein. In some embodiments, the samples are pre-treated with hydrogen peroxide only (about 1% to about 3% by weight of an appropriate pre-treatment solution) to reduce endogenous peroxidase activity. Once the endogenous peroxidase activity has been reduced or inactivated, detection kits may be added, followed by inactivation of the enzymes present in the detection kits, as provided above. The disclosed enzyme inactivation composition and methods can also be used as a method to inactivate endogenous enzyme peroxidase activity.

In some embodiments if the specimen is a sample embedded in paraffin, the sample can be deparaffinized using appropriate deparaffinizing fluid(s). After a waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

After the specimens are processed, a user can transport specimen-bearing slides to an imaging apparatus for analysis or other downstream processing. For example, the imaging apparatus may be a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/

002772 and U.S. Patent Application Publication No. 2014/0178169 are incorporated by reference in their entities. In other embodiments, the imaging apparatus includes a digital camera coupled to a microscope.

In another aspect of the present invention is a kit comprising a first component comprising a polycarboxylic acid having a pH ranging from about 1 to about 3; and at least one of a peroxide or a preservative, wherein the peroxide is present in an amount ranging from between about 0.25% to about 1.5% by total weight of the composition, and wherein the preservative is present in an amount ranging from between about 0.05% to about 1.0% by total weight of the composition; and a second component comprising an elution mitigation agent. In some embodiments, the elution mitigation agent is a salt. In other embodiments, the second component is selected from the group consisting of a buffer, a chelation agent or mixtures thereof. In some embodiments, the first and second components are provided with a third component which may include chromogenic detection reagent components or components of a detection kit.

EXAMPLES

General Immunohistochemistry (IHC) Protocol(s)

All IHC staining experiments were carried out on a VENTANA BenchMark® XT automated tissue staining platform using reagents from Ventana Medical Systems, Inc. (Tucson, AZ, USA; "Ventana") unless otherwise specified. Horseradish Peroxidase IHC detections were performed using Ventana ultraView Universal DAB Detection Kit (VMSI, #760-500) or Ventana OptiView DAB IHC Detection Kit (VMSI, #760-700). Alkaline Phosphatase IHC detections were performed using Ventana ultraView Universal Alkaline Phosphatase Red Detection Kit (VMSI, #760-501). AffiniPure rabbit anti-horseradish peroxidase was purchased from Jackson ImmunoResearch (#323-005-021).

General ultraView Universal DAB IHC Detection Method

The following common steps were performed: (1) deparaffinization with EZ Prep detergent solution (Ventana Medical Systems, Inc. (VMSI), #950-101) (75° C.; 20 min); (2) washing with Reaction Buffer (VMSI, #950-300); (3) antigen retrieval in Cell Conditioning 1 (VMSI #950-124) (95° C.; time dependent on antigen of interest); (4) washing (same as step 2); (5) endogenous peroxidase was inactivated using ultraVIEW Universal DAB Inhibitor (VMSI, #253-4291) (37° C.; 4 min); (6) washing (same as step 2); (7) primary antibody (Ab) incubation (37° C.; time dependent on primary antibody ranging from 8-32 minutes); (8) washing (same as step 2); (9) primary antibody detection with ultraVIEW Universal HRP Multimer (VMSI, #253-4290) (37° C.; 8 min); (10) washing (same as step 2); (11) visualized via a brown precipitate produced by HRP upon the addition of ultraVIEW Universal hydrogen peroxide (VMSI, 253-4293) and ultraVIEW Universal DAB (VMSI, 253-4292) (37° C.; 8 min); (12) washing (same as step 2); and (13) The DAB was toned by the addition of ultraVIEW Universal copper (VMSI, 253-4294) (37° C.; 4 min). In some cases, the stained tissue sections were counterstained with modified Mayer's hematoxylin (VMSI Hematoxylin II, 790-2280) (37° C.; 4 min) and then incubated with Bluing Reagent (VMSI, 790-2037) (37° C.; 4 min). The slides were then rinsed with a detergent water mixture, dehydrated through a graded ethanol series, cleared with xylene, and manually cover-slipped. The slides were viewed by brightfield microscopy.

General OptiView DAB IHC Detection Method

The following common steps were performed: (1) deparaffinization with EZ Prep detergent solution (Ventana Medical Systems, Inc. (VMSI), #950-101) (75° C.; 20 min); (2) washing with Reaction Buffer (VMSI, #950-300); (3) antigen retrieval in Cell Conditioning 1 (VMSI #950-124) (95° C.; time dependent on antigen of interest); (4) washing (same as step 2); (5) endogenous peroxidase was inactivated using OptiVIEW Peroxidase Inhibitor (VMSI, #253-4578) (37° C.; 4 min); (6) washing (same as step 2); (7) primary antibody (Ab) incubation (37° C.; time dependent on primary antibody ranging from 8-32 minutes); (8) washing (same as step 2); (9) primary antibody detection with OptiVIEW HQ Universal Linker (VMSI, #253-4580) (37° C.; 8 min); (8) washing (same as step 2); (9) linker detection with OptiVIEW HRP Multimer (VMSI, #253-4581) (37° C.; 8 min); (10) washing (same as step 2); (11) visualized via a brown precipitate produced by HRP upon the addition of OptiVIEW $H_2O_2$ (VMSI, 253-4583) and OptiVIEW DAB (VMSI, 253-4582) (37° C.; 8 min); (12) washing (same as step 2); and (13) The DAB was toned by the addition of OptiVIEW Copper (VMSI, 253-4584) (37° C.; 4 min). In some cases, the stained tissue sections were counterstained with modified Mayer's hematoxylin (VMSI Hematoxylin II, 790-2280) (37° C.; 4 min) and then incubated with Bluing Reagent (VMSI, 790-2037) (37° C.; 4 min). The slides were then rinsed with a detergent water mixture, dehydrated through a graded ethanol series, cleared with xylene, and manually cover-slipped. The slides were viewed by brightfield microscopy.

General ultraView Universal Alkaline Phosphatase Red IHC Detection Method

The following common steps were performed: (1) deparaffinization with EZ Prep detergent solution (Ventana Medical Systems, Inc. (VMSI), #950-101) (75° C.; 20 min); (2) washing with Reaction Buffer (VMSI, #950-300); (3) antigen retrieval in Cell Conditioning 1 (VMSI #950-124) (95° C.; time dependent on antigen of interest); (4) washing (same as step 2); (5) primary antibody (Ab) incubation (37° C.; time dependent on primary antibody ranging from 8-32 minutes); (6) washing (same as step 2); (7) primary antibody detection with ultraView Universal Alkaline Phosphatase Multimer (VMSI, #253-4327) (37° C.; 8 min); (8) washing (same as step 2); (9) visualized via a red precipitate produced by AP upon the addition of ultraView Universal Alkaline Phosphatase Red Enhancer (VMSI, 253-4326) (37° C.; 4 min); (10) ultraView Universal Alkaline Phosphatase Red A (VMSI, 253-4329) and ultraView Universal Alkaline Phosphatase Red Naphthol (VMSI, 253-4328) (37° C.; 8 min); (11) ultraView Universal Alkaline Phosphatase Red B (VMSI, 253-4330) (37° C.; 8 min); and (12) washing (same as step 2). In some cases, the stained tissue sections were counterstained with modified Mayer's hematoxylin (VMSI Hematoxylin II, 790-2280) (37° C.; 4 min) and then incubated with Bluing Reagent (VMSI, 790-2037) (37° C.; 4 min). The slides were then rinsed with a detergent water mixture, dried in an oven at 60° C. for 30 to 60 minutes, and manually cover-slipped. The slides were viewed by brightfield microscopy.

General Horseradish Peroxidase and Alkaline Phosphatase Enzyme Inactivation Method HRP and AP enzyme inactivation using the disclosed composition was examined at various steps during an IHC assay to examine the reagent composition and instrument method impact on various IHC detection steps: (1) antigen stability (enzyme inactivation step was placed after antigen retrieval and before antigen detection with primary antibody); (2) enzyme inactivation (enzyme inactivation step was placed after antibody detection with enzyme multimer and before chromogen detection); and (3) detection elution (enzyme inactivation step was placed after chromogen deposition and before counterstaining if counterstain was applied). The following common steps were performed on the VENTANA BenchMark® XT automated tissue staining platform: (1) washing with Reaction Buffer (VMSI, #950-300); (2) treatment with enzyme inactivation reagent at various temperatures (37 to 50° C.) and incubation times (4 to 20 minutes); and (3) washing (same as step 1). This three step process would be repeated as appropriate if multiple kill steps were performed in series.

Other enzyme inactivation/inhibition methods commonly utilized were examined to compare reagent performance in an automated setting. A similar general procedure to that above was performed with enzyme inactivation methods using Ventana PO Inhibitor (VMSI #253-4578) and Discovery Inhibitor (VMSI #760-4840). Methods which included multiple treatments were done with a single with Reaction Buffer (VMSI, #950-300) washing step between the treatments. Various Ventana instrument bulk reagents [Ventana Reaction Buffer (VMSI #950-300), Ventana Cell Conditioning 1 (CC1, VMSI #950-124); and Ventana Cell Conditioning 1 (CC1, VMSI #950-123)] have been used to inactivate detection systems using similar protocols at elevated temperatures. In certain protocols, a lower residual puddle volume was desired to allow an increased reagent concentration. A "jet-drain" procedure was on the VENTANA BenchMark® XT automated tissue staining platform prior to reagent addition which reduced the puddle volume to approximately 20 to 25% nominal Reaction Buffer (VMSI, #950-300).

AP and HRP model systems were used in the examples herein (OptiView DAB or ultraView AP Red Detection systems, CD20 on tonsil tissue, 8 min CC1, 16 min CD20).

In particular, peroxidase inactivation compositions/methods were investigated after HRP multimer incubation and prior to DAB detection (OptiView DAB Detection, CD20, tonsil tissue, 8 min CC1, 16 min CD20). OptiView DAB IHC Detection Kit (OptiView) is an indirect, biotin-free system for detecting mouse IgG, mouse IgM and rabbit primary antibodies. The kit is intended to identify targets by immunohistochemistry (IHC) in sections of formalin-fixed, paraffin-embedded and frozen tissue that are stained on the VENTANA automated slide stainers and visualized by light microscopy.

Likewise, calf intestine AP inactivation compositions/methods were investigated after AP multimer incubation and before AP Red detection (ultraView AP Red Detection, CD20, tonsil tissue, 8 min CC1, 16 min CD20). Ventana Medical Systems, Inc. (Ventana) ultraView Universal Alkaline Phosphatase Red Detection Kit is an indirect, biotin-free system for detecting mouse IgG, mouse IgM and rabbit primary antibodies. The kit is intended to identify targets by immunohistochemistry (IHC) in sections of formalin-fixed, paraffin-embedded and frozen tissue that are stained on the Ventana BenchMark Series instruments including Benchmark, Benchmark XT, and Benchmark ULTRA automated slide stainers.

In the figures referred to herein, in the context of DAB, decreasing amounts of visible DAB indicate increasing HRP enzyme inactivation. For example, where a sample shows only counterstain and no visible DAB signal, enzyme inactivation may be complete or close to complete. Likewise, in the context of Fast Red, decreasing amounts of visible Fast Red indicate increasing AP enzyme inactivation. For example, where a sample shows only counterstain and no visible Fast Red signal, enzyme inactivation may be complete or close to complete.

Example 1—Effect of Reagent pH on Peroxidase Inhibition/Inactivation

The Ventana ultraView Universal DAB IHC Detection kit was used during this study. The desired enzyme inactivation step was inserted into the general protocol described above after the ultraVIEW Universal HRP Multimer (VMSI, #253-4290) detection step and before ultraVIEW Universal DAB chromogen deposition. The enzyme inactivation step was performed at about 37° C. for about 16 minutes. Antigen retrieval was performed using Ventana CC1 for about 8 minutes. The Ventana Confirm MsAntiCD20 (Clone L26, VMSI #760-2531) primary antibody was used at about 37° C. for about 16 minutes. HRP inactivation/denaturation pH dependence was verified through treatments with 1M citrate buffer with pH=about 1.5 to about 3.0 at about 0.5 unit increments. An increase in reagent pH caused an increase in the puddle pH to which the tissue was exposed when about one drop of the composition was added to the Ventana Reaction Buffer puddle (Reagent pH/Approximate final puddle pH: about 1.5/about 2.0; about 2.0/about 2.5 to 2.75; about 2.5/about 3.0 to 3.25; about 3.0/about 3.5 to 4.0). The HRP enzyme inactivation efficiency decreased as the resulting puddle pH increased. Only 1M citrate base (pH=about 1.5) demonstrated full inactivation of HRP enzyme activity. The DAB IHC staining intensity and percent staining cells increased as the reagent pH was increased. Residual endogenous peroxidase was observed by DAB IHC detection following peroxidase inactivation treatment.

Example 2—Effect of Reagent Application Temperature on Peroxidase Inhibition/Inactivation The Ventana ultraView Universal DAB IHC Detection kit was used during this study. The desired enzyme inactivation step was inserted into the general protocol described above after the ultraVIEW Universal HRP Multimer (VMSI, #253-4290) detection step and before ultraVIEW Universal DAB chromogen deposition. The enzyme inactivation step was performed with variable temperatures and incubation times. Antigen retrieval was performed using Ventana CC1 for about 8 minutes. The Ventana Confirm MsAntiCD20 (Clone L26, VMSI #760-2531) primary antibody was used at about 37° C. for about 16 minutes. The composition's impact on tissue antigen detection signal intensity was believed to be affected by a combination reagent pH, application time and temperature. The 1M citrate base (pH=about 1.5) was investigated at elevated temperature to determine how temperature could help shorten enzyme inactivation. It was shown that the incubation time for 1M citrate base (pH=about 1.5) could be reduced from about 16 min at about 37° C. to about 8 min at about 41° C. or about 4 min at T≥about 45° C. with complete inhibition of HRP enzyme activity. It was believed that tissue areas with high necrosis had a higher multimer nonspecific binding, produce stronger DAB IHC staining and were more valuable sites to investigate enzyme inactivation. The DAB IHC staining intensity and percent staining cells were slightly more at about 41° C. and about 8 min than at about 37° C. and about 16 min when the enzyme inactivation reagent pH was increased. Residual endogenous peroxidase activity was observed by DAB IHC detection following all enzyme inactivation treatments at about 41° C. and about 8 min.

Example 3—Effect of Additional Additives on Peroxidase Enzyme Inactivation

A citrate based enzyme inactivation reagent required an antibacterial reagent to achieve targeted shelf life. The expected reagent pH=about 1.5 to about 2.0 was at or below the tolerant pH range for Proclin® reagents. It was believed that Proclin 950 had a pH tolerance range of pH=about 2 to about 12, and the other Proclin reagents pH had a tolerance of pH≥about 2.5. Sodium azide (about 0.08 wt %) was determined to be a viable bacteriostatic preservative option since it was believed that it not only acted as bacteriostatic oxidase inhibitor but could also reversibly inhibit peroxidases.

The Ventana ultraView Universal DAB IHC Detection kit was used during this study. The desired enzyme inactivation step was inserted into the general protocol described above after the ultraVIEW Universal HRP Multimer (VMSI, #253-4290) detection step and before ultraVIEW Universal DAB chromogen deposition. The enzyme inactivation step was performed at about 37° C. for about 4 minutes. Antigen retrieval was performed using Ventana CC1 for 8 minutes. The Ventana Confirm MsAntiCD20 (Clone L26, VMSI #760-2531) primary antibody was used at about 37° C. for about 16 minutes. A hydrogen peroxide titer (about 0.1, about 0.5 and about 1.0 wt %) was investigated in the 1M citrate base reagent (pH=about 1.5) to access the added endogenous and detection based peroxidases inhibition ability. Increased peroxidase inactivation efficiency was observed with the addition of about 0.5 or about 1.0 wt % hydrogen peroxide at about 37° C. in about 4 min. Hydrogen peroxide was believed to not be as effective at about 0.1 wt % where residual HRP activity was observed. Sodium azide addition (about 0.08 wt %) to the above citrate-hydrogen peroxide composition afforded similar results. Substantially no endogenous or detection kit peroxidase activity was observed with about 0.5 or about 1.0 wt % hydrogen peroxide. This reagent composition achieved enzyme inactivation/inhibition in about 4 min incubation in absence of additional heat on a VENTANA BenchMark® XT automated tissue staining platform (T=about 37° C.).

Sodium chloride was previously observed to minimize detection kit elution in previous studies and was expected to be required during enzyme inactivation to minimize detection kit. Sodium chloride was tittered into the base citrate reagent [about 1M citrate (pH=about 1.5)+about 1.0 wt % $H_2O_2$+about 0.08 wt % $NaN_3$] from about 0.25 M to about 4 M NaCl. Substantially no change was observed in peroxidase inactivation efficiency since it was believed that adding NaCl would make the reagent a stronger protein denaturing reagent. However, sodium chloride was believed to minimize OptiView detection kit elution.

The Ventana OptiView DAB IHC Detection kit (VMSI #760-700) was used during this study. The desired enzyme inactivation step was inserted into the general protocol described above after the OptiVIEW Universal HRP Multimer (VMSI, #253-4581) detection step. The enzyme inactivation step was performed at about 37° C. for about 4 minutes. The tissue was treated with RbAntiHRP detection (Jackson #323-005-021) (at about 37° C. for about 16 minutes), a washing step, UltraView Universal HRP multimer (at about 37° C. for about 8 minutes) (VMSI, #253-4290), and then OptiVIEW DAB chromogen detection. Antigen retrieval was performed using Ventana CC1 for about 64 minutes. The Ventana Confirm MsAntibcl2 (Clone 124, VMSI #790-4464) primary antibody was used at about 37° C. for about 16 minutes. RbAntiHRP detection on the bcl2 control standard without elution treatment amplified the DAB IHC detection with increased background. Enzyme inactivation with base citrate reagent caused significant detection kit elution where the IHC detection was weaker than the control slide without amplification. Sodium chloride addition decreased detection kit elution where [NaCl] ≥1.0 M with RbAntiHRP IHC detection were determined to be roughly equivalent to the control standard slides by pathologist evaluation.

Example 4—Temperature Versus Reagent pH Variation on Alkaline Phosphatase Inhibition/Inactivation The Ventana ultraView Universal Alkaline Phosphatase Red IHC Detection kit was used during this study. The desired enzyme inactivation step was inserted into the general protocol described above after the ultraVIEW Universal AP Multimer (VMSI, #253-4327) detection step and before ultraVIEW Universal AP Red chromogen deposition. The enzyme inactivation step was performed at variable temperatures and incubation times. Antigen retrieval was performed using Ventana CC1 for 8 minutes. The Ventana Confirm MsAntiCD20 (Clone L26, VMSI #760-2531) primary antibody was used at about 37° C. for about 16 minutes. Calf intestinal alkaline phosphatase inactivation/denaturation pH dependence was verified as performed with HRP through treatments with about 1M citrate buffer with pH=about 1.5 to about 3.0 at about 0.5 pH unit increments. An increase in reagent pH caused an increase in the puddle pH to which the tissue was exposed (Reagent pH/Approximate puddle pH: about 1.5/about 2.0; about 2.0/about 2.5 to 2.75; about 2.5/about 3.0 to 2.25; about 3.0/about 3.5 to 4.0) as explained above (see Example 1). The AP enzyme inactivation efficiency decreased as the puddle pH increased. Only 1 M citrate bases (pH=about 1.5 and about 2.0) demonstrated full AP enzyme activity loss at about 37° C. in about 12 min. The AP Red IHC staining intensity and percent staining cells increased as the reagent pH was increased. Higher intensity AP Red staining was observed using 1 M citrate bases at pH=about 2.0 than at a pH=about 1.5 for shorter enzyme inactivation steps at about 37° C. Temperature elevation to about 41° C. allowed enzyme inactivation in about 4 min at about 41° C. using the about 1 M citrate base (pH=about 1.5). The about 1 M citrate base (pH=about 2.0) required about 8 min at about 41° C.

Example 5—Additive Effects on the Inactivation of Alkaline Phosphatase

This was performed as discussed in Example 4. The enzyme inactivation compositions used for peroxidase inactivation (see Example 3 above) were tested on alkaline phosphatase inactivation to access if they would increase the inactivation efficiency. No significant advantage was observed for the addition of hydrogen peroxide or sodium azide. Sodium chloride addition reduced the temperature required for alkaline phosphatase inactivation from about 41° C. to about 37° C. at about 4 min.

Example 6—Enzyme Inactivation/Method Comparison Study

The enzyme inactivation composition leading candidates were compared to prior art enzyme inactivation (and detection elution) methods that are compatible with and currently utilized on VMSI Benchmark XT and Ultra platforms (See Table 1). Studies were performed to compare their impact on enzyme inactivation, elution efficiency, DAB chromogen hue/stability, tissue antigen detection signal intensity, and counterstain appearance. The top five leading compositions/methods were then tested for their effect on tissue morphology with tour of tumor (TOT) and tour of body (TMB) tissue slides.

TABLE 1

Enzyme inactivation/detection elution compositions and methods compared to disclosed leading enzyme inactivation composition candidates. (X dp = X reagent dispenses/drops, JD = jet drain protocol)

Enzyme Inactivation Methods (Detection Elution Methods)

A: 1 M Citrate base (pH = 1.5) (4 min, 37° C.)
B: 1 M Citrate (pH = 1.5), 1.0% $H_2O_2$, 0.08% $NaN_3$ (4 min, 37° C.)
C: 1 M Citrate (pH = 1.5), 0.5% $H_2O_2$, 0.08% $NaN_3$ (4 min, 37° C.)
D: 1 M Citrate (pH = 2.0), 1.0% $H_2O_2$, 0.08% $NaN_3$ (4 min, 37° C.)
E: 1 M Citrate (pH = 1.5), 1.0% $H_2O_2$, 0.5 M NaCl, 0.08% $NaN_3$ (4 min, 37° C.)
F: 1 M Citrate (pH = 1.5), 1.0% $H_2O_2$, 0.75 M NaCl, 0.08% $NaN_3$ (4 min, 37° C.)
G: 1 M Citrate (pH = 1.5), 1.0% $H_2O_2$, 1.0 M NaCl, 0.08% $NaN_3$ (4 min, 37° C.)
H: Ventana PO Inhibitor (3 × 4 min, 45° C.)
I: Ventana PO Inhibitor (1 × 12 min, 45° C.)
J: Ventana DISCO Inhibitor (3 × 12 min, 37° C.)
K: Ventana CC1 antigen retrieval (8 min, 95° C.)
L: Ventana CC2 antigen retrieval (8 min, 95° C.)
M: Heat denaturation (Reaction Buffer, 4 min, 90° C.)
N: 25 mM Glycine (pH = 2.0), 1.0% SDS (5 dp, JD, 32 min, 50° C.)
O: 25 mM Citrate (pH = 2.0), 1.0% SDS (5 dp, JD, 32 min, 50° C.)
P: 25 mM Glycine (pH = 2.0), 1.0% SDS (3 dp, JD, 2 × 8 min, 50° C.)
Q: 25 mM Citrate (pH = 2.0), 1.0% SDS (3 dp, JD, 2 × 8 min, 50° C.)

Example 7—Peroxidase Inhibition/Inactivation Composition/Method Comparison

The enzyme inactivation compositions in Table 1 were screened for their ability to inactivate endogenous and detection kit peroxidase activity using OptiView DAB IHC detection (VMSI #760-700) with CD20 (Clone L26, VMSI #760-2531) on normal tonsil tissue (about 8 min CC1, about 16 min CD20). Each of the enzyme inactivation compositions was performed in an OptiView DAB IHC assay after an enzyme conjugate incubation step and prior to the DAB chromogen detection (1° Ab Incubation—HRP Multimer Incubation—Enzyme Inactivation/Detection Elution—Std. DAB Detection). The results are summarized in Table 2 and demonstrated in FIG. 1.

Figure 1A:
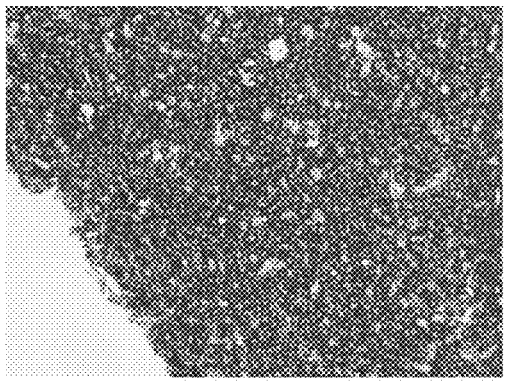
FIGS. 1A through 1HH set forth a sequence of images that show the effect of different enzyme inactivation compositions and methods on peroxidase inactivation after application to a biological sample.
Figure 1B:
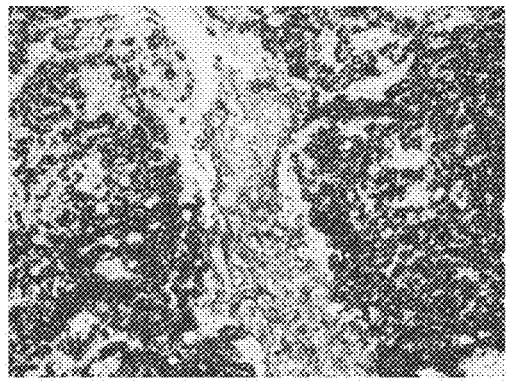
Figure 1C:
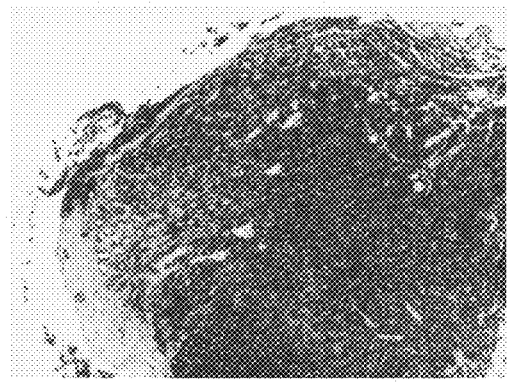
Figure 1D:
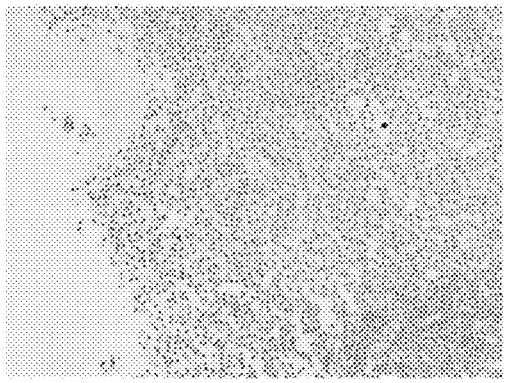
Figure 1E:
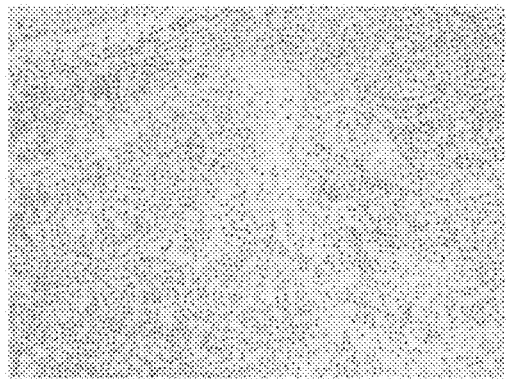
Figure 1F:
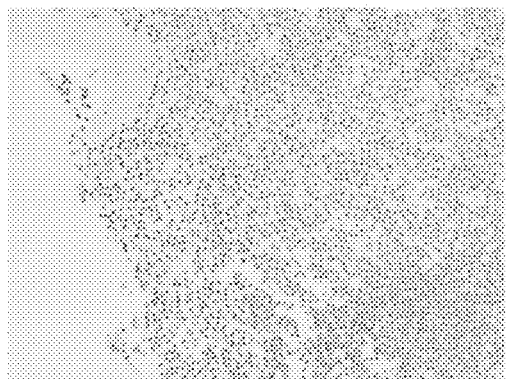
Figure 1G:
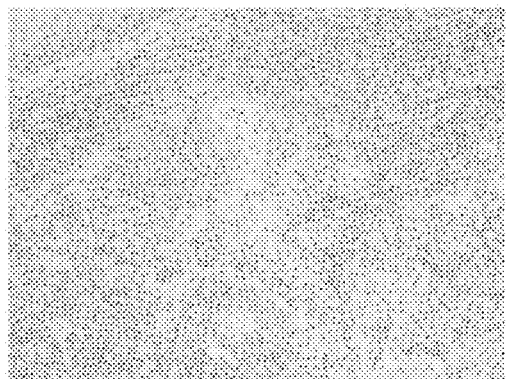
Figure 1H:
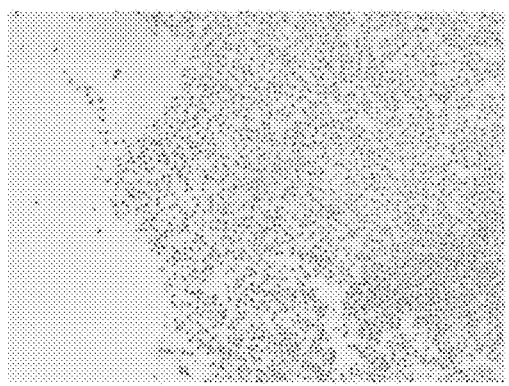
Figure 1I:
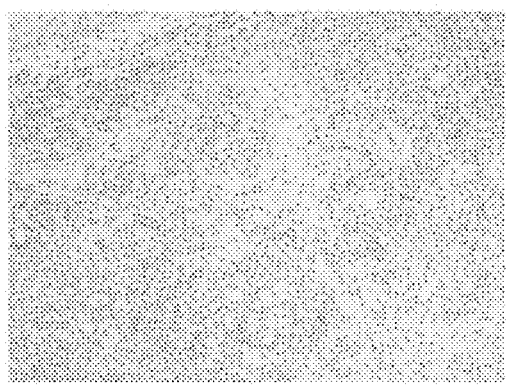
FIG. 1I depicts a tissue sample treated with Composition C (see Table 1).
Figure 1K:
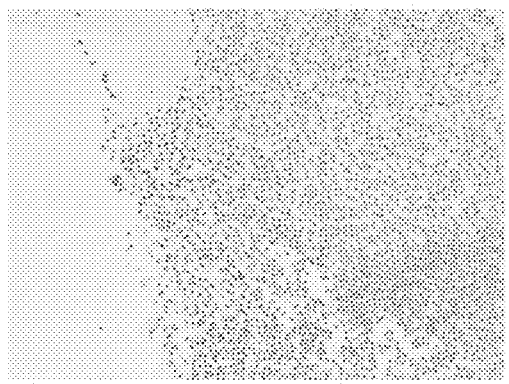
FIG. 1K depicts a tissue sample treated with Composition D (see Table 1).
Figure 1J:
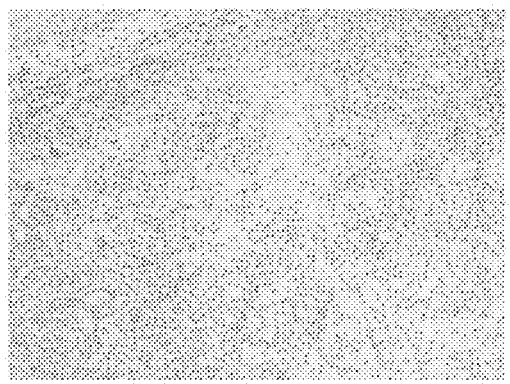
FIG. 1J depicts a tissue sample treated with Composition D (see Table 1).
Figure 1L:
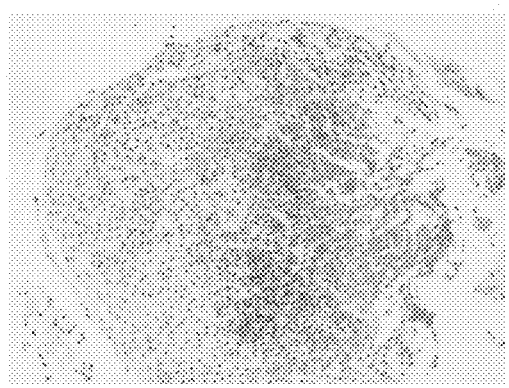
FIG. 1L depicts a tissue sample treated with Composition E (see Table 1).
Figure 1M:
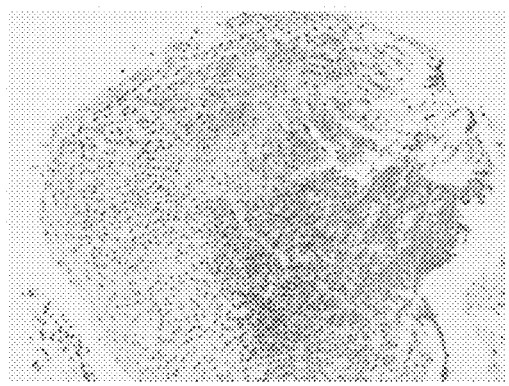
FIG. 1M depicts a tissue sample treated with Composition F (see Table 1).
Figure 1N:
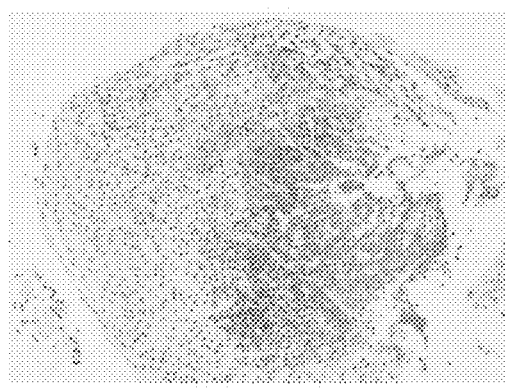
FIG. 1N depicts a tissue sample treated with Composition G (see Table 1).
Figure 1O:
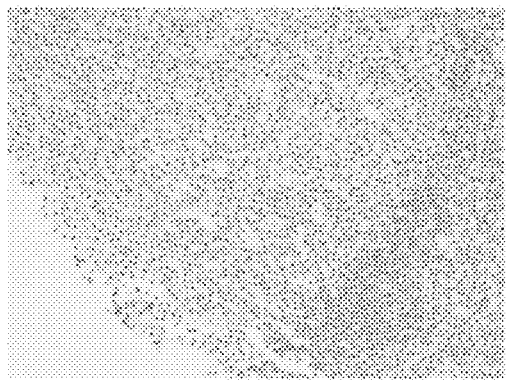
FIG. 1O depicts a tissue sample treated with Composition H (see Table 1).
Figure 1P:
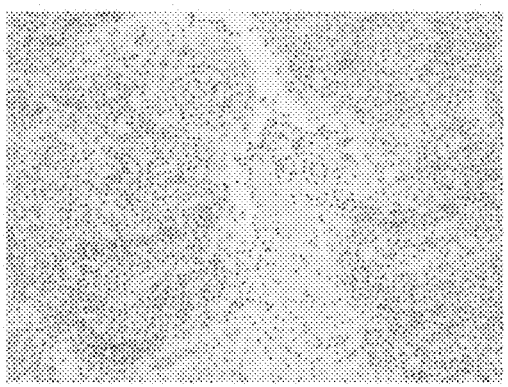
FIG. 1P depicts a tissue sample treated with Composition H (see Table 1).
Figure 1Q:
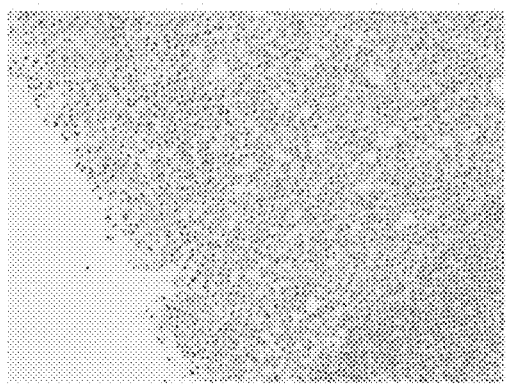
FIG. 1Q depicts a tissue sample treated with Composition I (see Table 1).
Figure 1R:
FIG. 1R depicts a tissue sample treated with Composition I (see Table 1).
Figure 1S:
FIG. 1S depicts a tissue sample treated with Composition J (see Table 1).
Figure 1T:
FIG. 1T depicts a tissue sample treated with Composition J (see Table 1).
Figure 1U:
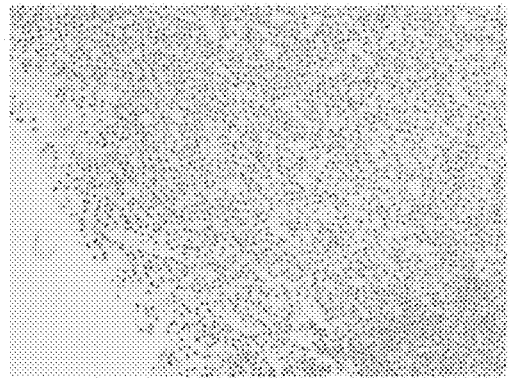
FIG. 1U depicts a tissue sample treated with Composition K (see Table 1).
Figure 1V:
FIG. 1V depicts a tissue sample treated with Composition K (see Table 1).
Figure 1W:
FIG. 1W depicts a tissue sample treated with Composition L (see Table 1).
Figure 1X:
FIG. 1X depicts a tissue sample treated with Composition L (see Table 1).
Figure 1Y:
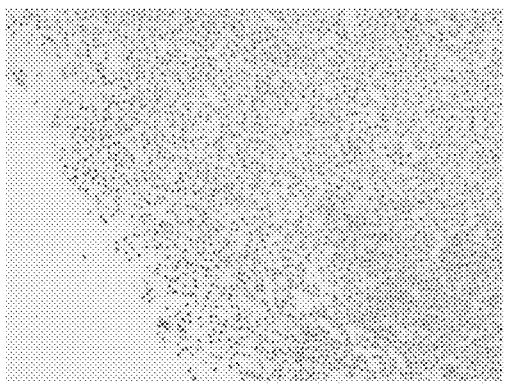
FIG. 1Y depicts a tissue sample treated with Composition M (see Table 1).
Figure 1Z:
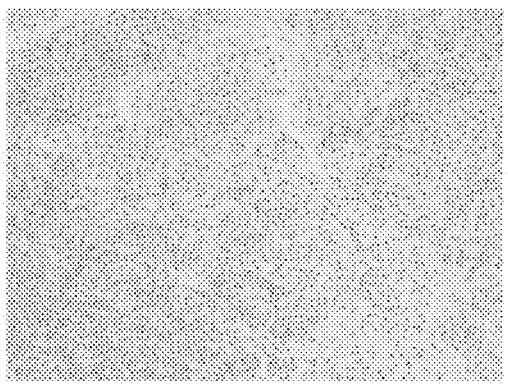
FIG. 1Z depicts a tissue sample treated with Composition M (see Table 1).
Figure 1A:
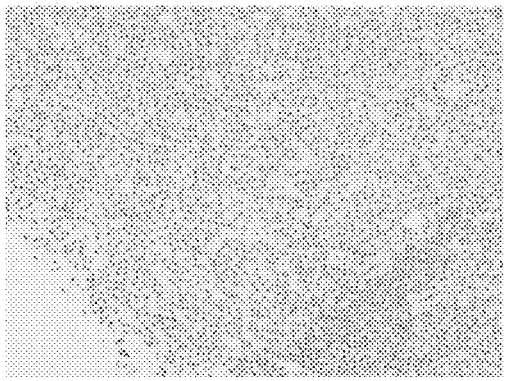
Figure 1B:
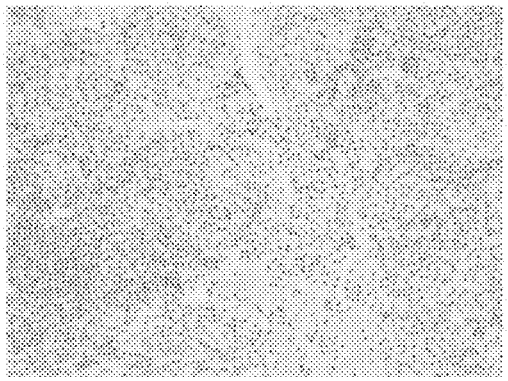
Figure 1C:
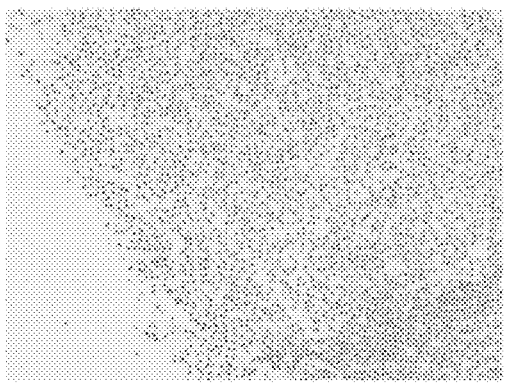
Figure 1D:
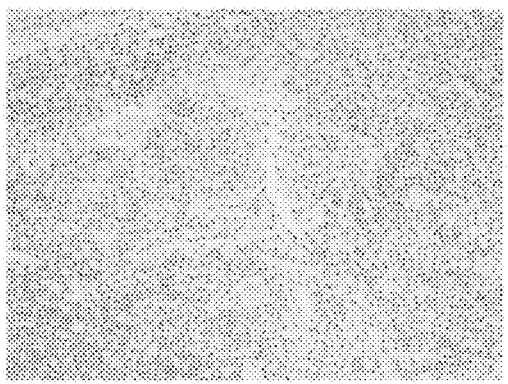
Figure 1E:
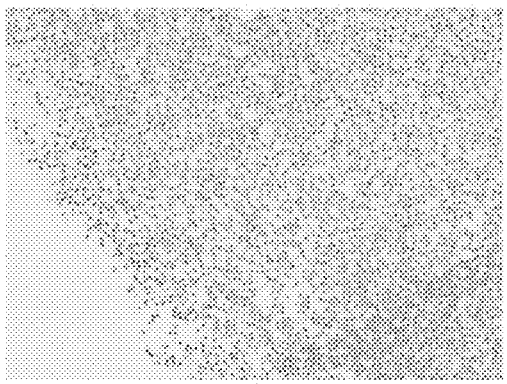
Figure 1F:
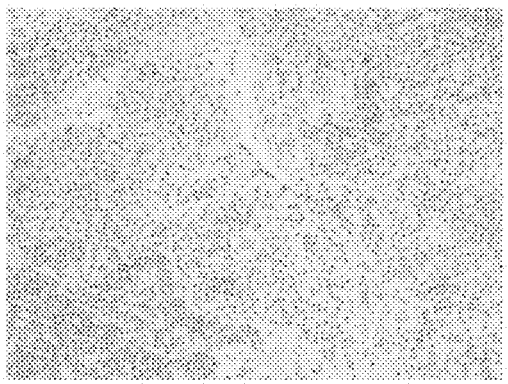

FIGS. 1A and 1B IHC DAB depict standard tissue samples with no treatment—CD20, tonsil (8 min CC1, 16 min CD20), where the images were captured at 20× magnification; FIG. 1C depicts IHC DAB Standard with no treatment—CD20, tonsil (8 min CC1, 16 min CD20); FIGS. 1D and 1E depict tissue samples treated with Composition A; FIGS. 1F and 1G depict tissue samples treated with composition B; FIGS. 1H and 1I depict tissue samples treated with Composition C; FIGS. 1K and 1J depict tissue samples treated with Composition D; FIG. 1L depicts a tissue sample treated with Composition E; FIG. 1M depicts a tissue sample treated with Composition F; FIG. 1N depicts a tissue sample treated with Composition G; FIGS. 1O and 1P depict tissue samples treated with Composition H; FIGS. 1Q and 1R depict tissue samples treated with Composition I; FIGS. 1S and 1T depict tissue samples treated with Composition J; FIGS. 1U and 1V depict tissue samples treated with Composition K; FIGS. 1W and 1X depict tissue samples treated with Composition L; FIGS. 1Y and 1Z depict tissue samples treated with Composition M; FIGS. 1AA and 1BB depict tissue samples treated with Composition N; FIGS. 1CC and 1DD depict tissue samples treated with Composition O; FIGS. 1EE and 1FF depict tissue samples treated with Composition P; and FIGS. 1GG and 1HH depict tissue samples treated with Composition Q.

Residual HRP enzyme activity (detection kit) was only observed for compositions I>J>>H≈A (ranked order). All other compositions completely inhibited HRP enzyme activity. Residual endogenous peroxidase activity was observed for all compositions except for methods B to G. The leading candidates from this comparison study were compositions B through G.

TABLE 2

Enzyme inactivation/detection elution compositions and methods compared to disclosed leading enzyme inactivation composition candidates. (X dp = X reagent dispenses/drops, JD = jet drain protocol)

| Enzyme Inactivation Methods (Detection Elution Methods) | Detection Kit Peroxidase Inactivation | Endogenous Peroxidase Inactivation |
|---|---|---|
| A: 1 M Citrate base (pH = 1.5) (4 min, 37° C.) | Residual HRP activity observed | Endogenous peroxidase activity observed |
| B: 1 M Citrate (pH = 1.5), 1.0% $H_2O_2$, 0.08% $NaN_3$ (4 min, 37° C.) | No HRP activity observed | No endogenous peroxidase activity observed |
| C: 1 M Citrate (pH = 1.5), 0.5% $H_2O_2$, 0.08% $NaN_3$ (4 min, 37° C.) | No HRP activity observed | No endogenous peroxidase activity observed |
| D: 1 M Citrate (pH = 2.0), 1.0% $H_2O_2$, 0.08% $NaN_3$ (4 min, 37° C.) | No HRP activity observed | No endogenous peroxidase activity observed |
| E: 1 M Citrate (pH = 1.5), 1.0% $H_2O_2$, 0.5 M NaCl, 0.08% $NaN_3$ (4 min, 37° C.) | No HRP activity observed | No endogenous peroxidase activity observed |
| F: 1 M Citrate (pH = 1.5), 1.0% $H_2O_2$, 0.75 M NaCl, 0.08% $NaN_3$ (4 min, 37° C.) | No HRP activity observed | No endogenous peroxidase activity observed |
| G: 1 M Citrate (pH = 1.5), 1.0% $H_2O_2$, 1.0 M NaCl, 0.08% $NaN_3$ (4 min, 37° C.) | No HRP activity observed | No endogenous peroxidase activity observed |
| H: Ventana PO Inhibitor (3 × 4 min, 45° C.) | Residual HRP activity observed | Endogenous peroxidase activity observed |
| I: Ventana PO Inhibitor (1 × 12 min, 45° C.) | Residual HRP activity observed | Endogenous peroxidase activity observed |
| J: Ventana DISCO Inhibitor (3 × 12 min, 37° C.) | Residual HRP activity observed | Endogenous peroxidase activity observed |
| K: Ventana CC1 antigen retrieval (8 min, 95° C.) | No HRP activity observed | Endogenous peroxidase activity observed |
| L: Ventana CC2 antigen retrieval (8 min, 95° C.) | No HRP activity observed | Endogenous peroxidase activity observed |
| M: Heat denaturation (Reaction Buffer - 4 min, 90° C.) | No HRP activity observed | Endogenous peroxidase activity observed |
| N: 25 mM Glycine (pH = 2.0), 1.0% SDS (5 dp, JD, 32 min, 50° C.) | No HRP activity observed | Endogenous peroxidase activity observed |
| O: 25 mM Citrate (pH = 2.0), 1.0% SDS (5 dp, JD, 32 min, 50° C.) | No HRP activity observed | Endogenous peroxidase activity observed |
| P: 25 mM Glycine (pH = 2.0), 1.0% SDS (3 dp, JD, 2 × 8 min, 50° C.) | No HRP activity observed | Endogenous peroxidase activity observed |

TABLE 2-continued

Enzyme inactivation/detection elution compositions and methods compared to disclosed leading enzyme inactivation composition candidates. (X dp = X reagent dispenses/drops, JD = jet drain protocol)

| Enzyme Inactivation Methods (Detection Elution Methods) | Detection Kit Peroxidase Inactivation | Endogenous Peroxidase Inactivation |
|---|---|---|
| Q: 25 mM Citrate (pH = 2.0), 1.0% SDS (3 dp, JD, 2 × 8 min, 50° C.) | No HRP activity observed | Endogenous peroxidase activity observed |

Example 8—Alkaline Phosphatase Inhibition/Inactivation Composition/Method Comparison The enzyme inactivation compositions in Table 1 were screened for their ability to inactivate endogenous and detection kit alkaline phosphatase activity using ultraView AP Red IHC detection kit (VMSI #760-501) staining of CD20 (Clone L26, VMSI #760-2531) on tonsil (about 8 min CC1, about 16 min CD20). Each of the enzyme inactivation compositions was tested in the IHC assay after an enzyme conjugate incubation step and prior to the AP Red chromogen detection (1° Ab Incubation—HRP Multimer Incubation—Enzyme Inactivation/Detection Elution—Std. AP Red Detection). The results are summarized in Table 3 and FIG. 2.

Figure 2A:
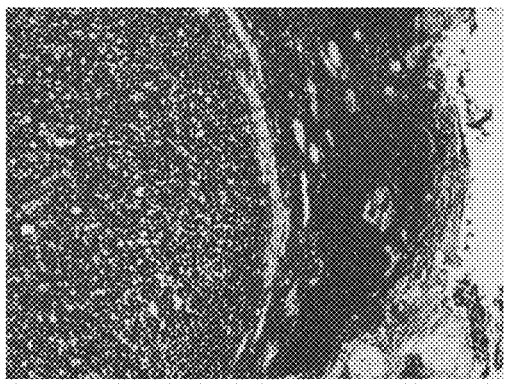
FIGS. 2A through 2S set forth a sequence of images that show the effect of different enzyme inactivation compositions and methods on alkaline phosphatase inactivation after application to a biological sample.
Figure 2B:
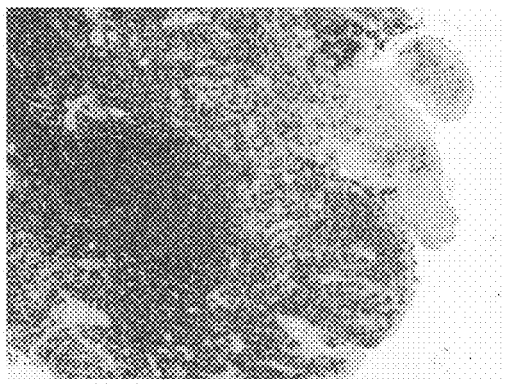
FIG. 2B depicts IHC AP Red Standard with no treatment—CD20, tonsil (8 min CC1, 16 min CD20) (Representative images at 10×).
Figure 2C:
FIG. 2C depicts a tissue sample treated with Composition A (see Table 2).
Figure 2D:
FIG. 2D depicts a tissue sample treated with Composition B (see Table 2).
Figure 2E:
FIG. 2E depicts a tissue sample treated with Composition C (see Table 2).
Figure 2F:
FIG. 2F depicts a tissue sample treated with Composition D (see Table 2).
Figure 2G:
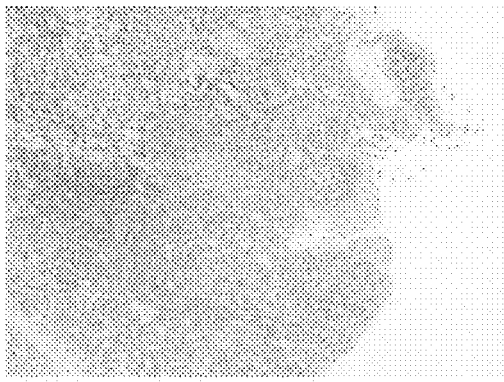
FIG. 2G depicts a tissue sample treated with Composition E (see Table 2).
Figure 2H:
FIG. 2H depicts a tissue sample treated with Composition F (see Table 2).
Figure 2I:
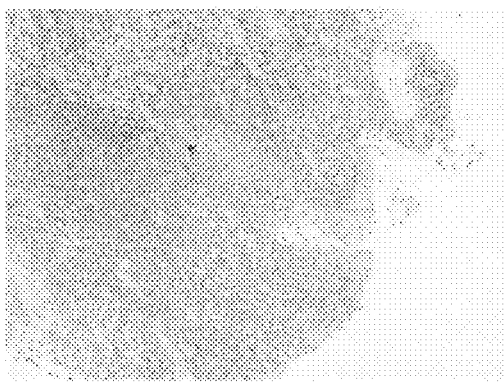
FIG. 2I depicts a tissue sample treated with Composition G (see Table 2).
Figure 2J:
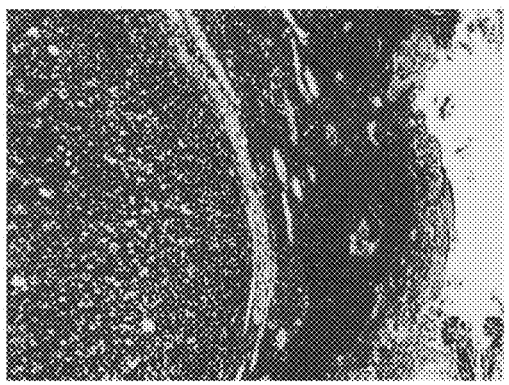
FIG. 2J depicts a tissue sample treated with Composition H (see Table 2).
Figure 2K:
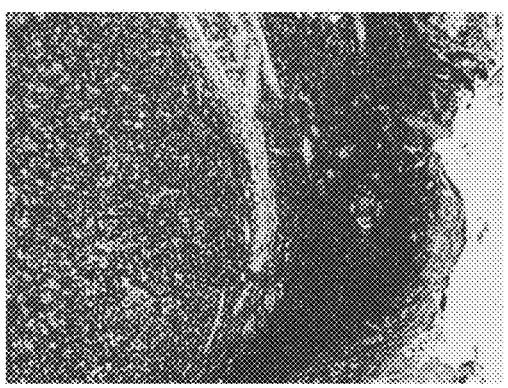
FIG. 2K depicts a tissue sample treated with Composition I (see Table 2).
Figure 2L:
FIG. 2L depicts a tissue sample treated with Composition J (see Table 2).
Figure 2M:
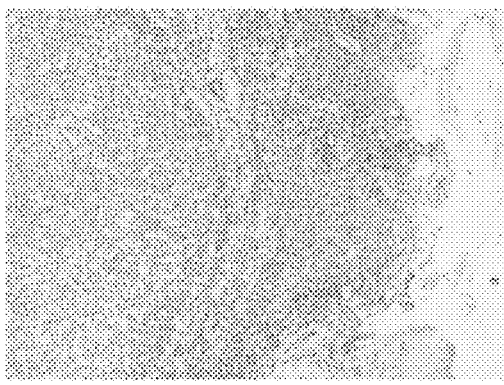
FIG. 2M depicts a tissue sample treated with Composition K (see Table 2).
Figure 2N:
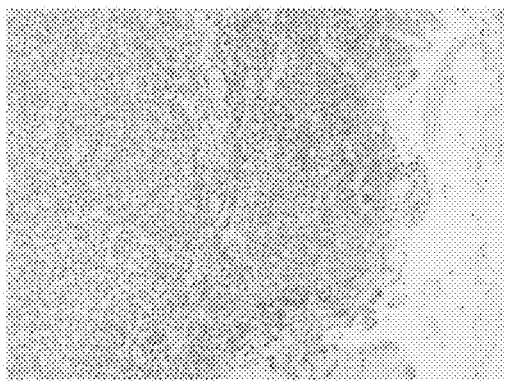
FIG. 2N depicts a tissue sample treated with Composition L (see Table 2).
Figure 2O:
FIG. 2O depicts a tissue sample treated with Composition M (see Table 2).
Figure 2P:
FIG. 2P depicts a tissue sample treated with Composition N (see Table 2).
Figure 2Q:
FIG. 2Q depicts a tissue sample treated with Composition O (see Table 2).
Figure 2R:
FIG. 2R depicts a tissue sample treated with Composition P (see Table 2).
Figure 2S:

FIG. 2A depicts an IHC AP Red Standard with no treatment—CD20, tonsil (8 min CC1, 16 min CD20) (Representative images at 10×); FIG. 2B depicts IHC AP Red Standard with no treatment—CD20, tonsil (8 min CC1, 16 min CD20) (Representative images at 10×); FIG. 2C depicts a tissue sample treated with Composition A; FIG. 2D depicts a tissue sample treated with Composition B; FIG. 2E depicts a tissue sample treated with Composition C; FIG. 2F depicts a tissue sample treated with Composition D; FIG. 2G depicts a tissue sample treated with Composition E; FIG. 2H depicts a tissue sample treated with Composition F; FIG. 2I depicts a tissue sample treated with Composition G. FIG. 2J depicts a tissue sample treated with Composition H; FIG. 2K depicts a tissue sample treated with Composition I; FIG. 2L depicts a tissue sample treated with Composition J; FIG. 2M depicts a tissue sample treated with Composition K; FIG. 2N depicts a tissue sample treated with Composition L; FIG. 2O depicts a tissue sample treated with Composition M; FIG. 2P depicts a tissue sample treated with Composition N; FIG. 2Q depicts a tissue sample treated with Composition O; FIG. 2R depicts a tissue sample treated with Composition P; and FIG. 2S depicts a tissue sample treated with Composition Q.

Residual AP enzyme activity (detection kit) was only observed for compositions H-J. Compositions J showed increased nonspecific AP Red chromogen staining surrounding the tissue. All other compositions completely inhibited AP enzyme activity. The leading candidates form this comparison study were compositions A through G and K through Q.

TABLE 3

Enzyme inactivation/detection elution compositions and methods compared to disclosed leading enzyme inactivation composition candidates. (X dp = X reagent dispenses/drops, JD = jet drain protocol)

| Enzyme Inactivation Methods (Detection Elution Methods) | Detection Kit AP Inactivation |
|---|---|
| A: 1 M Citrate base (pH = 1.5) (4 min, 37° C.) | No AP activity observed |
| B: 1 M Citrate (pH = 1.5), 1.0% $H_2O_2$, 0.08% $NaN_3$ (4 min, 41° C.) | No AP activity observed |
| C: 1 M Citrate (pH = 1.5), 0.5% $H_2O_2$, 0.08% $NaN_3$ (4 min, 41° C.) | No AP activity observed |
| D: 1 M Citrate (pH = 2.0), 1.0% $H_2O_2$, 0.08% $NaN_3$ (4 min, 41° C.) | No AP activity observed |
| E: 1 M Citrate (pH = 1.5), 1.0% $H_2O_2$, 0.5 M NaCl, 0.08% $NaN_3$ (4 min, 37° C.) | No AP activity observed |
| F: 1 M Citrate (pH = 1.5), 1.0% $H_2O_2$, 0.75 M NaCl, 0.08% $NaN_3$ (4 min, 37° C.) | No AP activity observed |
| G: 1 M Citrate (pH = 1.5), 1.0% $H_2O_2$, 1.0 M NaCl, 0.08% $NaN_3$ (4 min, 37° C.) | No AP activity observed |
| H: Ventana PO Inhibitor (3 × 4 min, 45° C.) | Residual AP activity observed |
| I: Ventana PO Inhibitor (1 × 12 min, 45° C.) | Residual AP activity observed |
| J: Ventana DISCO Inhibitor (3 × 12 min, 37° C.) | Residual AP activity observed |
| K: Ventana CC1 antigen retrieval (8 min, 95° C.) | No AP activity observed |
| L: Ventana CC2 antigen retrieval (8 min, 95° C.) | No AP activity observed |
| M: Heat denaturation (Reaction Buffer - 4 min, 90° C.) | No AP activity observed |
| N: 25 mM Glycine (pH = 2.0), 1.0% SDS (5 dp, JD, 32 min, 50° C.) | No AP activity observed |
| O: 25 mM Citrate (pH = 2.0), 1.0% SDS (5 dp, JD, 32 min, 50° C.) | No AP activity observed |
| P: 25 mM Glycine (pH = 2.0), 1.0% SDS (3 dp, JD, 2 × 8 min, 50° C.) | No AP activity observed |
| Q: 25 mM Citrate (pH = 2.0), 1.0% SDS (3 dp, JD, 2 × 8 min, 50° C.) | No AP activity observed |

Example 9—Enzyme Inactivation Versus Detection Kit Elusion Comparison

The enzyme inactivation methods in Table 1 were screened for their ability to elute detection kits following enzyme peroxidase inactivation using OptiView DAB IHC detection staining (VMSI #760-700) of CD20 (Clone L26, VMSI #760-2531) on tonsil (about 8 min CC1, about 16 min CD20) or bcl2 (Clone 124, VMSI #790-4464) on tonsil (64 min CC1, 32 min bcl2), RbAntiHRP detection (Jackson #323-005-021) (at about 37° C. for about 16 minutes) and ultraView HRP Multimer (VMSI, #253-4290)(at about 37° C. for about 8 min). Each of the enzyme inactivation compositions was tested in the IHC assay after the OptiView HRP Multimer incubation step and prior to RbAntiHRP detection (1° Ab Incubation—OptiView 2° Incubation—OptiView HRP Multimer Incubation—Enzyme Inactivation/Detection Elution—RbAntiHRP Incubation—ultraView HRP Multimer Incubation—Std. DAB Detection). Complete detection kit elution was not observed using any treatment method (see FIG. 3).

Figure 3A:
FIGS. 3A through 3V set forth a sequence of images that show comparisons between enzyme inactivation versus detection kit elution after different enzyme inactivation compositions and methods were applied to a biological sample.
Figure 3B:
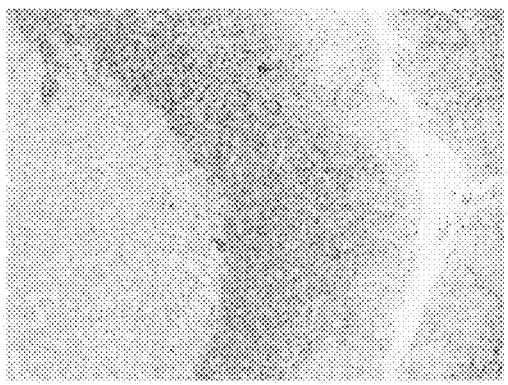
FIG. 3B depicts tissue stained with IHC DAB Standard with no treatment, bcl2, tonsil (64 min CC1, 32 min bcl2).
Figure 3C:
FIG. 3C depicts tissue stained with IHC DAB Standard with RbAntiHRP/ultraView Detection, CD20, tonsil (8 min CC1, 16 min CD20).
Figure 3D:
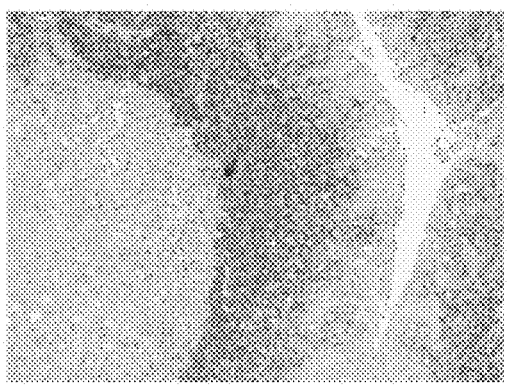
FIG. 3D depicts tissue stained with IHC DAB Standard with RbAntiHRP/ultraView Detection, bcl2, tonsil (64 min CC1, 32 min bcl2).
Figure 3E:
FIG. 3E depicts tissue samples treated with Composition A, CD20, tonsil (8 min CC1, 16 min CD20) (see Table 3).
Figure 3F:
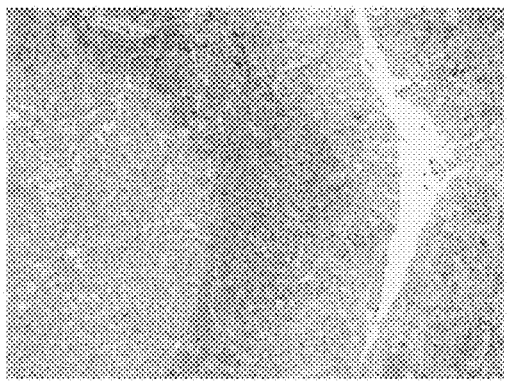
FIG. 3F depicts tissue samples treated with Composition A, bcl2, tonsil (64 min CC1, 32 min bcl2)) (see Table 3).
Figure 3G:
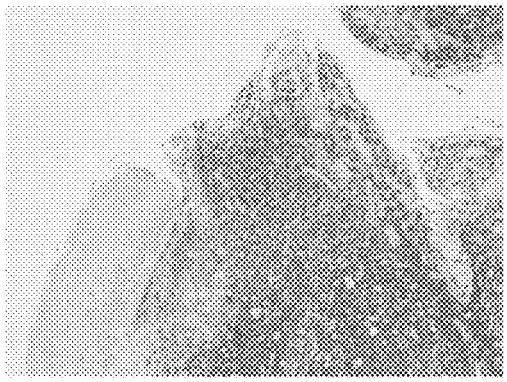
FIG. 3G depicts a tissue sample treated with Composition B (see Table 3).
Figure 3H:
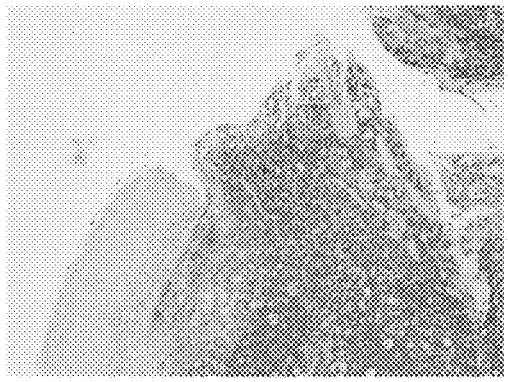
FIG. 3I depicts a tissue sample treated with Composition D (see Table 3).
FIG. 3J depicts a tissue sample treated with Composition E (see Table 3).
FIG. 3K depicts a tissue sample treated with Composition F (see Table 3).
FIG. 3L depicts a tissue sample treated with Composition G (see Table 3).
FIG. 3M depicts a tissue sample treated with Composition H (see Table 3).
FIG. 3N depicts a tissue sample treated with Composition I (see Table 3).
FIG. 3O depicts a tissue sample treated with Composition J (see Table 3).
FIG. 3P depicts a tissue sample treated with Composition K (see Table 3).
FIG. 3Q depicts a tissue sample treated with Composition L (see Table 3).
FIG. 3R depicts a tissue sample treated with Composition M (see Table 3).
FIG. 3S depicts a tissue sample treated with Composition N (see Table 3).
FIG. 3T depicts a tissue sample treated with Composition O (see Table 3).
FIG. 3U depicts a tissue sample treated with Composition P (see Table 3).
Figure 3I:
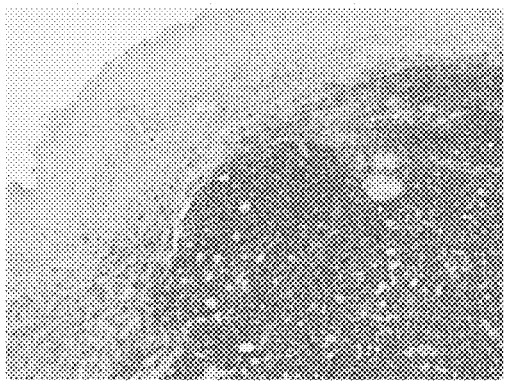
Figure 3J:
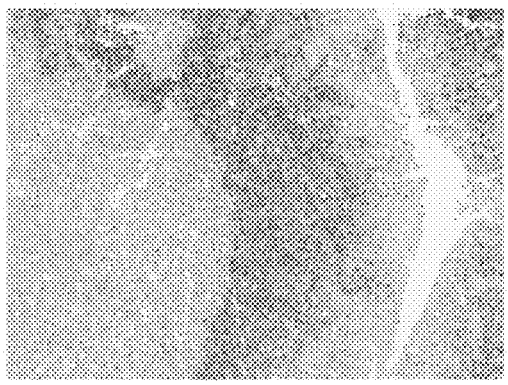
Figure 3K:
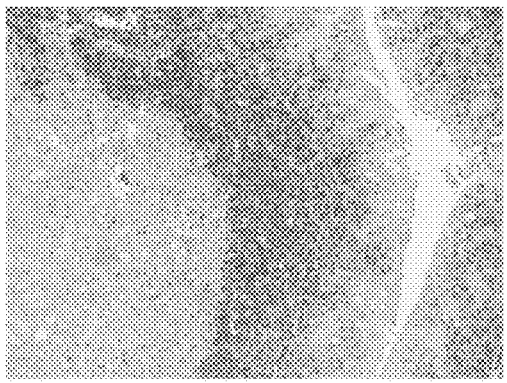
Figure 3L:
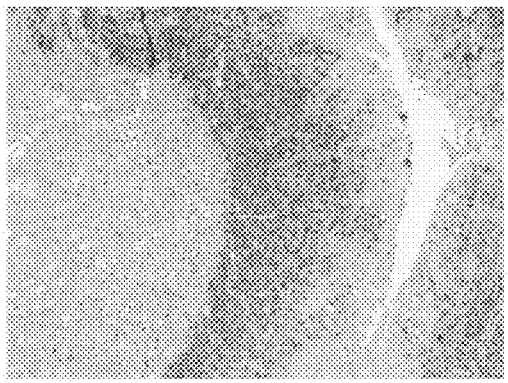
Figure 3M:
Figure 3N:
Figure 3O:
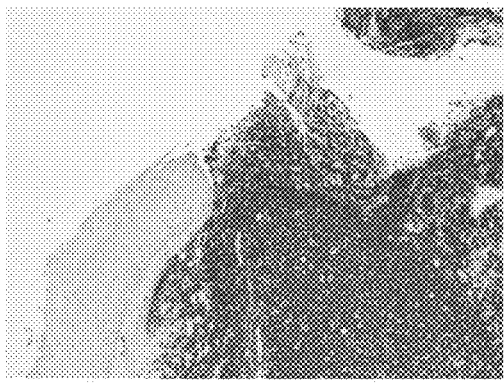
Figure 3P:
Figure 3Q:
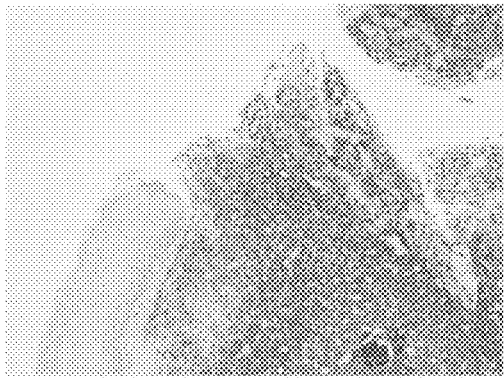
Figure 3R:
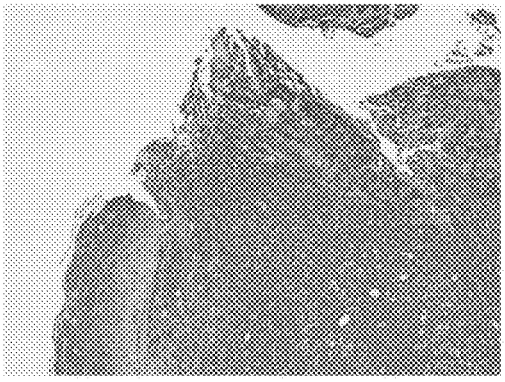
Figure 3S:
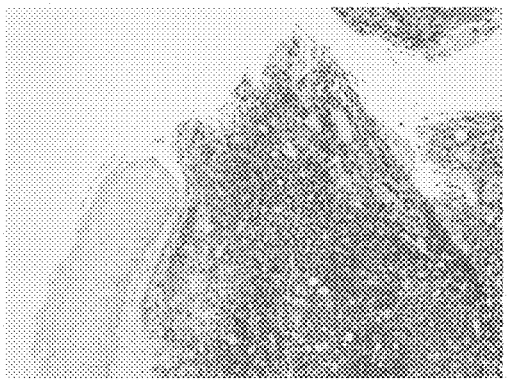
Figure 3T:
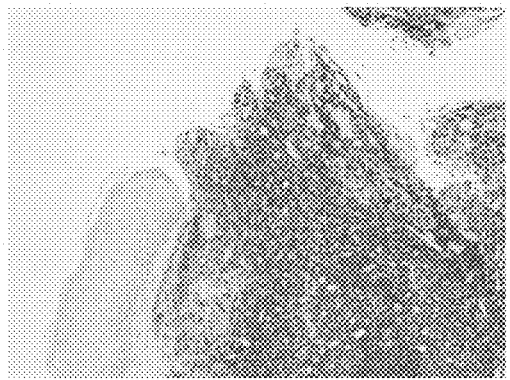
Figure 3U:
Figure 3V:

FIGS. 3A and 3B depict tissue stained with IHC DAB Standard with no treatment (FIG. 3A CD20, tonsil (8 min CC1, 16 min CD20); FIG. 3B bcl2, tonsil (64 min CC1, 32 min bcl2. FIGS. 3A and 3B are for only compositions A, and E to G. Representative images are at 10×. FIGS. 3C and 3D depict tissue stained with IHC DAB Standard with RbAntiHRP/ultraView Detection (FIG. 3C is CD20, tonsil (8 min CC1, 16 min CD20), while FIG. 3D is bcl2, tonsil (64 min CC1, 32 min bcl2). FIGS. 3E and 3F depict tissue samples treated with Compositions A (FIG. 3E is CD20, tonsil (8 min CC1, 16 min CD20), while FIG. 3F is bcl2, tonsil (64 min CC1, 32 min bcl2)); FIG. 3G depicts a tissue sample treated with Composition B; FIG. 3H depicts a tissue sample treated with Composition C; FIG. 3I depicts a tissue sample treated with Composition D; FIG. 3J depicts a tissue sample treated with Composition E; FIG. 3K depicts a tissue sample treated with Composition F; FIG. 3L depicts a tissue sample treated with Composition G; FIG. 3M depicts a tissue sample treated with Composition H; FIG. 3N depicts a tissue sample treated with Composition I; FIG. 3O depicts a tissue sample treated with Composition J; FIG. 3P depicts a tissue sample treated with Composition K; FIG. 3Q depicts a tissue sample treated with Composition L; FIG. 3R depicts a tissue sample treated with Composition M; FIG. 3S depicts a tissue sample treated with Composition N; FIG. 3T depicts a tissue sample treated with Composition O; FIG. 3U depicts a tissue sample treated with Composition P; and FIG. 3V depicts a tissue sample treated with Composition Q.

Without wishing to be bound by any particular theory, it was believed that the residual HRP enzyme may be denatured effecting the RbAntiHRP detection on tissue; however, partial elution does occur. The base citrate composition containing sodium chloride (and other salts) demonstrated lower levels of elution. Composition E with about 0.5 M NaCl still showed some detection elution. However, Compositions F and G (with about 0.75 and about 1.0 M NaCl respectively) demonstrated no noticeable change in RbAntiHRP detection relative to the standard and RbAntiHRP detection. Composition M demonstrated disruption of antibody binding; however, the detection system was nonspecifically spread across the tissue (increased nonspecific background staining). Pathologist evaluations suggested the best HRP multimer elution was achieved by compositions L>P≈Q>N≈O>A through D>>K>>M (ranked order).

Example 10—Enzyme Inactivation Composition Impact on DAB IHC Chromogen Staining

Tonsil tissue was stained for bcl2 (VMSI, #253-4290) with OptiView DAB detection (VMSI #760-700) with and without hematoxylin counterstain. A bcl2 DAB IHC model was used since the DAB stain was not overly saturated and allowed for the ability to detect subtle changes. Slides were also stained without a hematoxylin counterstain since the colocalized DAB and hematoxylin stains had been observed to increase the apparent DAB intensity. The base citrate enzyme inactivation composition [1M citrate (pH=about 1.5), about 1.0 wt % $H_2O_2$, about 0.08 wt % $NaN_3$] was added at about 37° C. for about 4 min during the IHC assay immediately after standard DAB chromogen detection (DAB/$H_2O_2$ then $CuSO_4$ toning) [HRP Multimer Incubation—Std. DAB Detection—Enzyme Inactivation Composition—Hematoxylin II Counterstaining (if used)]. The enzyme inactivation composition caused the DAB hue to shift from a chocolate or brown/red color to a brown/orange color. This DAB hue was generally observed in absence of copper DAB stain toning. An extra copper-toning step added after enzyme inactivation restored some of the DAB hue. However, the DAB staining intensity was not as strong as the standard without treatment. Similar DAB hue shifts were observed with and without hematoxylin counterstaining. The DAB hue alteration was consistently observed across low and medium expression IHC antigens. However, the same DAB hue shift was not as prominently observed in the OptiView DAB IHC staining of stronger antigens such as CD20 on tonsil due to the higher DAB stain density.

Similar experiments were performed with a sodium chloride containing citrate enzyme inactivation composition [1M Citrate (pH=about 1.5)+about 1.0 wt % $H_2O_2$+about 0.5 M NaCl+about 0.08 wt % $NaN_3$]. Sodium chloride addition minimized the DAB chromogen hue shift observed with the base citrate composition at both 1× and 4× treatments. A subtle hue shift was still caused by hydrogen peroxide that most likely impacted copper toning. However, sodium chloride addition reduced detection kit elution that reduced the apparent DAB hue shift. The difference in the DAB hue impact was believed to be minimized with the introduction of between about 0.5 to about 1.0 M sodium chloride.

Example 11—DAB IHC Staining: Enzyme Inactivation Composition/Method Impact Comparison As previously discussed in Examples 9 and 10 above, DAB stain (intensity and hue) was impacted by chromogen exposure to an enzyme inactivation composition containing hydrogen peroxide after DAB detection. The compositions caused a DAB hue to shift from a chocolate or brown/red color to a brown/orange color that is generally observed for DAB staining in absence of copper toning. An extra copper-toning step after treatment with the enzyme inactivation composition restored some of the DAB hue; however, it was not as intense as the standard without treatment. The DAB hue alteration was consistently observed across low and medium expression IHC antigens; however, the same DAB hue shift was not prominently observed in the OptiView DAB IHC staining of strong antigens due to higher DAB stain intensity.

The enzyme inactivation compositions in Table 1 were screened for their impact on OptiView DAB IHC staining of bcl2 on tonsil (about 64 min CC1, about 32 min bcl2). Each of the enzyme inactivation compositions was tested in the IHC assay after Opti View DAB chromogen deposition/copper toning. No hematoxylin counterstaining was performed to allow better assessment of DAB hue and stain intensity (1° Ab Incubation—HRP Multimer Incubation—Std. DAB Detection—Enzyme Inactivation/Detection Elution). Each enzyme inactivation method was performed 1× and 4× to examine the cumulative effect of multiple sequences that could be performed in a multiplex detection assay (see FIG. 4).

Figure 4A:
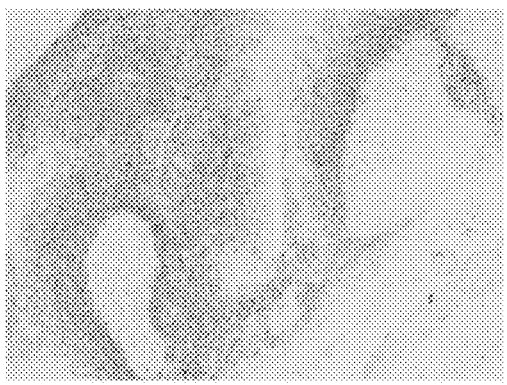
FIGS. 4A through 4HH set forth a sequence of images that show the impact of different enzyme inactivation compositions and methods on DAB chromogen intensity or hue after application to a biological sample.
Figure 4B:
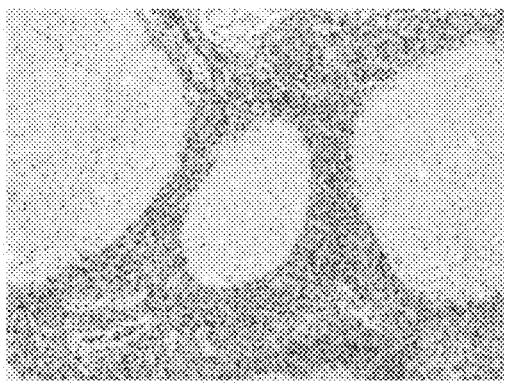
Figure 4C:
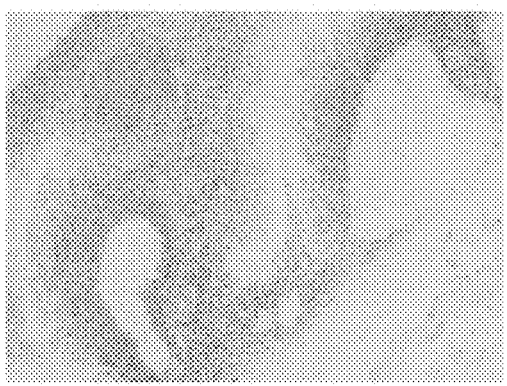
Figure 4D:
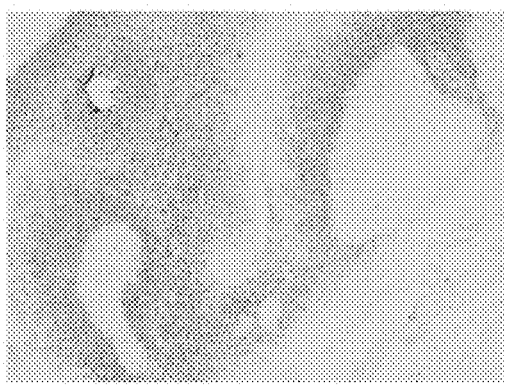
Figure 4E:
Figure 4F:
Figure 4G:
Figure 4H:
Figure 4I:
FIG. 4I depicts a tissue sample treated with Composition D.
Figure 4J:
FIG. 4J depicts a tissue sample treated with Composition D.
Figure 4K:
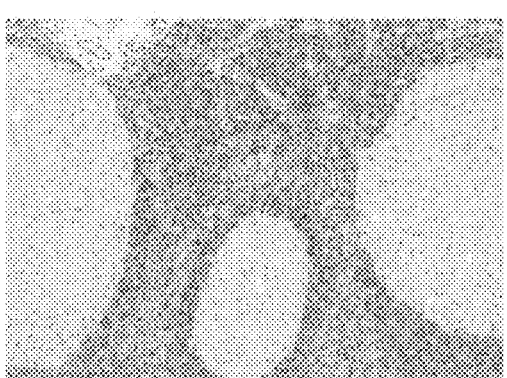
FIG. 4K depicts a tissue sample treated with Composition E.
Figure 4L:
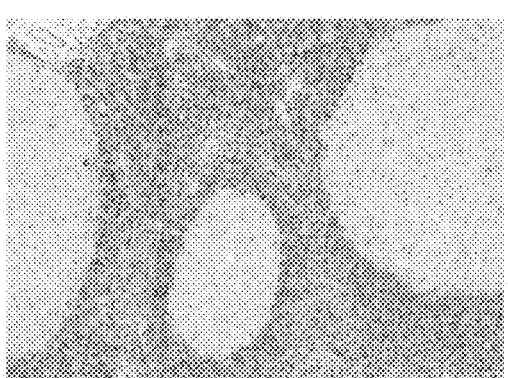
FIG. 4L depicts a tissue sample treated with Composition E.
Figure 4M:
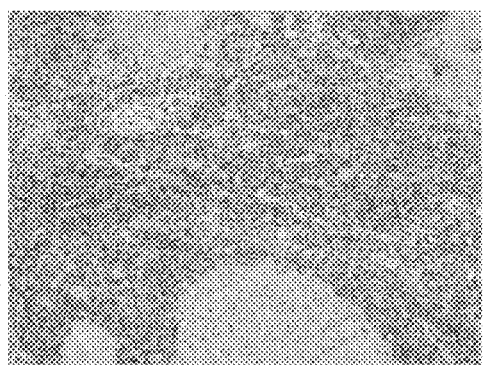
FIG. 4M depicts a tissue sample treated with Composition F.
Figure 4N:
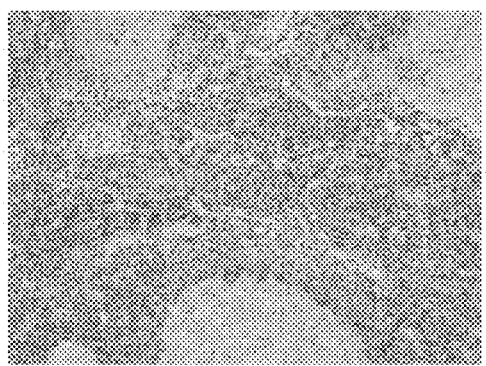
FIG. 4N depicts a tissue sample treated with Composition F.
Figure 4O:
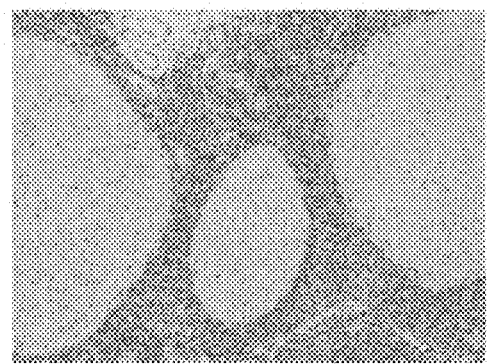
FIG. 4O depicts a tissue sample treated with Composition G.
Figure 4P:
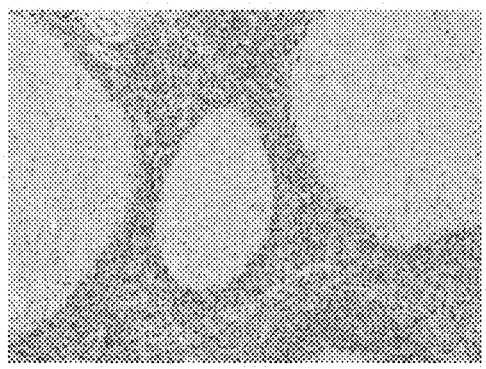
FIG. 4P depicts a tissue sample treated with Composition G.
Figure 4Q:
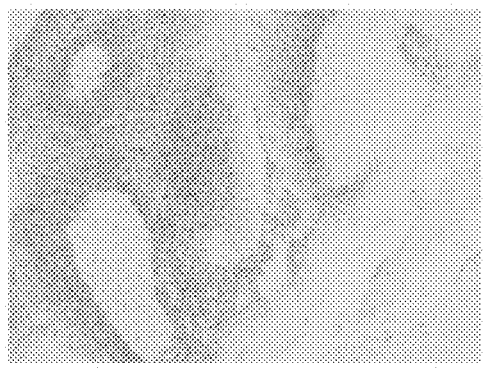
FIG. 4Q depicts a tissue sample treated with Composition H.
Figure 4R:
FIG. 4R depicts a tissue sample treated with Composition H.
Figure 4S:
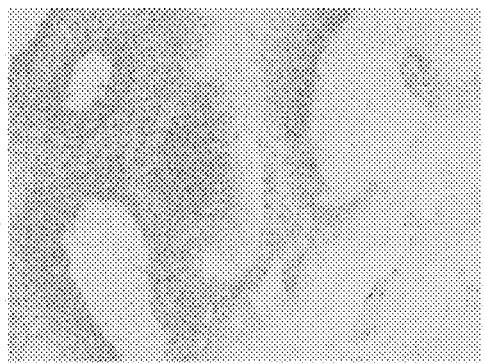
FIG. 4S depicts a tissue sample treated with Composition J.
Figure 4T:
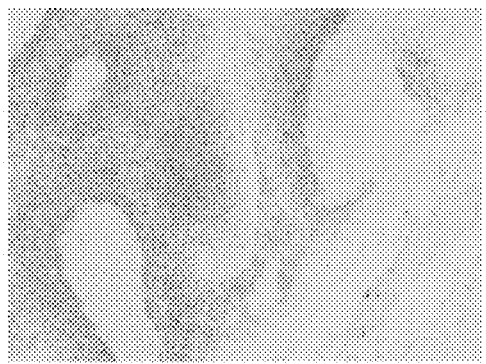
FIG. 4T depicts a tissue sample treated with Composition J.
Figure 4U:
FIG. 4U depicts a tissue sample treated with Composition K.
Figure 4V:
FIG. 4V depicts a tissue sample treated with Composition K.
Figure 4W:
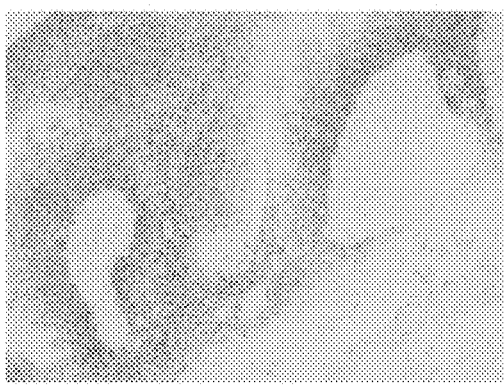
FIG. 4W depicts a tissue sample treated with Composition L.
Figure 4X:
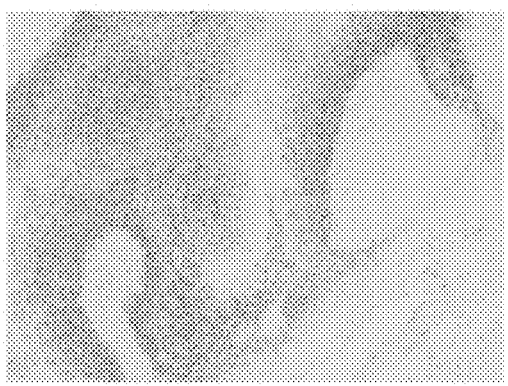
FIG. 4X depicts a tissue sample treated with Composition L.
Figure 4Y:
FIG. 4Y depicts a tissue sample treated with Composition M.
Figure 4Z:
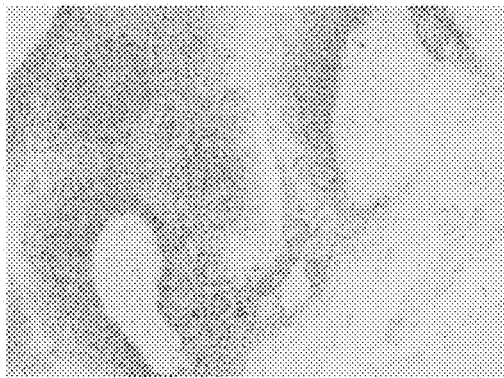
FIG. 4Z depicts a tissue sample treated with Composition M.
Figure 4A:
Figure 4B:
Figure 4C:
Figure 4D:
Figure 4E:
Figure 4F:

FIGS. 4A and 4B depict tissue stained with IHC DAB Standard with no treatment—bcl2, tonsil (64 min CC1, 32 min bcl2). (2nd reagent formulation round standard—4B—FOR ONLY COMPOSITIONS A2, E to G) Representative images at 10×; FIGS. 4C and 4D depict tissue samples treated with Composition A; FIGS. 4E and 4F depict a tissue sample treated with Composition B; FIGS. 4G and 4H depicts a tissue sample treated with Composition C; FIGS. 4I and 4J depict a tissue sample treated with Composition D; FIGS. 4K and 4L depict a tissue sample treated with Composition E; FIGS. 4M and 4N depict a tissue sample treated with Composition F; FIGS. 4O and 4P depict a tissue sample treated with Composition G; FIGS. 4Q and 4R depict a tissue sample treated with Composition H; No data was collected for Composition I; FIGS. 4S and 4T depict a tissue sample treated with Composition J; FIGS. 4U and 4V depict a tissue sample treated with Composition K; FIGS. 4W and 4X depict a tissue sample treated with Composition L; FIGS.

4Y and 4Z depict a tissue sample treated with Composition M; FIGS. 4AA and 4BB depict a tissue sample treated with Composition N; FIGS. 4CC and 4DD depict a tissue sample treated with Composition O; FIGS. 4EE and 4FF depict a tissue sample treated with Composition P; and FIGS. 4GG and 4HH depict a tissue sample treated with Composition Q.

All hydrogen peroxide containing compositions (Compositions B-J) had some potential impact on DAB stain hue changing from a chocolate or brown/red color towards a brown/orange color. Exposure at higher concentration hydrogen peroxide, higher incubation temperature or longer incubation times caused a more dramatic change. The about 1M citrate composition (pH=about 1.5) [Composition A] in absence of hydrogen peroxide did not have a discernable impact on DAB stain. Sodium chloride addition greatly reduced the DAB hue impact of the citrate-hydrogen peroxide compositions (E-G). The 25 mM glycine or citrate compositions containing about 1.0 wt % SDS caused a similar hue shift to that observed with hydrogen peroxide to Compositions A-D. Compositions K and L had a diminished DAB stain intensity with 4× treatments relative to the standard and 1× treatments. No obvious changes were observed with Composition M. Applicants believe that all compositions could be viable for use if DAB staining was performed last in a multiplex detection assay.

Example 12—Enzyme Inactivation Composition Impact on Alkaline Phosphatase Red IHC Chromogen Staining Tonsil tissue was stained for bcl2 (VMSI, #253-4290) with ultraView AP Red detection (VMSI #760-501) with Hematoxylin II counterstain. A bcl2 AP Red IHC model was used since the AP Red stain was not overly saturated and allowed for the ability to see subtle changes as above with DAB. The enzyme inactivation composition [1M citrate (pH=about 1.5), about 1.0 wt % $H_2O_2$, about 0.08 wt % $NaN_3$] was added during the IHC assay after standard AP Red chromogen detection and prior to hematoxylin counterstain (AP Multimer Incubation—Std. AP Red Detection—Enzyme Inactivation Composition—Hematoxylin II counterstaining). The AP enzyme inactivation sequence was performed 1× and 4× at about 41° C. for about 4 min. No discernable difference was observed in the primary AP Red chromogen stain before or after enzyme inactivation treatments up to 4×. Any observed change was believed to be less significant than with DAB chromogen and potentially within bounce of the instrument and ultraView Red detection system.

Example 13—Enzyme Inactivation Composition Impact on Tissue Antigen Staining Intensity (Bcl2 Tissue Antigen—Normal Tonsil)

The bcl2 antigen was chosen as an example test case since it is known to be impacted by various automated tissue treatments. The enzyme inactivation composition [1M citrate (pH=about 1.5), with or without 4N NaCl] was added during the IHC assay after cell conditioning and prior to 1° Ab incubation (Cell Conditioning—Elution Composition—1° Ab Incubation—HRP Multimer Incubation—Std. DAB Detection). The enzyme inactivation sequence was performed 1× and 4× at about 37° C. for about 16 min, the HRP enzyme inactivation condition in absence of hydrogen peroxide. The 1M citrate (pH=about 1.5) base alone did appear to have a potential negative impact on bcl2 DAB IHC staining with extended treatments. The 1× and 4× treatments afforded a similar bcl2 IHC staining pattern. However, the DAB staining intensity of the 4× treated sample was less than 1× treated sample, which was equivalent to the untreated standard. The bcl2 DAB IHC intensity was greatly decreased by the addition of 4N NaCl. It was believed that incubation time reduction from about 16 min to about 4 min could potentially decrease the protein denaturing impact of sodium chloride.

The enzyme inactivation sequence was performed with 1M citrate (pH=about 1.5) with and without additional about 1.0 wt % $H_2O_2$+about 0.08 wt % $NaN_3$ at about 37° C. for about 4 min, the conditions for inhibition in presence of hydrogen peroxide. The 1M citrate (pH=about 1.5) base was again confirmed to reduce bcl2 DAB IHC intensity with 4× inactivation treatments after cell conditioning and prior to 1° Ab incubation. The addition of about 1 wt % $H_2O_2$ and about 0.08 wt % $NaN_3$ reduced the negative tissue staining impact of the citrate base. Any observed variation in the DAB IHC staining could be within the expected instrument and detection system bounce. The bcl2 antigen detection signal intensity impact was similar to that observed with using VMSI PO inhibitor, a neutral reagent with similar hydrogen peroxide concentration. Initial evaluations with sodium chloride as an additive to the composition suggest that the addition imparts no substantial negative influence over the citrate-based reagent above. The IHC detection was at best subtly lighter with disclosed salt-based enzyme inactivation composition than the nominal citrate base without salt.

Example 14—Enzyme Inactivation Composition Impact on Tissue Antigen Detection Signal Intensity (CD8 Tissue Antigen—Normal Tissue)

The CD8 antigen was chosen for an example test case since it is known to be impacted by hydrogen peroxide reagents. The enzyme inactivation sequence was performed with 1M citrate (pH=about 1.5) with and without additional about 1.0 wt % $H_2O_2$+about 0.08 wt % $NaN_3$ at about 37° C. for about 4 min (Cell Conditioning—Enzyme Inactivation Composition—1° Ab Incubation—HRP Multimer Incubation—Std. DAB Detection). The enzyme inactivation sequence was performed 1× and 4× at about 37° C. for about 4 min, the conditions for HRP inhibition in presence of hydrogen peroxide. The enzyme inactivation compositions were assessed to have no discernible impact on CD8 antigen detection signal intensity with or without both hydrogen peroxide. DAB IHC staining patterns and intensity were judged equivalent to untreated standards. Initial evaluations with sodium chloride as an additive to the composition suggest that the addition imparts no substantial negative influence over the citrate-based reagent above. The CD8 IHC detection with the disclosed salt-based enzyme inactivation composition was at best subtly lighter than the nominal citrate base without salt. Any observed variation in the DAB IHC staining was believed to be within the expected instrument and detection system bounce.

Example 15—Enzyme Inactivation Composition Impact on Tissue Antigen Detection Signal Intensity (HER2 Antigen)

The HER2 antigen was chosen for an example test case since it is known to be impacted by various automated tissue treatments like bcl2. The enzyme inactivation sequence was performed with 1M citrate (pH=about 1.5), both with and without additional about 1.0 wt % $H_2O_2$+about 0.08 wt % $NaN_3$ at about 37° C. for about 4 min (Cell Conditioning—Elution Reagent—1° Ab Incubation—HRP Multimer Incubation—Std. DAB Detection). The enzyme inactivation sequence was performed 1× and 4× at about 37° C. for about 4 min (the conditions for HRP inhibition in absence of hydrogen peroxide). The enzyme inactivation compositions' influence on HER2 antigen detection signal intensity was difficult to access since the slides contained individual cells and not serial tissue sections. The HER2 DAB IHC staining for the 1M citrate (pH=about 1.5) base composition with and without about 1.0 wt % $H_2O_2$+about 0.08 wt % $NaN_3$ staining patterns were judged to be equivalent to the untreated standard slides; however, the DAB IHC staining intensity for all treated slides were generally judged to be equivalent or darker than the standard slides. In each case, the enzyme inactivation treatment did not change HER2 diagnosis on the standard slides. Initial evaluations with sodium chloride as an additive to the composition suggested no substantial negative influence over the citrate-based reagent above. The IHC detection with disclosed salt-based enzyme inactivation composition was at best subtly lighter than the nominal citrate base without salt. Any observed variation in the DAB IHC staining was believed to be within the expected instrument and detection system bounce.

Example 16—Tissue Antigen Detection Signal Intensity: Enzyme Inactivation Composition/Method Impact Comparison As previously discussed in Examples 13, 14, and 15, enzyme inactivation compositions (reagent pH, $H_2O_2$ concentration, salt concentration, etc.) and instrument application conditions (incubation temperature, time, etc.) could potentially impact a tissue target's antigen detection signal intensity. The enzyme inactivation compositions/methods in Table 1 were screened for their impact on antigen detection signal intensity using OptiView DAB IHC staining of bcl2/tonsil (about 64 min CC1, about 32 min bcl2), CD8/tonsil (about 64 min CC1, about 16 min CD8) and HER2/VMSI Pathway™ HER2 4-in-1 test slides (about 32 min CC1, about 32 min HER2). Each of the enzyme inactivation compositions were tested during the IHC assay after cell conditioning and prior to 1° Ab incubation (Cell Conditioning—Elution Reagent—1° Ab Incubation—2° Ab Incubation—HRP Multimer Incubation—Std. DAB Detection). The enzyme inactivation sequence was performed 1× and 4× to access their potential cumulative antigen detection signal intensity impact. A single slide was stained per condition versus replicates to just initially investigate conditions during feasibility for check for drastic changes. Slides were evaluated by 3 pathologists and 2 qualified readers. Slides were scored for antigen detection signal intensity relative to standard slides. A +1 value was assigned if the detected antigen signal intensity increased relative to the standard, 0 if equivalent to standard or −1 if less than standard. The evaluations were summed and evaluated for their individual and overall detected antigen signal intensity impact. Results are shown in the Table 4 and FIGS. 5, 6, and 7.

TABLE 4

Enzyme inactivation/detection elution compositions and methods compared to disclosed leading enzyme inactivation composition candidates.

| Enzyme Inactivation Methods | Tissue Antigen IHC Detection Signal Impact | | | Sum of Impact |
|---|---|---|---|---|
| | bcl2 | CD8 | HER2 | |
| 1 M Citrate (pH = 1.5) (4 min, 37° C.) | −5 | 0 | 1 | −4 |
| 1 M Citrate (1.5), 1.0% $H_2O_2$, 0.08% $NaN_3$ (4 min, 37° C.) | −2 | 0 | 3 | 1 |
| 1 M Citrate (1.5), 0.5% $H_2O_2$, 0.08% $NaN_3$ (4 min, 37° C.) | 2 | −1 | −2 | −1 |
| 1 M Citrate (2.0), 1.0% $H_2O_2$, 0.08% $NaN_3$ (4 min, 37° C.) | 2 | 0 | −1 | 1 |
| 1 M Citrate base: pH = 1.5, 1.0% $H_2O_2$, 0.08% $NaN_3$ (4 min, 37° C.) | 1 | −2 | 2 | 1 |
| 1 M Citrate base (1.5) + 0.5 M NaCl (4 min, 37° C.) | 1 | 0 | 1 | 2 |
| 1 M Citrate base (1.5) + 0.75 M NaCl (4 min, 37° C.) | −2 | 0 | −2 | −4 |
| 1 M Citrate base (1.5) + 1.0 M NaCl (4 min, 37° C.) | 1 | −2 | −3 | −4 |
| 1 M Citrate base (1.5) + 2.0 M NaCl (4 min, 37° C.) | −3 | −3 | −3 | −9 |
| Ventana PO Inhibitor (3 × 4 min, 45° C.) | −3 | 0 | 0 | −3 |
| Ventana DISCO Inhibitor (3 × 12 min, 37° C.) | −2 | 5 | 1 | 4 |
| 25 mM Glycine (2.0) + 1.0% SDS (5 dp, JD, 32 min, 50° C.) | −1 | 1 | 0 | 0 |
| 25 mM Citrate (2.0) + 1.0% SDS (5 dp JD, 32 min, 50° C.) | −4 | −2 | 0 | −6 |
| 25 mM Glycine (2.0) + 1.0% SDS (3 dp, JD, 2 × 8 min, 50° C.) | 0 | −1 | −4 | −5 |
| 25 mM Citrate (2.0) + 1.0% SDS (3 dp, JD, 2 × 8 min, 50° C.) | 1 | 0 | 1 | 2 |
| Heat Denaturation (Reaction Buffer, 4 min, 90° C.) | −5 | −1 | 0 | −6 |
| Ventana CC1 Antigen Retrieval (8 min, 95° C.) | −4 | −4 | −1 | −9 |
| Ventana CC2 Antigen Retrieval (8 min, 95° C.) | −1 | 2 | 2 | 3 |

FIGS. 5A and 5B depict tissue stained with IHC DAB Standard with no treatment—bcl2, tonsil (64 min CC1, 32 min bcl2); Representative images at 5×. (2nd reagent formulation round standard AT 5B); FIGS. 5C and 5D depict tissue samples treated with Compositions A; FIGS. 5E and 5F depicts a tissue sample treated with Composition B; FIGS. 5G and 5H depict a tissue sample treated with Composition C; FIGS. 5I and 5J depict a tissue sample treated with Composition D; FIGS. 5K and 5L depict a tissue sample treated with Composition E; FIGS. 5M and 5N depict a tissue sample treated with Composition F; FIGS. 5O and 5P depict a tissue sample treated with Composition G; FIGS. 5Q and 5R depict a tissue sample treated with Composition H; No data was collected for Composition I; FIGS. 5S and 5T depict a tissue sample treated with Composition J; FIGS. 5U and 5V depict a tissue sample treated with Composition K; FIGS. 5W and 5X depict a tissue sample treated with Composition L; FIGS. 5Y and 5Z depict a tissue sample treated with Composition M; FIGS. 5AA and 5BB depict a tissue sample treated with Composition N; FIGS. 5CC and 5DD depict a tissue sample treated with Composition O; FIGS. 5EE and 5FF depict a tissue sample treated with Composition P; and FIGS. 5GG and 5HH depict a tissue sample treated with Composition Q.

FIGS. 6A and 6B depict tissue stained with IHC DAB Standard No. 1 with no treatment—CD8, tonsil (64 min CC1, 16 min CD8); Representative images at 10×. (2nd reagent formulation round standard at 5); FIGS. 6C and 6D depict tissue samples treated with Compositions A; FIGS. 6E and 6F depicts a tissue sample treated with Composition B; FIGS. 6G and 6H depict a tissue sample treated with Composition C; FIGS. 6I and 6J depict a tissue sample treated with Composition D; FIGS. 6K and 6L depict a tissue sample treated with Composition E; FIGS. 6M and 6N depict a tissue sample treated with Composition F; FIGS. 6O and 6P depict a tissue sample treated with Composition G; FIGS. 6Q and 6R depict a tissue sample treated with Composition H; No data was collected for Composition I; FIGS. 6S and 6T depict a tissue sample treated with Composition J; FIGS. 6U and 6V depict a tissue sample treated with Composition K; FIGS. 6W and 6X depict a tissue sample treated with Composition L; FIGS. 6Y and 6Z depict a tissue sample treated with Composition M; FIGS. 6AA and 6BB depict a tissue sample treated with Composition N; FIGS. 6CC and 6DD depict a tissue sample treated with Composition O; FIGS. 6EE and 6FF depict a tissue sample treated with Composition P; and FIGS. 6GG and 6HH depict a tissue sample treated with Composition Q.

FIGS. 7A and 7B depict tissue stained with IHC DAB Standard with no treatment—HER2, VMSI Pathway™ HER2 4-in-1 test slides (32 min CC1, 32 min HER2); Representative images at 10× of highest expression cells; (2nd reagent formulation round standard AT 7B; FIGS. 7C and 7D depict tissue samples treated with Compositions A; FIGS. 7E and 7F depicts a tissue sample treated with Composition B; FIGS. 7G and 7H depict a tissue sample treated with Composition C; FIGS. 7I and 7J depict a tissue sample treated with Composition D; FIGS. 7K and 7L depict a tissue sample treated with Composition E; FIGS. 7M and 7N depict a tissue sample treated with Composition F; FIGS. 7O and 7P depict a tissue sample treated with Composition G; FIGS. 7Q and 7R depict a tissue sample treated with Composition H; No data was collected for Composition I; FIGS. 7S and 7T depict a tissue sample treated with Composition J; FIGS. 7U and 7V depict a tissue sample treated with Composition K; FIGS. 7W and 7X depict a tissue sample treated with Composition L; FIGS. 7Y and 7Z depict a tissue sample treated with Composition M; FIGS. 7AA and 7BB depict a tissue sample treated with Composition N; FIGS. 7CC and 7DD depict a tissue sample treated with Composition O; FIGS. 7EE and 7FF depict a tissue sample treated with Composition P; and FIGS. 7GG and 7HH depict a tissue sample treated with Composition Q.

Without wishing to be bound by any particular theory, it is believed that preferred enzyme inactivation method should have minimal impact on tissue antigen detection signal intensity for either an individual marker or group of markers. The above antigen detection signal intensity results demonstrate that all enzyme inactivation methods could have an impact on tissue antigen detection signal intensity with some more obvious than others. Each enzyme inactivation method will require validation against both the antigen panel and tissue models used in the multiplex detection assay. It is believed that antigen detection signal intensity will be least impacted if the primary antibodies are pooled and simultaneously incubated prior to any endogenous enzyme or detection chemistry enzyme inactivation. This would be possible under very specialized detection systems enzyme detections using multiple 1° antibody species or hapten labeled 1° antibodies.

Example 17—Tissue Morphology Impact Comparison

Tour of tumor (TOT) and tour of body (TOB) microarray slides were stained with Ki67 (OptiView DAB, about 64 min CC1, about 16 min Ki67 1° Ab incubation) and a Hematoxylin II counterstain with or without enzyme inactivation. Each condition was tested with one treatment after antigen retrieval and prior to primary antibody incubation (Cell Conditioning—Elution Reagent—1° Ab Incubation—HRP Multimer Incubation—Std. DAB Detection). It was believed that no obvious tissue morphology changes were observed for any enzyme inactivation method relative to an untreated standard.

Example 18—Puddle Systems Versus Thin Films

The disclosed enzyme inactivation/detection elution compositions were also investigated in "thin-film" form. In these examples, approximately 120 µL of reagent was placed in direct contact to the test case under a cover tile with a rolling mix. The reagent composition was removed from the slide, washed with water and then Reaction Buffer prior to Hematoxylin II counterstain. The leading composition candidate 1 M Citrate (pH=about 1.5), about 1.0% $H_2O_2$, about 0.08% $NaN_3$ was diluted in a ratio of about 1 to about 4 in a reaction buffer and applied to test cases. In another example, 250 mM citrate (pH=about 2.5), about 1.0% $H_2O_2$, about 0.08% $NaN_3$ was applied to the test case. A pH=about 2.5 was achieved when about 1 M Citrate (pH=about 1.5), about 1.0% $H_2O_2$, about 0.08% $NaN_3$ was diluted in a ratio of about 1 to about 4 in reaction buffer. About 1.0% $H_2O_2$ was initially targeted since it has been shown that increased reagent composition concentrations provided more consistent results in thin-film IHC DAB staining. It is believed that the $H_2O_2$ concentration may be reduced from about 1.0 wt % to about 0.25 wt % $H_2O_2$ in other compositions.

Example 19—Enzyme Inactivation in Multiplex Detection Assays (Dual HRP Mediated Tissue Staining)

HRP mediated multiplex detection assays were performed comparing the disclosed enzyme inactivation compositions/methods [1M Citrate (pH=about 1.5)+about 1.0 wt % $H_2O_2$+ about 0.5 M NaCl+about 0.08 wt % $NaN_3$, about 37° C., about 4 min] to a preferred enzyme inactivation method [Ventana DISCO Inhibitor (3× about 12 min, about 37° C.)]. Tyramide chromogen detections were performed sequentially without cocktailing 1° antibodies. The first antibody detection sequence was completed before the second antibody detection sequence (1° Ab Incubation 1—HRP-Ab Incubation 1—Tyramide Chromogen Detection 1—Enzyme Inactivation—1° Ab Incubation 2—HRP-Ab Incubation 2—Tyramide Chromogen Detection 2). Each primary antibody (pre-diluted) was detected using the appropriate VMSI Discovery UltraMap anti-species antibody-HRP conjugates (VMSI #760-4313 and 760-4315). Ventana rabbit AntiCD8 antibody clone SP57 (VMSI #790-4460) was detected with TAMRA tyramide detection and Ventana mouse Anti-CD163 antibody clone MRQ-26 (VMSI #760-4437) was detected with Rhod110 tyramide detection. Primary antibody incubations were performed for about 32 minutes at about 37° C. with about 32 minute 2° anti-species Ab-HRP conjugate incubations at about 37° C. All tyramide detections were performed for about 40 min tyramide at 37° C. and 100 µM tyramide concentrations. Each experiment was performed in duplicate. Any tyramide chromogen tissue staining intensity differences observed were within what could be observed with potential instrument and assay bounces. The disclosed enzyme inactivation compositions/methods shortened the HRP enzyme inactivation step from about 60 minutes down to about 12 minutes. This reflects a significant time gain to decrease tissue-staining assay times in a higher ordered sequential multiplex detection assays. Similar results were achieved on HRP mediated DAB/tyramide chromogen detection assays using the same HRP enzyme inhibition assays.

Example 20—Enzyme Inactivation in Multiplex Detection Assays (Dual AP Mediated Tissue Staining)

HRP mediated multiplex detection assays were performed comparing the disclosed enzyme inactivation compositions/methods [1M Citrate (pH=about 1.5)+about 1.0 wt % $H_2O_2$+about 0.5 M NaCl+about 0.08 wt % $NaN_3$, about 37° C., about 4 min] to a preferred enzyme inactivation method being utilized with AP multiplex detection assays [Heat denaturation in Reaction Buffer, about 90° C., about 4 min]. A dual AP mediated chromogen tissue staining for CD8 and CD163 was performed on tonsil tissue using sequential tandem 1° antibody and chromogen detections with the appropriate enzyme inactivation between each detection step (1° Ab Incubation 1—AP-Ab Incubation 1—AP Chromogen Detection 1—Enzyme Inactivation—1° Ab Incubation 2—AP-Ab Incubation 2—AP Chromogen Detection 2). The 1° antibodies were diluted 1:1 in VMSI Antibody Diluent (VMSI #251-018) to control both direct AP staining intensity and background. [VMSI rabbit AntiCD8 antibody (VMSI #790-4460, clone SP57) with Discovery UltraMap Blue Anti-Rb Detection Kit (VMSI #760-155); VMSI mouse AntiCD163 antibody (VMSI #760-4437, clone MRQ-26) with Discovery UltraMap Red Anti-Ms detection kit (VMSI #760-154); about 32 min 1° Ab incubations (diluted 1:1 as above); about 32 min 2° Ab-AP conjugate incubations (pre-diluted); about 8 min total AP chromogen deposition time]. Each tissue staining experiment was performed in duplicate.

It has been shown that the disclosed low pH citrate enzyme inactivation composition and method completely denatured and inhibited AP without reducing the first AP chromogen signal intensity. The heat AP enzyme inactivation method at about 90° C. in Reaction Buffer provided similar results. Any AP chromogen tissue staining intensity differences observed were within what could be observed with potential instrument and assay bounces.

The CD8 and CD163 antibody staining demonstrated the potential impact that each enzyme inactivation composition or method could have on the second antibody detection. When CD163 was detected before CD8, the AP chromogen detections signal/background ratios closely reflected that expected from the corresponding standards with little impact on either chromogen intensity or background. However, when CD8 was detected before CD163, contrasting results were observed. In both enzyme inactivation methods, an increase in CD163 background staining was observed while the heat enzyme inactivation method in Reaction Buffer at about 90° C. providing a significantly higher background then the lower temperature disclosed composition method. More importantly, the added heat element denatured the CD163 antigen to the point where the positive AP chromogen tissue staining was almost completely lost. The disclosed low pH enzyme inactivation composition and method allowed for a similar enzyme inactivation time without using heat while still providing positive CD163 tissue AP staining similar to standard levels.

Additional Embodiments

Additional Embodiment 1. An enzyme inactivation composition comprising a polycarboxylic acid having a pH ranging from about 1 to about 3; a peroxide; and a preservative, wherein the peroxide is present in an amount ranging from between about 0.25% to about 5% by total weight of the composition, and wherein the preservative is present in an amount ranging from between about 0.05% to about 1.0% by total weight of the composition.

Additional Embodiment 2. The enzyme inactivation composition of additional embodiment 1, wherein the peroxide is hydrogen peroxide and the preservative is sodium azide.

Additional Embodiment 3. The enzyme inactivation composition of additional embodiment 2, wherein the polycarboxylic acid is a citrate.

Additional Embodiment 4. The enzyme inactivation composition of any of additional embodiments 1 to 3, further comprising an elution mitigation agent.

Additional Embodiment 5. The enzyme inactivation composition of additional embodiment 4, wherein the elution mitigation agent is sodium chloride.

Additional Embodiment 6. The enzyme inactivation composition of additional embodiment 3, wherein the composition has a pH of about 1.5, the peroxide is present in an amount of about 1% by total weight of the composition, and wherein the preservative is present in an amount of about 0.08% by total weight of the composition.

Additional Embodiment 7. The enzyme inactivation composition of additional embodiment 3, wherein the composition has a pH of about 1.5, the peroxide is present in an amount of about 0.5% by total weight of the composition, and wherein the preservative is present in an amount of about 0.08% by total weight of the composition.

Additional Embodiment 8. The enzyme inactivation composition of additional embodiment 3, wherein the composition has a pH of about 2.0, the peroxide is present in an amount of about 1% by total weight of the composition, and wherein the preservative is present in an amount of about 0.08% by total weight of the composition.

Additional Embodiment 9. The enzyme inactivation composition of additional embodiment 6, further comprising 0.5M sodium chloride.

Additional Embodiment 10. The enzyme inactivation composition of additional embodiment 6, further comprising 0.75M sodium chloride.

Additional Embodiment 11. The enzyme inactivation composition of additional embodiment 6, further comprising 1M sodium chloride.

Additional Embodiment 12. An enzyme inactivation composition consisting essentially of a polycarboxylic acid having a pH ranging from about 1 to about 3; a peroxide; and a preservative; wherein the peroxide is present in an amount ranging from between about 0.25% to about 1.5% by total weight of the composition, and wherein the preservative is present in an amount ranging from between about 0.05% to about 1.0% by total weight of the composition.

Additional Embodiment 13. An enzyme inactivation composition consisting of a polycarboxylic acid having a pH ranging from about 1 to about 3; a peroxide; and a preservative; wherein the peroxide is present in an amount ranging from between about 0.25% to about 1.5% by total weight of the composition, and wherein the preservative is present in an amount ranging from between about 0.05% to about 1.0% by total weight of the composition.

Additional Embodiment 14. A method of inactivating one or more enzymes in a biological sample comprising applying between about 50 μL to about 200 μL of an enzyme inactivation composition comprising a polycarboxylic acid, a peroxide, and a preservative to a biological sample, the biological sample comprising one or more reagent or endogenous enzymes, and wherein at least one of the composition or the biological sample are maintained at a temperature ranging from between about 25° C. to about 50° C. for a time period ranging from between about 4 minutes to about 16 minutes.

Additional Embodiment 15. The method of additional embodiment 14, further comprising the step of adding an elution mitigation agent to the biological sample.

Additional Embodiment 16. The method of additional embodiment 14 or 15, wherein the one or more reagent or endogenous enzymes are selected from the group consisting of a reagent peroxidase, an endogenous peroxidase, and an alkaline phosphatase.

Additional Embodiment 17. A method of inactivating one or more enzymes in a biological sample comprising applying between about 50 μL to about 200 μL of the enzyme inactivation composition of any of additional embodiments 6, 7, and 8 to a biological sample, the biological sample comprising one or more reagent or endogenous enzymes, and wherein at least one of the enzyme inactivation composition or the biological sample are maintained at a temperature between about 37° C. and about 41° C. for at least about 4 minutes.

Additional Embodiment 18. A method of inactivating one or more enzymes in a biological sample comprising applying between about 50 μL to about 200 μL of the enzyme inactivation composition of any of additional embodiments 9, 10, and 11 to a biological sample, the biological sample comprising one or more reagent or endogenous enzymes, and wherein at least one of the enzyme inactivation composition or the biological sample are maintained at a temperature between about 37° C. and about 41° C. for at least about 4 minutes.

Additional Embodiment 19. A kit comprising a first component comprising a polycarboxylic acid having a pH ranging from about 1 to about 3; a peroxide; and a preservative; wherein the peroxide is present in an amount ranging from between about 0.25% to about 5% by total weight of the composition, and wherein the preservative is present in an amount ranging from between about 0.05% to about 1.0% by total weight of the composition; and a second component comprising an elution mitigation agent.

Additional Embodiment 20. A method of detecting targets in a biological sample, comprising:
  a) contacting the biological sample with a first chromogenic detection reagent having a first enzyme;
  b) detecting a first signal from the first chromogenic detection reagent; and
  c) inactivating the first enzyme by applying a first enzyme inactivation composition comprising a polycarboxylic acid having a pH ranging from about 1 to about 3; and at least one of a peroxide or a preservative, wherein the peroxide is present in an amount ranging from between about 0.25% to about 5% by total weight of the composition, and wherein the preservative is present in an amount ranging from between about 0.05% to about 1.0% by total weight of the composition, wherein at least one of the first enzyme inactivation composition or the biological sample are maintained at a temperature ranging from between about 25° C. to about 50° C. for a time period ranging from between about 4 minutes to about 16 minutes.

Additional Embodiment 21. The method of additional embodiment 20, further comprising the steps of:
  a) contacting the biological sample with a second chromogenic detection reagent having a second enzyme;
  b) detecting a second signal from the second chromogenic detection reagent; and
  c) inactivating the second enzyme by applying a second enzyme inactivation composition comprising a polycarboxylic acid having a pH ranging from about 1 to about 3; and at least one of a peroxide or a preservative, wherein the peroxide is present in an amount ranging from between about 0.25% to about 5% by total weight of the composition, and wherein the preservative is present in an amount ranging from between about 0.05% to about 1.0% by total weight of the composition, wherein at least one of the second enzyme inactivation composition or the biological sample are maintained at a temperature ranging from between about 25° C. to about 50° C. for a time period ranging from between about 4 minutes to about 16 minutes.

Additional Embodiment 22. The method of additional embodiment 20 or 21, wherein at least one of the first or second enzyme inactivation compositions comprises citrate, hydrogen peroxide, and sodium azide, wherein the composition has a pH of about 1.5, the hydrogen peroxide is present in an amount of about 1% by total weight of the composition, and wherein the sodium azide is present in an amount of about 0.08% by total weight of the composition.

Additional Embodiment 23. The method of additional embodiment 22, wherein the composition further comprises sodium chloride.

Additional Embodiment 24. A biological sample comprising one or more enzymes that are either substantially inactivated or completely inactivated, the biological sample prepared by applying an enzyme inactivation composition comprising citrate, hydrogen peroxide, and sodium azide, wherein the composition has a pH of about 1.5, the hydrogen peroxide is present in an amount of about 1% by total weight of the composition, and wherein the sodium azide is present in an amount of about 0.08% by total weight of the composition, and wherein the composition is allowed to remain in contact with the biological sample for at least about 4 minutes at a temperature of between about 25° C. and about 41° C.

Additional Embodiment 25. The biological sample of additional embodiment 24, wherein the composition further comprises sodium chloride.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the invention herein has been described with reference to particular embodiments, it is to be understood that these embodiments are merely illustrative of the principles and applications of the present invention. It is therefore understood that numerous modifications may be made to the illustrative embodiments and that other arrangements may be devised without departing from the spirit and scope of the present invention as defined by the appended claims.

The invention claimed is:

1. A method of inactivating one or more enzymes in a biological sample comprising applying between about 50 μL to about 200 μL of an enzyme inactivation composition comprising a polycarboxylic acid, a peroxide, and a preservative to the biological sample, wherein the enzyme inactivation composition has a pH ranging from between about 1 to about 3, the biological sample comprising one or more reagent or endogenous enzymes, and wherein at least one of the enzyme inactivation composition or the biological sample is maintained at a temperature ranging from between about 25° C. to about 50° C. for a time period ranging from between about 4 minutes to about 16 minutes.

2. The method of claim 1, wherein the one or more reagent or endogenous enzymes are selected from the group consisting of a reagent peroxidase, an endogenous peroxidase, and an alkaline phosphatase.

3. The method of claim 1, wherein the polycarboxylic acid comprises a citrate or an isocitrate.

4. The method of claim 1, further comprising the step of contacting the biological sample with an elution mitigation agent.

5. The method of claim 4, wherein the elution mitigation agent comprises sodium chloride.

6. The method of claim 1, wherein the preservative comprises sodium azide.

7. The method of claim 1, wherein the peroxide is present in an amount ranging from between about 0.25% to about 5% by total weight of the enzyme inactivation composition.

8. The method of claim 1, wherein the preservative is present in an amount ranging from between about 0.05% to about 1.0% by total weight of the enzyme inactivation composition.

9. The method of claim 1, wherein the temperature ranges from between about 37° C. to about 50° C.

10. The method of claim 9, wherein the time period ranges from between about 4 minutes to about 8 minutes.

11. The method of claim 1, wherein the one or more reagent or endogenous enzymes are selected from the group consisting of neuraminidase, galactosidase, and nitroreductase.

12. The method of claim 1, wherein the one or more reagent or endogenous enzymes are reagent enzymes.

* * * * *